US011193121B2

(12) United States Patent
Hindson et al.

(10) Patent No.: US 11,193,121 B2
(45) Date of Patent: *Dec. 7, 2021

(54) PARTITIONING AND PROCESSING OF ANALYTES AND OTHER SPECIES

(71) Applicant: 10X GENOMICS, INC., Pleasanton, CA (US)

(72) Inventors: Benjamin Hindson, Pleasanton, CA (US); Serge Saxonov, Oakland, CA (US); Kevin Ness, Pleasanton, CA (US); Paul Hardenbol, San Francisco, CA (US); Christopher Hindson, Pleasanton, CA (US); Donald Masquelier, Tracy, CA (US); Mirna Jarosz, Palo Alto, CA (US); Michael Schnall-Levin, San Francisco, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 120 days.

This patent is subject to a terminal disclaimer.

(21) Appl. No.: 16/170,980

(22) Filed: Oct. 25, 2018

(65) Prior Publication Data
US 2019/0276817 A1    Sep. 12, 2019

Related U.S. Application Data

(63) Continuation of application No. 15/693,374, filed on Aug. 31, 2017, now Pat. No. 10,150,964, which is a continuation of application No. 15/470,814, filed on Mar. 27, 2017, now Pat. No. 10,150,963, which is a continuation of application No. 14/175,935, filed on Feb. 7, 2014, now Pat. No. 9,644,204.

(60) Provisional application No. 61/762,435, filed on Feb. 8, 2013, provisional application No. 61/800,223, filed on Mar. 15, 2013, provisional application No. 61/840,403, filed on Jun. 27, 2013, provisional application No. 61/844,804, filed on Jul. 10, 2013.

(51) Int. Cl.
| C12N 15/10 | (2006.01) |
| C12Q 1/6806 | (2018.01) |
| C12N 15/11 | (2006.01) |
| G01N 33/543 | (2006.01) |
| C12Q 1/6876 | (2018.01) |
| C12Q 1/6874 | (2018.01) |

(52) U.S. Cl.
CPC .......... *C12N 15/1065* (2013.01); *C12N 15/11* (2013.01); *C12Q 1/6806* (2013.01); *C12Q 1/6874* (2013.01); *C12Q 1/6876* (2013.01); *G01N 33/5436* (2013.01); *C12Q 2600/112* (2013.01)

(58) Field of Classification Search
CPC ...... C12N 15/1065; C12N 15/11; C12Q 1/68; C12Q 1/6806
See application file for complete search history.

(56) References Cited

U.S. PATENT DOCUMENTS

| 2,797,149 A | 6/1957 | Skeggs |
| 3,047,367 A | 7/1962 | Kessler |
| 3,479,141 A | 11/1969 | William et al. |
| 4,124,638 A | 11/1978 | Hansen |
| 4,253,846 A | 3/1981 | Smythe et al. |
| 4,582,802 A | 4/1986 | Zimmerman et al. |
| 4,804,450 A * | 2/1989 | Mochizuki ............. C12M 35/02 435/285.2 |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,456,986 A * | 10/1995 | Majetich ............... B22F 1/0018 428/403 |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer et al. |
| 5,618,711 A | 4/1997 | Gelfand et al. |
| 5,658,548 A | 8/1997 | Padhye et al. |
| 5,695,940 A | 12/1997 | Drmanac et al. |

(Continued)

FOREIGN PATENT DOCUMENTS

| CN | 102292455 A | 12/2011 |
| CN | 102050953 B | 11/2012 |

(Continued)

OTHER PUBLICATIONS

Aikawa, et al. Spherical Phospholipid Polymer Hydrogels for Cell Encapsulation Prepared with a Flow-Focusing Microfluidic Channel Device. Langmuir. Jan. 31, 2012;28(4):2145-50. doi: 10.1021/la2037586. Epub Dec. 22, 2011.

Allazetta, et al. Microfluidic Synthesis of Cell-Type-Specific Artificial Extracellular Matrix Hydrogels. Biomacromolecules. Apr. 8, 2013;14(4):1122-31. doi: 10.1021/bm4000162. Epub Mar. 8, 2013.

Anonymous: "Dynal MPC(TM)-S", Oct. 13, 2008 (Oct. 13, 2008), XP055603532, Retrieved from the Internet on Jul. 9, 2019; URL:< https://www.veritastk.co.jp/products/pdf/120%2020D.Dynal_MPC-S%28rev005%29.pdf>.

(Continued)

*Primary Examiner* — Ethan C Whisenant
(74) *Attorney, Agent, or Firm* — Wilson Sonsini Goodrich & Rosati

(57) ABSTRACT

The present disclosure provides compositions, methods, systems, and devices for polynucleotide processing. Such polynucleotide processing may be useful for a variety of applications, including polynucleotide sequencing.

40 Claims, 16 Drawing Sheets
Specification includes a Sequence Listing.

(56) References Cited

U.S. PATENT DOCUMENTS

| | | |
|---|---|---|
| 5,700,642 A | 12/1997 | Monforte et al. |
| 5,705,628 A | 1/1998 | Hawkins |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,830,663 A | 11/1998 | Embleton et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,110,678 A | 8/2000 | Weisburg et al. |
| 6,123,798 A | 9/2000 | Gandhi et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,176,962 B1 | 1/2001 | Soane et al. |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,485,944 B1 | 11/2002 | Church et al. |
| 6,492,118 B1 | 12/2002 | Abrams et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,915,679 B2 | 7/2005 | Chien et al. |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,262,056 B2 | 8/2007 | Wooddell et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,076 B2 | 11/2009 | Davies et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |
| 7,772,287 B2 | 8/2010 | Higuchi et al. |
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,927,797 B2 | 4/2011 | Nobile et al. |
| 7,943,671 B2 | 5/2011 | Herminghaus et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet et al. |
| 8,658,430 B2 | 2/2014 | Miller et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismaglov et al. |

(56) References Cited

U.S. PATENT DOCUMENTS

| | | |
|---|---|---|
| 8,829,171 B2 | 9/2014 | Steemers et al. |
| 8,835,358 B2 | 9/2014 | Fodor et al. |
| 8,846,883 B2 | 9/2014 | Brown et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoj et al. |
| 8,986,628 B2 | 3/2015 | Stone et al. |
| 9,005,935 B2 | 4/2015 | Belyaev |
| 9,012,370 B2 | 4/2015 | Hong |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,040,256 B2 | 5/2015 | Grunenwald et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,085,798 B2 | 7/2015 | Chee |
| 9,089,844 B2 | 7/2015 | Hiddessen et al. |
| 9,102,980 B2 | 8/2015 | Brenner et al. |
| 9,126,160 B2 | 9/2015 | Ness et al. |
| 9,133,009 B2 | 9/2015 | Baroud et al. |
| 9,150,916 B2 | 10/2015 | Christen et al. |
| 9,156,010 B2 | 10/2015 | Colston et al. |
| 9,175,295 B2 | 11/2015 | Kaminaka et al. |
| 9,194,861 B2 | 11/2015 | Hindson et al. |
| 9,216,392 B2 | 12/2015 | Hindson et al. |
| 9,222,128 B2 * | 12/2015 | Saxonov ............... C12Q 1/6851 |
| 9,238,206 B2 | 1/2016 | Rotem et al. |
| 9,238,671 B2 | 1/2016 | Goryshin et al. |
| 9,249,460 B2 | 2/2016 | Pushkarev et al. |
| 9,266,104 B2 | 2/2016 | Link |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 * | 8/2016 | Hindson ............... C12Q 1/683 |
| 9,417,190 B2 | 8/2016 | Hindson et al. |
| 9,436,088 B2 | 9/2016 | Seul et al. |
| 9,486,757 B2 | 11/2016 | Romanowsky et al. |
| 9,498,761 B2 | 11/2016 | Holtze et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,623,384 B2 | 4/2017 | Hindson et al. |
| 9,637,799 B2 | 5/2017 | Fan et al. |
| 9,644,204 B2 * | 5/2017 | Hindson ............... C12N 15/11 |
| 9,689,024 B2 * | 6/2017 | Hindson ............... C12Q 1/6806 |
| 9,694,361 B2 * | 7/2017 | Bharadwaj ........ B01L 3/502761 |
| 9,695,468 B2 | 7/2017 | Hindson et al. |
| 9,701,998 B2 * | 7/2017 | Hindson ............... C12Q 1/6874 |
| 9,764,322 B2 | 9/2017 | Hiddessen et al. |
| 9,824,068 B2 | 11/2017 | Wong |
| 9,856,530 B2 | 1/2018 | Hindson et al. |
| 9,946,577 B1 | 4/2018 | Stafford et al. |
| 9,951,386 B2 * | 4/2018 | Hindson ............... C12Q 1/683 |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,017,759 B2 | 7/2018 | Kaper et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,119,167 B2 | 11/2018 | Srinivasan et al. |
| 10,137,449 B2 | 11/2018 | Bharadwaj et al. |
| 10,144,950 B2 | 12/2018 | Nolan |
| 10,150,117 B2 | 12/2018 | Bharadwaj et al. |
| 10,150,963 B2 * | 12/2018 | Hindson ............... G01N 33/5436 |
| 10,150,964 B2 * | 12/2018 | Hindson ............... G01N 33/5436 |
| 10,150,995 B1 | 12/2018 | Giresi et al. |
| 10,161,007 B2 | 12/2018 | Abate et al. |
| 10,167,509 B2 * | 1/2019 | Regan ............... C12Q 1/6827 |
| 10,174,310 B2 | 1/2019 | Nolan |
| 10,208,343 B2 | 2/2019 | Hindson et al. |
| 10,221,436 B2 | 3/2019 | Hardenbol et al. |
| 10,221,442 B2 * | 3/2019 | Hindson ............... C12Q 1/6806 |
| 10,227,648 B2 | 3/2019 | Hindson et al. |
| 10,253,364 B2 | 4/2019 | Hindson et al. |
| 10,273,541 B2 * | 4/2019 | Hindson ............... C12Q 1/6869 |
| 10,287,623 B2 * | 5/2019 | Jarosz ............... C12Q 1/6874 |
| 10,323,278 B2 | 6/2019 | Belgrader et al. |
| 10,323,279 B2 | 6/2019 | Hindson et al. |
| 10,337,061 B2 | 7/2019 | Hindson et al. |
| 10,344,329 B2 | 7/2019 | Hindson et al. |
| 10,347,365 B2 | 7/2019 | Wong et al. |
| 10,357,771 B2 | 7/2019 | Bharadwaj et al. |
| 10,395,758 B2 | 8/2019 | Schnall-Levin |
| 10,400,280 B2 * | 9/2019 | Hindson ............... C12Q 1/6816 |
| 10,428,326 B2 | 10/2019 | Belhocine et al. |
| 10,450,607 B2 | 10/2019 | Hindson et al. |
| 10,457,986 B2 | 10/2019 | Hindson et al. |
| 10,480,028 B2 | 11/2019 | Hindson et al. |
| 10,480,029 B2 | 11/2019 | Bent et al. |
| 10,533,221 B2 * | 1/2020 | Hindson ............... C12Q 1/6874 |
| 10,544,413 B2 | 1/2020 | Bharadwaj et al. |
| 10,549,279 B2 | 2/2020 | Bharadwaj et al. |
| 10,557,158 B2 | 2/2020 | Hardenbol et al. |
| 10,584,381 B2 | 3/2020 | Hindson et al. |
| 10,590,244 B2 | 3/2020 | Delaney et al. |
| 10,597,718 B2 * | 3/2020 | Hindson ............... C12Q 1/6806 |
| 10,612,090 B2 | 4/2020 | Hindson et al. |
| 10,626,458 B2 | 4/2020 | Hindson et al. |
| 10,669,583 B2 | 6/2020 | Hindson et al. |
| 10,676,789 B2 | 6/2020 | Hindson et al. |
| 10,745,742 B2 | 8/2020 | Bent et al. |
| 10,752,949 B2 * | 8/2020 | Hindson ............... C12Q 1/6855 |
| 11,021,749 B2 | 6/2021 | Hindson et al. |
| 11,035,002 B2 | 6/2021 | Hindson et al. |
| 11,078,522 B2 | 8/2021 | Hindson et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0051348 A1 | 12/2001 | Lee |
| 2001/0053519 A1 | 12/2001 | Fodor et al. |
| 2002/0001856 A1 | 1/2002 | Chow et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0119544 A1 | 8/2002 | Yan et al. |
| 2002/0127736 A1 | 9/2002 | Chou et al. |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027203 A1 | 2/2003 | Fields |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |

(56) References Cited

U.S. PATENT DOCUMENTS

| | | |
|---|---|---|
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0148335 A1 | 8/2003 | Shen et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0037813 A1 | 2/2004 | Simpson et al. |
| 2004/0040851 A1 | 3/2004 | Karger et al. |
| 2004/0063138 A1 | 4/2004 | McGinnis et al. |
| 2004/0068019 A1 | 4/2004 | Higuchi et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0185484 A1 | 9/2004 | Costa et al. |
| 2004/0195728 A1 | 10/2004 | Slomski et al. |
| 2004/0214175 A9 | 10/2004 | McKernan et al. |
| 2004/0224331 A1 | 11/2004 | Cantor et al. |
| 2004/0258701 A1 | 12/2004 | Dominowski et al. |
| 2005/0019839 A1 | 1/2005 | Jespersen et al. |
| 2005/0037397 A1 | 2/2005 | Mirkin et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0136417 A1 | 6/2005 | Cole et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0250147 A1 | 11/2005 | Macevicz |
| 2005/0266582 A1 | 12/2005 | Modlin et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0153924 A1 | 7/2006 | Griffiths et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0009954 A1 | 1/2007 | Wang et al. |
| 2007/0020617 A1 | 1/2007 | Trnovsky et al. |
| 2007/0020640 A1 | 1/2007 | McCloskey et al. |
| 2007/0026401 A1 | 2/2007 | Hofmann et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0105972 A1 | 5/2007 | Doyle et al. |
| 2007/0111241 A1 | 5/2007 | Cereb et al. |
| 2007/0134277 A1 | 6/2007 | Chen et al. |
| 2007/0141584 A1 | 6/2007 | Roberts et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0196397 A1 | 8/2007 | Torii et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0124726 A1 | 5/2008 | Monforte |
| 2008/0138878 A1 | 6/2008 | Kubu et al. |
| 2008/0166720 A1 | 7/2008 | Hsieh et al. |
| 2008/0213766 A1 | 9/2008 | Brown et al. |
| 2008/0228268 A1 | 9/2008 | Shannon et al. |
| 2008/0241820 A1 | 10/2008 | Krutzik et al. |
| 2008/0242560 A1 | 10/2008 | Gunderson et al. |
| 2008/0268431 A1 | 10/2008 | Choy et al. |
| 2008/0268450 A1 | 10/2008 | Nam et al. |
| 2008/0268507 A1 | 10/2008 | Xu et al. |
| 2008/0295909 A1 | 12/2008 | Locascio et al. |
| 2008/0299595 A1 | 12/2008 | Wong et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0062129 A1 | 3/2009 | McKernan et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0131543 A1 | 5/2009 | Weitz et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155563 A1 | 6/2009 | Petsev et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0235990 A1 | 9/2009 | Beer |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2009/0325260 A1 | 12/2009 | Otto et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0035254 A1 | 2/2010 | Williams |
| 2010/0055677 A1* | 3/2010 | Colston, Jr. ....... B01L 3/502784 435/6.13 |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0105866 A1 | 4/2010 | Fraden et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |

(56) References Cited

U.S. PATENT DOCUMENTS

| | | |
|---|---|---|
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0187705 A1 | 7/2010 | Lee et al. |
| 2010/0197507 A1 | 8/2010 | Rothberg et al. |
| 2010/0203647 A1 | 8/2010 | Hang et al. |
| 2010/0210479 A1 | 8/2010 | Griffiths et al. |
| 2010/0216153 A1 | 8/2010 | Lapidus et al. |
| 2010/0244818 A1* | 9/2010 | Atwood ............ G01N 37/005 324/233 |
| 2010/0248237 A1 | 9/2010 | Froehlich et al. |
| 2010/0248991 A1 | 9/2010 | Roesler et al. |
| 2010/0285975 A1 | 11/2010 | Mathies et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0159499 A1 | 6/2011 | Hindson et al. |
| 2011/0160078 A1 | 6/2011 | Fodor et al. |
| 2011/0166034 A1 | 7/2011 | Kwong et al. |
| 2011/0195496 A1 | 8/2011 | Muraguchi et al. |
| 2011/0201526 A1 | 8/2011 | Berka et al. |
| 2011/0212090 A1 | 9/2011 | Pedersen et al. |
| 2011/0217736 A1* | 9/2011 | Hindson ............ C12P 19/34 435/91.2 |
| 2011/0218123 A1 | 9/2011 | Weitz et al. |
| 2011/0250597 A1 | 10/2011 | Larson et al. |
| 2011/0257889 A1 | 10/2011 | Klammer et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |
| 2011/0281738 A1 | 11/2011 | Drmanac et al. |
| 2011/0287435 A1 | 11/2011 | Grunenwald et al. |
| 2011/0287947 A1 | 11/2011 | Chen et al. |
| 2011/0293701 A1 | 12/2011 | Bratzler et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010091 A1 | 1/2012 | Linnarson et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0034603 A1 | 2/2012 | Oliphant et al. |
| 2012/0041727 A1 | 2/2012 | Mishra et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van et al. |
| 2012/0172259 A1 | 7/2012 | Rigatti et al. |
| 2012/0184449 A1 | 7/2012 | Hixson et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0219947 A1 | 8/2012 | Yurkovetsky et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0230338 A1 | 9/2012 | Ganeshalingam et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0289428 A1 | 11/2012 | Duffy et al. |
| 2012/0295819 A1 | 11/2012 | Leamon et al. |
| 2012/0297493 A1 | 11/2012 | Cooper et al. |
| 2012/0309002 A1 | 12/2012 | Link |
| 2012/0316074 A1 | 12/2012 | Saxonov et al. |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0079251 A1 | 3/2013 | Boles |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0109596 A1 | 5/2013 | Peterson et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0171679 A1 | 7/2013 | Lee et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0243689 A1 | 9/2013 | Amiji et al. |
| 2013/0268206 A1 | 10/2013 | Porreca et al. |
| 2013/0273640 A1 | 10/2013 | Krishnan et al. |
| 2013/0274117 A1 | 10/2013 | Church et al. |
| 2013/0296173 A1 | 11/2013 | Callow et al. |
| 2013/0311106 A1 | 11/2013 | White et al. |
| 2013/0343317 A1 | 12/2013 | Etemad et al. |
| 2013/0344508 A1 | 12/2013 | Schwartz et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0080717 A1 | 3/2014 | Li et al. |
| 2014/0093916 A1 | 4/2014 | Belyaev et al. |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199331 A1 | 7/2014 | Robillard et al. |
| 2014/0199730 A1 | 7/2014 | Agresti et al. |
| 2014/0199731 A1 | 7/2014 | Agresti et al. |
| 2014/0200166 A1 | 7/2014 | Rooyen et al. |
| 2014/0206073 A1 | 7/2014 | Park et al. |
| 2014/0206554 A1 | 7/2014 | Hindson et al. |
| 2014/0214334 A1 | 7/2014 | Plattner et al. |
| 2014/0221239 A1 | 8/2014 | Carman et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0243242 A1 | 8/2014 | Nicol et al. |
| 2014/0272996 A1 | 9/2014 | Bemis |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0323316 A1 | 10/2014 | Drmanac et al. |
| 2014/0338753 A1 | 11/2014 | Sperling et al. |
| 2014/0357500 A1 | 12/2014 | Vigneault et al. |
| 2014/0357530 A1 | 12/2014 | Zhang et al. |

(56) References Cited

U.S. PATENT DOCUMENTS

| | | |
|---|---|---|
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0024950 A1 | 1/2015 | Bielas et al. |
| 2015/0031037 A1 | 1/2015 | Li et al. |
| 2015/0057163 A1 | 2/2015 | Rotem et al. |
| 2015/0066385 A1 | 3/2015 | Schnall-Levin et al. |
| 2015/0072396 A1 | 3/2015 | Gee et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0119280 A1 | 4/2015 | Srinivas et al. |
| 2015/0125904 A1 | 5/2015 | Ting et al. |
| 2015/0133317 A1 | 5/2015 | Robinson et al. |
| 2015/0133344 A1 | 5/2015 | Shendure et al. |
| 2015/0211056 A1 | 7/2015 | Um et al. |
| 2015/0218633 A1 | 8/2015 | Hindson et al. |
| 2015/0220532 A1 | 8/2015 | Wong |
| 2015/0224466 A1 | 8/2015 | Hindson et al. |
| 2015/0225777 A1 | 8/2015 | Hindson et al. |
| 2015/0225778 A1 | 8/2015 | Hindson et al. |
| 2015/0225786 A1 | 8/2015 | Litterst et al. |
| 2015/0232942 A1 | 8/2015 | Abate et al. |
| 2015/0247182 A1 | 9/2015 | Faham et al. |
| 2015/0258543 A1 | 9/2015 | Baroud et al. |
| 2015/0259736 A1 | 9/2015 | Steemers et al. |
| 2015/0267191 A1 | 9/2015 | Steelman et al. |
| 2015/0267246 A1 | 9/2015 | Baroud et al. |
| 2015/0291942 A1 | 10/2015 | Gloeckner et al. |
| 2015/0292988 A1 | 10/2015 | Bharadwaj et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329617 A1 | 11/2015 | Winther et al. |
| 2015/0329852 A1 | 11/2015 | Nolan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0368638 A1 | 12/2015 | Steemers et al. |
| 2015/0368694 A1 | 12/2015 | Pan et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Michael et al. |
| 2016/0008778 A1 | 1/2016 | Weitz et al. |
| 2016/0024558 A1 | 1/2016 | Hardenbol |
| 2016/0024572 A1 | 1/2016 | Shishkin et al. |
| 2016/0025726 A1 | 1/2016 | Altin et al. |
| 2016/0032282 A1 | 2/2016 | Vigneault et al. |
| 2016/0034093 A1 | 2/2016 | Xie et al. |
| 2016/0053253 A1 | 2/2016 | Salathia et al. |
| 2016/0059204 A1 | 3/2016 | Hindson et al. |
| 2016/0060621 A1 | 3/2016 | Agresti et al. |
| 2016/0060691 A1 | 3/2016 | Giresi et al. |
| 2016/0115474 A1 | 4/2016 | Jelinek et al. |
| 2016/0122753 A1 | 5/2016 | Mikkelsen et al. |
| 2016/0122817 A1 | 5/2016 | Jarosz et al. |
| 2016/0145683 A1 | 5/2016 | Fan et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0177375 A1 | 6/2016 | Abate et al. |
| 2016/0194699 A1 | 7/2016 | Borodina et al. |
| 2016/0201125 A1 | 7/2016 | Samuels et al. |
| 2016/0203196 A1 | 7/2016 | Schnall-Levin et al. |
| 2016/0208323 A1 | 7/2016 | Bernstein et al. |
| 2016/0231324 A1 | 8/2016 | Zhao et al. |
| 2016/0232291 A1 | 8/2016 | Kyriazopoulou-Panagiotopoulou et al. |
| 2016/0244742 A1 | 8/2016 | Linnarsson et al. |
| 2016/0244809 A1 | 8/2016 | Belgrader et al. |
| 2016/0244811 A1 | 8/2016 | Edwards |
| 2016/0244825 A1 | 8/2016 | Vigneault et al. |
| 2016/0251697 A1 | 9/2016 | Nolan et al. |
| 2016/0257984 A1 | 9/2016 | Hardenbol et al. |
| 2016/0281160 A1 | 9/2016 | Jarosz et al. |
| 2016/0289670 A1 | 10/2016 | Samuels et al. |
| 2016/0289769 A1 | 10/2016 | Schwartz et al. |
| 2016/0304860 A1 | 10/2016 | Hindson et al. |
| 2016/0314242 A1 | 10/2016 | Schnall-Levin et al. |
| 2016/0326583 A1 | 11/2016 | Johnson et al. |
| 2016/0348093 A1 | 12/2016 | Price et al. |
| 2016/0350478 A1 | 12/2016 | Chin et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0128937 A1 | 5/2017 | Hung et al. |
| 2017/0144161 A1 | 5/2017 | Hindson et al. |
| 2017/0145476 A1 | 5/2017 | Ryvkin et al. |
| 2017/0159109 A1 | 6/2017 | Zheng et al. |
| 2017/0183701 A1 | 6/2017 | Agresti et al. |
| 2017/0211127 A1 | 7/2017 | Mikkelsen et al. |
| 2017/0235876 A1 | 8/2017 | Jaffe et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0335385 A1 | 11/2017 | Hindson et al. |
| 2017/0342404 A1 | 11/2017 | Hindson et al. |
| 2017/0343545 A1 | 11/2017 | Hadrup et al. |
| 2017/0348691 A1 | 12/2017 | Bharadwaj et al. |
| 2017/0356027 A1 | 12/2017 | Hindson et al. |
| 2017/0362587 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0071695 A1 | 3/2018 | Weitz et al. |
| 2018/0080021 A1 | 3/2018 | Reuter et al. |
| 2018/0080075 A1 | 3/2018 | Brenner et al. |
| 2018/0087050 A1 | 3/2018 | Zheng et al. |
| 2018/0088112 A1 | 3/2018 | Fan et al. |
| 2018/0094298 A1 | 4/2018 | Hindson et al. |
| 2018/0094312 A1 | 4/2018 | Hindson et al. |
| 2018/0094313 A1 | 4/2018 | Hindson |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0179591 A1 | 6/2018 | Belgrader et al. |
| 2018/0180601 A1 | 6/2018 | Pedersen et al. |
| 2018/0195060 A1 | 7/2018 | Wang et al. |
| 2018/0195112 A1 | 7/2018 | Lebofsky et al. |
| 2018/0196781 A1 | 7/2018 | Wong |
| 2018/0216162 A1 | 8/2018 | Belhocine et al. |
| 2018/0237951 A1 | 8/2018 | Bock et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0267036 A1 | 9/2018 | Fan et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0305685 A1 | 10/2018 | Li et al. |
| 2018/0312822 A1 | 11/2018 | Lee et al. |
| 2018/0312873 A1 | 11/2018 | Zheng |
| 2018/0327839 A1 | 11/2018 | Hindson et al. |
| 2018/0334670 A1 | 11/2018 | Bharadwaj et al. |
| 2018/0335424 A1 | 11/2018 | Chen et al. |

(56) References Cited

U.S. PATENT DOCUMENTS

| | | |
|---|---|---|
| 2018/0340169 A1 | 11/2018 | Belhocine et al. |
| 2018/0340170 A1 | 11/2018 | Belhocine et al. |
| 2018/0340171 A1 | 11/2018 | Belhocine et al. |
| 2018/0340172 A1 | 11/2018 | Belhocine et al. |
| 2018/0340939 A1 | 11/2018 | Gaublomme et al. |
| 2018/0346970 A1 | 12/2018 | Chang et al. |
| 2018/0346979 A1 | 12/2018 | Hindson et al. |
| 2018/0363029 A1 | 12/2018 | Hindson et al. |
| 2018/0371538 A1 | 12/2018 | Blauwkamp et al. |
| 2018/0371540 A1 | 12/2018 | Hindson et al. |
| 2018/0371545 A1 | 12/2018 | Wong et al. |
| 2018/0376609 A1 | 12/2018 | Ju et al. |
| 2019/0002967 A1 | 1/2019 | Chen et al. |
| 2019/0024166 A1 | 1/2019 | Hindson et al. |
| 2019/0032129 A1 | 1/2019 | Hindson et al. |
| 2019/0032130 A1 | 1/2019 | Giresi et al. |
| 2019/0040382 A1 | 2/2019 | Steemers et al. |
| 2019/0040464 A1 | 2/2019 | Giresi et al. |
| 2019/0060890 A1 | 2/2019 | Bharadwaj et al. |
| 2019/0060904 A1 | 2/2019 | Bharadwaj et al. |
| 2019/0060905 A1 | 2/2019 | Bharadwaj et al. |
| 2019/0064173 A1 | 2/2019 | Bharadwaj et al. |
| 2019/0071656 A1 | 3/2019 | Chang et al. |
| 2019/0078150 A1 | 3/2019 | Chen et al. |
| 2019/0085391 A1 | 3/2019 | Hindson et al. |
| 2019/0100632 A1 | 4/2019 | Delaney et al. |
| 2019/0127731 A1 | 5/2019 | Mcdermott |
| 2019/0134633 A1 | 5/2019 | Bharadwaj et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0153436 A1 | 5/2019 | Belhocine et al. |
| 2019/0153532 A1 | 5/2019 | Bharadwaj et al. |
| 2019/0169666 A1 | 6/2019 | Hardenbol et al. |
| 2019/0169700 A1 | 6/2019 | Abate et al. |
| 2019/0176152 A1 | 6/2019 | Bharadwaj et al. |
| 2019/0203291 A1 | 7/2019 | Hindson et al. |
| 2019/0241965 A1 | 8/2019 | Abate et al. |
| 2019/0249226 A1 | 8/2019 | Bent et al. |
| 2019/0270983 A1 | 9/2019 | Belhocine et al. |
| 2019/0276817 A1 | 9/2019 | Hindson et al. |
| 2019/0316197 A1 | 10/2019 | Hindson et al. |
| 2019/0323088 A1 | 10/2019 | Boutet et al. |
| 2019/0330701 A1 | 10/2019 | Abate et al. |
| 2019/0344276 A1 | 11/2019 | Bharadwaj et al. |
| 2019/0345636 A1 | 11/2019 | Mcdermott et al. |
| 2019/0352717 A1 | 11/2019 | Schnall-Levin |
| 2019/0367997 A1 | 12/2019 | Bent et al. |
| 2019/0376058 A1 | 12/2019 | Belhocine et al. |
| 2019/0376118 A1 | 12/2019 | Belhocine et al. |
| 2020/0002763 A1 | 1/2020 | Belgrader et al. |
| 2020/0005902 A1 | 1/2020 | Mellen et al. |
| 2020/0020417 A1 | 1/2020 | Schnall-Levin et al. |
| 2020/0024596 A1 | 1/2020 | Belhocine et al. |
| 2020/0032335 A1 | 1/2020 | Alvarado Martinez |
| 2020/0033237 A1 | 1/2020 | Hindson et al. |
| 2020/0033366 A1 | 1/2020 | Alvarado Martinez |
| 2020/0056223 A1 | 2/2020 | Bell |
| 2020/0063191 A1 | 2/2020 | Meer et al. |
| 2020/0199669 A1 | 6/2020 | Hindson et al. |

FOREIGN PATENT DOCUMENTS

| | | |
|---|---|---|
| CN | 103202812 A | 7/2013 |
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1923471 A1 | 5/2008 |
| EP | 1944368 A1 | 7/2008 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| EP | 2635679 B1 | 4/2017 |
| EP | 3013957 B1 | 9/2018 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| JP | 2012522517 A | 9/2012 |
| KR | 20090081260 A | 7/2009 |
| RU | 2321638 C2 | 4/2008 |
| WO | WO-8402000 A1 | 5/1984 |
| WO | WO-9301498 A1 | 1/1993 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9942597 A1 | 8/1999 |
| WO | WO-9952708 A1 | 10/1999 |
| WO | WO-9967641 A2 | 12/1999 |
| WO | WO-0008212 A1 | 2/2000 |
| WO | WO-0023181 A1 | 4/2000 |
| WO | WO-0026412 A1 | 5/2000 |
| WO | WO-0034527 A2 | 6/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006040551 A2 | 4/2006 |
| WO | WO-2006071770 A2 | 7/2006 |
| WO | WO-2006078841 A2 | 7/2006 |
| WO | WO-2006086210 A2 | 8/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |

(56) References Cited

FOREIGN PATENT DOCUMENTS

| | | |
|---|---|---|
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008135512 A2 | 11/2008 |
| WO | WO-2008150432 A1 | 12/2008 |
| WO | WO-2008135512 A3 | 1/2009 |
| WO | WO-2009005680 A1 | 1/2009 |
| WO | WO-2009011808 A1 | 1/2009 |
| WO | WO-2009015296 A1 | 1/2009 |
| WO | WO-2009023821 A1 | 2/2009 |
| WO | WO-2009048532 A2 | 4/2009 |
| WO | WO-2009061372 A1 | 5/2009 |
| WO | WO-2009085215 A1 | 7/2009 |
| WO | WO-2009147386 A1 | 12/2009 |
| WO | WO-2009152928 A2 | 12/2009 |
| WO | WO-2010004018 A2 | 1/2010 |
| WO | WO-2010009735 A2 | 1/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010127304 A2 | 11/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011106314 A2 | 9/2011 |
| WO | WO-2011140627 A1 | 11/2011 |
| WO | WO-2011156529 A2 | 12/2011 |
| WO | WO-2012012037 A1 | 1/2012 |
| WO | WO-2012019765 A1 | 2/2012 |
| WO | WO-2011140510 A3 | 3/2012 |
| WO | WO-2012047889 A2 | 4/2012 |
| WO | WO-2012048340 A2 | 4/2012 |
| WO | WO-2012048341 A1 | 4/2012 |
| WO | WO-2012055929 A1 | 5/2012 |
| WO | WO-2012061832 A1 | 5/2012 |
| WO | WO-2012083225 A2 | 6/2012 |
| WO | WO-2012087736 A1 | 6/2012 |
| WO | WO-2012100216 A2 | 7/2012 |
| WO | WO-2012106546 A2 | 8/2012 |
| WO | WO-2012112804 A1 | 8/2012 |
| WO | WO-2012112970 A2 | 8/2012 |
| WO | WO-2012116250 A1 | 8/2012 |
| WO | WO-2012116331 A2 | 8/2012 |
| WO | WO-2012136734 A1 | 10/2012 |
| WO | WO-2012142531 A2 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012150317 A1 | 11/2012 |
| WO | WO-2012166425 A2 | 12/2012 |
| WO | WO-2012167142 A2 | 12/2012 |
| WO | WO-2013019751 A1 | 2/2013 |
| WO | WO-2013022961 A1 | 2/2013 |
| WO | WO-2013035114 A1 | 3/2013 |
| WO | WO-2013036929 A1 | 3/2013 |
| WO | WO-2013055955 A1 | 4/2013 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014018460 A1 | 1/2014 |
| WO | WO-2014028378 A2 | 2/2014 |
| WO | WO-2014028537 A1 | 2/2014 |
| WO | WO-2014053854 A1 | 4/2014 |
| WO | WO-2014071361 A1 | 5/2014 |
| WO | WO-2014072703 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014145047 A1 | 9/2014 |
| WO | WO-2014150931 A1 | 9/2014 |
| WO | WO-2014165559 A2 | 10/2014 |
| WO | WO-2014182835 A1 | 11/2014 |
| WO | WO-2014189957 A2 | 11/2014 |
| WO | WO-2014200767 A1 | 12/2014 |
| WO | WO-2014210353 A2 | 12/2014 |
| WO | WO-2015015199 A2 | 2/2015 |
| WO | WO-2015031691 A1 | 3/2015 |
| WO | WO-2015044428 A1 | 4/2015 |
| WO | WO-2014210353 A3 | 7/2015 |
| WO | WO-2015157567 A1 | 10/2015 |
| WO | WO-2015164212 A1 | 10/2015 |
| WO | WO-2015185067 A1 | 12/2015 |
| WO | WO-2015188839 A2 | 12/2015 |
| WO | WO-2015200891 A1 | 12/2015 |
| WO | WO-2015200893 A2 | 12/2015 |
| WO | WO-2016040476 A1 | 3/2016 |
| WO | WO-2016033251 A3 | 4/2016 |
| WO | WO-2016061517 A2 | 4/2016 |
| WO | WO-2016100976 A2 | 6/2016 |
| WO | WO-2016126871 A2 | 8/2016 |
| WO | WO-2016126882 A1 | 8/2016 |
| WO | WO-2016130578 A1 | 8/2016 |
| WO | WO-2016138496 A1 | 9/2016 |
| WO | WO-2016145409 A1 | 9/2016 |
| WO | WO-2016149661 A1 | 9/2016 |
| WO | WO-2016168584 A1 | 10/2016 |
| WO | WO-2016170126 A1 | 10/2016 |
| WO | WO-2016187256 | 11/2016 |
| WO | WO-2016187717 A1 | 12/2016 |
| WO | WO-2016191618 A1 | 12/2016 |
| WO | WO-2016207647 A2 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017034970 A1 | 3/2017 |
| WO | WO-2017053905 A1 | 3/2017 |
| WO | WO-2017075265 A1 | 5/2017 |
| WO | WO-2017075294 A1 | 5/2017 |
| WO | WO-2017079593 A1 | 5/2017 |
| WO | WO-2017096158 A1 | 6/2017 |
| WO | WO-2017117358 A1 | 7/2017 |
| WO | WO-2017151828 A1 | 9/2017 |
| WO | WO-2017156336 A1 | 9/2017 |
| WO | WO-2017180420 A1 | 10/2017 |
| WO | WO-2017197343 A2 | 11/2017 |
| WO | WO-2017197343 A3 | 2/2018 |
| WO | WO-2018031631 A1 | 2/2018 |
| WO | WO-2018039338 A1 | 3/2018 |
| WO | WO-2018039969 A1 | 3/2018 |
| WO | WO-2018045186 A1 | 3/2018 |
| WO | WO-2018058073 A2 | 3/2018 |
| WO | WO-2018103025 A1 | 6/2018 |

(56) References Cited

FOREIGN PATENT DOCUMENTS

| | | |
|---|---|---|
| WO | WO-2018119301 A1 | 6/2018 |
| WO | WO-2018119447 A2 | 6/2018 |
| WO | WO-2018125982 A1 | 7/2018 |
| WO | WO-2018129368 A2 | 7/2018 |
| WO | WO-2018132635 A1 | 7/2018 |
| WO | WO-2018119447 A3 | 8/2018 |
| WO | WO-2018172726 A1 | 9/2018 |
| WO | WO-2018174827 A1 | 9/2018 |
| WO | WO-2018191701 A1 | 10/2018 |
| WO | WO-2018213643 A1 | 11/2018 |
| WO | WO-2018226546 A1 | 12/2018 |
| WO | WO-2018236615 A1 | 12/2018 |
| WO | WO-2018237209 A1 | 12/2018 |
| WO | WO-2019028166 A1 | 2/2019 |
| WO | WO-2019040637 A1 | 2/2019 |
| WO | WO-2019071039 A1 | 4/2019 |
| WO | WO-2019083852 A1 | 5/2019 |
| WO | WO-2019084043 A1 | 5/2019 |
| WO | WO-2019084165 A1 | 5/2019 |
| WO | WO-2019084328 A1 | 5/2019 |
| WO | WO-2019099751 A1 | 5/2019 |
| WO | WO-2019108851 A1 | 6/2019 |
| WO | WO-2019113235 A1 | 6/2019 |
| WO | WO-2019118355 A1 | 6/2019 |
| WO | WO-2019126789 A1 | 6/2019 |
| WO | WO-2019148042 A1 | 8/2019 |
| WO | WO-2019152108 A1 | 8/2019 |
| WO | WO-2019157529 A1 | 8/2019 |
| WO | WO-2019165318 A1 | 8/2019 |
| WO | WO-2019169028 A1 | 9/2019 |
| WO | WO-2019169347 A1 | 9/2019 |
| WO | WO-2019191321 A1 | 10/2019 |
| WO | WO-2019217758 A1 | 11/2019 |
| WO | WO-2020028882 A1 | 2/2020 |
| WO | WO-2020142779 A1 | 7/2020 |

OTHER PUBLICATIONS

Bansal et al. "An MCMC algorithm for haplotype assembly from whole-genome sequence data," (2008) Genome Res 18:1336-1346.

Bansal et al. "HapCUT: an efficient and accurate algorithm for the haplotype assembly problem," Bioinformatics (2008) 24:i153-i159.

Baret, "Surfactants in droplet-based microfluidics" Lab Chip (12(3):422-433 (2012).

Bassett, et al. Competitive ligand exchange of crosslinking ions for ionotropic hydrogel formation. J. Mater. Chern. B, 2016,4, 6175-6182.

Bedtools: General Usage, http://bedtools.readthedocs.io/en/latest/content/generalusage.html; Retrieved from the Internet Jul. 8, 2016.

Beer et al. On-Chip, Real-Time, Single-Copy Polymerase Chain Reaction in Picoliter Droplets. Anal Chem 79:8471-8475 (2007).

Bentley et al. "Accurate whole human genome sequencing using reversible terminator chemistry," (2008) Nature 456:53-59.

Bray, "The JavaScript Object Notation (JSON) Data Interchange Format," Mar. 2014, retrieved from the Internet Feb. 15, 2015; https://tools.ietf.org/html/rfc7159.

Brenner, et al. "In vitro cloning of complex mixtures of DNA on microbeads: physical separation of differentially expressed cDNAs." Proc Natl Acad Sci USA. Feb. 15, 20005;97(4):1665-7.

Buenrostro, et al., "Tranposition of native chromatin for fast and sensitive epigenomic profiling of open chromatin, DNA-binding proteins and nucleosome position", Nature Methods, 2013, 10(12): 1213-1218.

Chen et al. BreakDancer: an algorithm for high-resolution mapping of genomic structural variation. Nature Methods (2009) 6(9):677-681.

Chien et al. "Multiport flow-control system for lab-on-a-chip microfluidic devices", Fresenius J. Anal Chem, 371:106-111 (Jul. 27, 2001).

Cleary et al. "Joint variant and de novo mutation identification on pedigrees from highthroughput sequencing data,"J Comput Biol (2014) 21:405-419.

Co-pending PCT/US2019/046940, filed Aug. 16, 2019.
Co-pending U.S. Appl. No. 16/575,280, filed Sep. 18, 2019.
Co-pending U.S. Appl. No. 16/434,076, filed Jun. 6, 2019.
Co-pending U.S. Appl. No. 16/434,084, filed Jun. 6, 2019.
Co-pending U.S. Appl. No. 16/434,095, filed Jun. 6, 2019.
Co-pending U.S. Appl. No. 16/434,102, filed Jun. 6, 2019.
Co-pending U.S. Appl. No. 16/519,863, filed Jul. 23, 2019.
Co-pending U.S. Appl. No. 16/530,930, filed Aug. 2, 2019.
Co-pending U.S. Appl. No. 16/698,740, filed Nov. 27, 2019.
Co-pending U.S. Appl. No. 16/717,375, filed Dec. 17, 2019.
Co-pending U.S. Appl. No. 16/725,673, filed Dec. 23, 2019.
Co-pending U.S. Appl. No. 16/736,323, filed Jan. 7, 2020.
Co-pending U.S. Appl. No. 16/750,757, filed Jan. 23, 2020.

Dangla, et al. Droplet microfluidics driven by gradients of confinement. Proc Natl Acad Sci U S A. Jan. 15, 2013; 110(3): 853-858. Published online Jan. 2, 2013. doi: 10.1073/pnas.1209186110.

Duffy et al., Rapid Protyping of Microfluidic Systems and Polydimethylsiloxane, Anal Chem 70:4974-4984 (1998).

Eid, et al. Real-time DNA sequencing from single polymerase molecules. Science. Jan. 2, 2009;323(5910):133-8. doi: 10.1126/science.1162986. Epub Nov. 20, 2008.

Ekblom, R. et al. "A field guide to whole-genome sequencing, assembly and annotation" Evolutionary Apps (Jun. 24, 2014) 7(9):1026-1042.

Ellison, et al., EGFR Mutation Testing in Lung Ancer: A Review of Available Methods and Their Use for Analysis of Tumour Tissue and Cytology Samples, Journal of Clinical Pathology, 2013, 66:79-89.

Ellison et al. Mutations in Active-Site Residues of the Uracil-DNA Glycosytase Encoded by Vaccinia Virus are Incompatible with Virus Viability. J Virology (1996) 70(11):7965-7973.

Farrukh, et al. Bioconjugating Thiols to Poly(acrylamide) Gels for Cell Culture Using Methylsulfonyl Co-monomers. Angew Chem Int Ed Engl. Feb. 5, 2016;55(6):2092-6. doi: 10.1002/anie.201509986. Epub Jan. 6, 2016.

Fox, et al. Accuracy of Next Generation Sequencing Platforms. Next Gener Seq Appl. 2014;1. pii: 1000106.

Gordon et al. "Consed: A Graphical Tool for Sequence Finishing," Genome Research (1998) 8:198-202.

Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.

Hamady, M. et al. "Error-correcting barcoded primers for pyrosequencing hundreds of samples in multiplex" Nature Methods (2008) 5(3):235-237, Supplementary Data pp. 1-34.

Heng et al. "Fast and accurate long-read alignment with Burrows-Wheeler transform," Bioinformatics (2010) 25(14): 1754-1760.

Henke, et al. Enzymatic Crosslinking of Polymer Conjugates is Superior over Ionic or UV Crosslinking for the On-Chip Production of Cell-Laden Microgels. Macromol Biosci. Oct. 2016;16(10): 1524-1532. doi: 10.1002/mabi.201600174. Epub Jul. 21, 2016.

Huang et al. EagleView: A genome assembly viewer for next-generation sequencing technologies, Genome Research (2008) 18:1538-1543.

Illumina, Inc. An Introduction to Next-Generation Sequencing Technology. Feb. 28, 2012.

Islam, et al. Highly multiplexed and strand-specific single-cell RNA 5' end sequencing. Nat Protoc. Apr. 5, 2012;7(5):813-28. doi: 10.1038/nprot.2012.022.

Jaitin, et al. Massively parallel single-cell RNA-seq for marker-free decomposition of tissues into cell types. Science. Feb. 14, 2014;343(6172):776-9. doi: 10.1126/science.1247651.

Jarosz, M. et al. "Using 1ng of DNA to detect haplotype phasing and gene fusions from whole exome sequencing of cancer cell lines" Cancer Res (2015) 75(supp15):4742.

Jiang et al. Cell-laden microfluidic microgels fortissue regeneration. Lab Chip 16(23):4482-4506 (Nov. 2016).

Kanehisa et al. "KEGG: Kyoto Encyclopedia of Genes and Genomes," Nucleic Acids Research (2000) 28:27-30.

Kim et al. "HapEdit: an accuracy assessment viewer for haplotype assembly using massively parallel DNA-sequencing technologies," Nucleic Acids Research (2011) pp. 1-5.

(56) References Cited

OTHER PUBLICATIONS

Kobayashi, et al. Effect of slot aspect ratio on droplet formation from silicon straight-through microchannels. J Colloid Interface Sci. Nov. 1, 2004;279(1):277-80.

Kukwikila, et al. Assembly of a biocompatible triazole-linked gene by one-pot click-DNA ligation. Nature Chemistry (2017) doi:10.1038/nchem.2850.

Layer et al. "LUMPY: A probabilistic framework for structural variant discovery," Genome Biology (2014) 15(6):R84.

Li, et al. Step-emulsification in a microfluidic device. Lab Chip. Feb. 21, 2015;15(4):1023-31. doi: 10.1039/c4lc01289e.

Lippert et al. ""Algorithmic strategies for the single nucleotide polymorphism haplotype assembly problem, Brief. Bionform (2002) 3:23-31.

Maan, et al. Spontaneous droplet formation techniques for monodisperse emulsions preparation—Perspectives for food applications. Journal of Food Engineering. vol. 107, Issues 3-4, Dec. 2011, pp. 334-346.

Madl, et al. "Bioorthogonal Strategies for Engineering Extracellular matrices", Madal, Chritopher, Adv. Funct. Master. Jan. 19, 2018, vol. 28, 1706046, pp. 1-21.

Marquis, et al. Microfluidics-assisted diffusion self-assembly: toward the control of the shape and size of pectin hydrogel microparticles. Biomacromolecules. May 12, 2014;15(5):1568-78. doi: 10.1021/bm401596m. Epub Apr. 8, 2014.

McCoy, R. et al. "Illumina TruSeq Synthetic Long-Reads Empower De Novo Assembly and Resolve Complex, Highly-Repetitive Transposable Elements" PLOS (2014) 9(9):e1016689.

McKenna, Aaron et al. "The Genome Analysis Toolkit: A MapReduce Framework for Analyzing next-Generation DNA Sequencing Data." Genome Research 20.9 (2010): 1297-1303. PMC. Web. Feb. 2, 2017.

Miller et al. "Assembly Algorithms for next-generation sequencing data," Genomics, 95 (2010), pp. 315-327.

Myllykangas et al. "Efficient targeted resequencing of human germline and cancer genomes by oligonucleotide-selective sequencing," Nat Biotechnol, (2011) 29:1024-1027.

Nisisako, T. et al., Microfluidics large-scale integration on a chip for mass production of monodisperse droplets and particles, The Royal Society of Chemistry: Lab Chip, (Nov. 23, 2007) 8:287-293.

Novak, R. et al., "Single cell multiplex gene detection and sequencing using microfluidicallygenerated agarose emulsions" Angew. Chem. Int. Ed. Engl. (2011) 50(2):390-395.

Pelton, et al. (2011) Microgels and Their Synthesis: An Introduction, in Microgel Suspensions: Fundamentals and Applications (eds A. Fernandez-Nieves, H. M. Wyss, J. Mattsson and D. A. Weitz), Wiley-VCH Verlag GmbH & Co. KGaA, Weinheim, Germany, doi: 10.1002/9783527632992.ch1.

Priest, et al. Generation of Monodisperse Gel Emulsions in a Microfluidic Device, Applied Physics Letters, 88:024106 (2006).

Pushkarev et al. Single-molecule sequencing of an individual human genome, Nature Biotech (2009) 17:847-850.

Ritz, A. et al. "Characterization of structural variants with single molecule and hybrid sequencing approaches" Bioinformatics (2014) 30(24):3458-3466.

Sahin, et al. Microfluidic EDGE emulsification: the importance of interface interactions on droplet formation and pressure stability. Sci Rep. May 27, 2016;6:26407. doi: 10.1038/srep26407.

Sahiner. Single step poly(L-Lysine) microgel synthesis, characterization and biocompatibility tests. Polymer, vol. 121, Jul. 14, 2017, pp. 46-54.

Saikia, et al. Simultaneous multiplexed amplicon sequencing and transcriptome profiling in single cells. Nat Methods. Jan. 2019;16(1):59-62. doi: 10.1038/S41592-018-0259-9. Epub Dec. 17, 2018.

Seiffert, et al. Microfluidic fabrication of smart microgels from macromolecular precursors. 2010. Polymer.

Seiffert. Microgel capsules tailored by droplet-based microfluidics. Chemphyschem. Feb. 4, 2013;14(2):295-304. doi: 10.1002/cphc.201200749. Epub Dec. 6, 2012.

Shah, "Fabrication of mono disperse thermosensitive microgels and gel capsules in micro fluidic devices", Soft Matter, 4:2303-2309 (2008).

Shelbourne et al., "Fast copper-free click DNA ligation by the ring-strain promoted alkyneazide cycloaddition reaction," Chem. Commun., 2011, 47, 6257-6259.

Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.

Shih, et al. Photoclick Hydrogels Prepared from Functionalized Cyclodextrin and Poly(ethylene glycol) for Drug Delivery and in Situ Cell Encapsulation. Biomacromolecules. Jul. 13, 2015;16(7):1915-23. doi: 10.1021/acs.biomac.5b00471. Epub Jun. 3, 2015.

Spitale et al., "Structural imprints in vivo decode RNA regulatory mechanisms," Nature. Mar. 26, 2015;519(7544):486-90; doi: 10.1038/nature14263. Epub Mar. 18, 2015.

SSH Tunnel—Local and Remote Port Forwarding Explained With Examples, Trackets Blog, http://blog.trackets.com/2014/05/17/ssh-tunnel-local-and-remote-port-forwarding-explained with-examples.html; Retrieved from the Internet Jul. 7, 2016.

Tam, et al. Engineering Cellular Microenvironments with Photo- and Enzymatically Responsive Hydrogels: Toward Biomimetic 3D Cell Culture Models. Acc Chem Res. Apr. 18, 2017;50(4):703-713. doi: 10.1021/acs.accounts.6b00543. Epub Mar. 27, 2017.

Tewhey et al. The importance of phase information for human genomics, Nat Rev Genet (2011) 12:215-223.

The SAM/BAM Format Specificatio Working Group, "Sequence Allignment/ Map Format Specification," Dec. 28, 2014.

Turchinovich, et al. "Capture and Amplification by Tailing and Switching (CATS): An Ultrasensitive Ligation-Independent Method for Generation of DNA Libraries for Deep Sequencing from Picogram Amounts of DNA and RNA." RNA Biology 11.7 (2014): 817-828. PMC. Web. Nov. 13, 2017.

Umbanhowar, P.B., et al., "Monodisperse Emulsion Generation via Drop Break off in a Coflowing Stream," Langmuir, vol. 16, pp. 347-351 (2000).

Uttamapinant, et al. Fast, cell-compatible click chemistry with copper-chelating azides for biomolecular labeling.Angew. Chem. Int. End. Engl., Jun. 11, 2012: 51(24) pp. 5852-5856.

Van Duke, et al. Effect of viscosities of dispersed and continuous phases in microchannel oil-in-water emulsification. Microfluid Nanofluid (2010) 9: 77. https://doi.org/10.1007/s10404-009-0521-7.

Velasco, et al. Microfluidic encapsulation of cells in polymer microgels. Small. Jun. 11, 2012;8(11):1633-42. doi: 10.1002/smll.201102464. Epub Mar. 29, 2012.

Voskoboynik, A. et al. The genome sequence of the colonial chordate, Botryllus schlosseri. eLife, 2:e00569 (2013). doi: 10.7554/eLife.00569. Epub Jul. 2, 2013.

Wheeler et al., "Database resources of the National Center for Biotechnology Information," Nucleic Acids Res. (2007) 35 (Database issue): D5-12.

Zerbino, Daniel, "Velvet Manual—version 1.1," Aug. 15, 2008, pp. 1-22.

Zerbino, D.R. "Using the Velvet de novo assembler for short-read sequencing technologies" Curr Protoc Bioinformatics. Sep. 2010;Chapter 11:Unit 11.5. doi: 10.1002/0471250953.bi1105s31.

Zerbino et al. "Velvet: Algorithms for de novo short read assembly using de Bruijn graphs," Genome Research (2008) 18:821-829.

Zhang, H. et al. Massively Parallel Single-Molecule and Single-Cell Emulsion Reverse Transcription Polymerase Chain Reaction using Agarose Droplet Microfluidics. Anal Chem (2012) 84:3599-3606.

Zhang, H. et al. "Massively Parallel Single-Molecule and Single-Cell Emulsion Reverse Transcription Polymerase Chain Reaction using Agarose Droplet Microfluidics" Anal Chem (2012) 84:3599-3606, Supporting Information.

Co-pending U.S. Appl. No. 16/844,141, filed Apr. 9, 2020.

Co-pending U.S. Appl. No. 16/852,906, filed Apr. 20, 2020.

AH006633.3 (Homo sapiens clone P1 and PAC max interactor 1 (MXI1) gene, complete cds, NCBI Reference Sequence, priority to Jun. 10, 2016, 5 pages) (Year:2016).

Ahern, H. The Scientist, vol. 20, pp. 20 and 22. Jul. 1995.

(56) References Cited

OTHER PUBLICATIONS

Ailenberg, et al. (2000) Controlled Hot Start and Improved Specificity in Carrying Out PCR Utilizing Touch-Up and Loop Incorporated Primers (TULIPS). BioTechniques, 29:1018-1024. (Year: 2000).
Anonymous: "Three Ways to Get Intimate with Epigenetic Marks". Oct. 24, 2012. Retrieved from Internet: https://epigenie.com/three-ways-to-get-intimate-with-epigenetic-marks/.
Banchelli, et al. Phospholipid membranes decorated by cholesterol-based oligonucleotides as soft hybrid nanostructures. J Phys Chem B. Sep. 4, 2008;112(35):10942-52. doi: 10.1021/jp802415t. Epub Aug. 9, 2008.
Bentley, et al. 2008. Supplementary Information, pp. 1-55 Nature. Nov. 6, 2008; 456(7218):53-9.
Cejas, P. et al. "Chromatin immunoprecipitation from fixed clinical tissues reveals tumorspecific enhancer profiles" Nature Med (2016) 22(6):685-691.
Co-pending U.S. Appl. No. 16/228,261, filed Dec. 20, 2018.
Co-pending U.S. Appl. No. 16/228,362, filed Dec. 20, 2018.
Co-pending U.S. Appl. No. 16/230,936, filed Dec. 21, 2018.
Co-pending U.S. Appl. No. 16/231,142, filed Dec. 21, 2018.
Co-pending U.S. Appl. No. 16/231,185, filed Dec. 21, 2018.
Co-pending U.S. Appl. No. 16/242,962, filed Jan. 8, 2019.
Co-pending U.S. Appl. No. 16/246,322, filed Jan. 11, 2019.
Co-pending U.S. Appl. No. 16/249,688, filed Jan. 16, 2019.
Co-pending U.S. Appl. No. 16/294,769, filed Mar. 6, 2019.
Epicenter, EZ-Tn5 Transposase, Epicenter, 2012, 1-5. (Year: 2012).
Fanielli, M. et al. "Pathology tissue-chromatin immunoprecipitation, coupled with high-throughput sequencing, allows the epigenetic profiling of patient samples" PNAS (2010) 107(50):21535-21540.
Hebenstreit. Methods, Challenges and Potentials of Single Cell RNA-seq. Biology (Basel). Nov. 16, 2012;1(3):658-67. doi: 10.3390/biology1030658.
Mali, et al. Barcoding cells using cell-surface programmable DNA-binding domains. Nat Methods. May 2013;10(5):403-6. doi: 10.1038/nmeth.2407. Epub Mar. 17, 2013.
Meyer, et al. Targeted high-throughput sequencing of tagged nucleic acid samples. Nucleic Acids Res. 2007;35(15):e97.
Mignardi, M. et al. "Oligonucleotide gap-fill ligation for mutation detection and sequencing in situ" Nucl Acids Res (2015) 43(22):e151.
Pfeifer, et al. Bivalent cholesterol-based coupling of oligonucleotides to lipid membrane assemblies. J Am Chem Soc. Aug. 25, 2004;126(33):10224-5.
10X Genomics. 10x Genomics Chromium™ Single Cell 3' Solution Utilized for Perturb-seq Approach. Press Release. Dec. 19, 2016. Retrieved from https://www.10xgenomics.eom/news/10x-genomics-chromium-single-cell-3-solution-utilized-perturb-seq-approach/.
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci USA. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adamson et al., "Production of arrays of chemically distinct nanolitre plugs via repeated splitting in microfluidic devices", Lab Chip 6(9): 1178-1186 (Sep. 2006).
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.

Agasti, et al. Photocleavable DNA barcode-antibody conjugates allow sensitive and multiplexed protein analysis in single cells. J Amer Chem SocePub, Nov. 2, 2012, vol. 134, No. 45, p. 18499-18502.
Agresti, et al. Selection of ribozymes that catalyse multiple-turnover Diels-Alder cycloadditions by using in vitro compartmentalization. Proc Natl Acad Sci USA. Nov. 8, 2005;102(45):16170-5. Epub Oct. 31, 2005.
Ahern, "Biochemical, Reagents Kits Offer Scientists Good Return on Investment" The Scientist (1995) 9(15):1-7.
Aitman, et al. Copy number polymorphism in Fcgr3 predisposes to glomerulonephritis in rats and humans. Nature. Feb. 16, 2006;439(7078):851-5.
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anna, S.L., et al., "Formation of dispersions using "flow focusing" in microchannels," Applied Physics Letters, vol. 82, No. 3, pp. 364-366 (2003).
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "TCEP=HCI" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCI_UG.pdf.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Ason et al. DNA sequence bias during Tn5 transposition. Journal of molecular biology 335.5 (2004): 1213-1225.
Attia, et al. Micro-injection moulding of polymer microfluidic devices. Microfluidics and nanofluidics. 2009; 7(1):1-28.
Balikova, et al. Autosomal-dominant microtia linked to five tandem copies of a copy-number variable region at chromosome 4p16. Am J Hum Genet. Jan. 2008;82(1):181-7. doi: 10.1016/j.ajhg.2007.08.001.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10):1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bjornsson et al., Intra-individual change overtime in DNA methylation with familial clustering, JAMA, Jun. 25, 2008, vol. 299 No. 24, pp. 2877-2883.

(56) References Cited

OTHER PUBLICATIONS

Bodi, K. et al. "Comparison of Commercially Available Target Enrichment Methods for Next-Generation Sequencing" J Biomolecular Techniques (2013) 24:73-86.
Boone, et al. Plastic advances microfluidic devices. The devices debuted in silicon and glass, but plastic fabrication may make them hugely successful in biotechnology application. Analytical Chemistry. Feb. 2002; 78A-86A.
Boulanger, et al., "Massively parallel haplotyping on microscopic beads for the high-throughput phase analysis of single molecules", PLoS One, vol. 7:1-10, 2012.
Boyle, et al. "High-resolution genome-wide in vivo footprinting of diverse transcription factors in human cells", Genome Res. Mar. 2011;21(3):456-64.
Braeckmans et al., Scanning the Code. Modern Drug Discovery. 2003:28-32.
Bransky, et al. A microfluidic droplet generator based on a piezoelectric actuator. Lab Chip. Feb. 21, 2009;9(4):516-20. doi: 10.1039/b814810d. Epub Nov. 20, 2008.
Brenner, et al. In vitro cloning of complex mixtures of DNA on microbeads: physical separation of differentially expressed cDNAs. Proc Natl Acad Sci USA. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brouzes, et al. Droplet microfluidic technology for single-cell high-throughput screening. Proc Natl Acad Sci USA. Aug. 25, 2009;106(34):14195-200. doi: 10.1073/pnas.0903542106. Epub Jul. 15, 2009.
Brown, K., Targeted Sequencing Using Droplet-Based Microfluidics, RainDance Technologies, 2009, 1-18.
Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primersand uracil DNA glycosylase. PCR Methods Appl. Aug. 1993; 3(1):28-31.
Buenrostro, et al. ATAC-seq: A Method for Assaying Chromatin Accessibility Genome-Wide. CurrProtoc Mol Biol.; 109: 21.29.1-21.29.9. doi:10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Carroll, "The selection of high-producing cell lines using flow cytometry and cell sorting", Exp. Op. Bioi. Therp., 4:11 1821-1829 (2004).
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).

Casbon, et al., "Reflex: intramolecular barcoding of long-range PCR products for sequencing multiple pooled DNAs", Nucleic Acids Res., pp. 1-6, 2013.
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;l8(1):83-101.
Chen, et al. Chemical transfection of cells in picoliter aqueous droplets in fluorocarbon oil. Anal Chem. Nov. 15, 2011;83(22):8816-20. doi: 10.1021/ac2022794. Epub Oct. 17, 2011.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and ActuatorWorkshop, Hilton Head, SC. Jun. 8-11, 1998; 11-14.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chu, et al. Controllable monodisperse multiple emulsions. Angew Chem Int Ed Engl. 2007;46(47):8970-4.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Clausell-Tormos et al., "Droplet-based microfluidic platforms for the encapsulation and screening of mammalian cells and multicellular organisms", Chem. Biol. 15:427-437 (2008).
Cong, et al. Multiplex genome engineering using CRISPR/Cas systems. Science. 339.6121 (Feb. 15, 2013): 819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 16/033,065, filed Jul. 11, 2018.
Co-pending U.S. Appl. No. 16/043,874, filed Jul. 24, 2018.
Co-pending U.S. Appl. No. 16/044,374, filed Jul. 24, 2018.
Co-pending U.S. Appl. No. 16/052,486, filed Aug. 1, 2018.
Co-pending U.S. Appl. No. 16/056,231, filed Aug. 6, 2018.
Co-pending U.S. Appl. No. 16/107,685, filed Aug. 21, 2018.
Co-pending U.S. Appl. No. 16/138,448, filed Sep. 21, 2018.
Co-pending U.S. Appl. No. 16/144,832, filed Sep. 27, 2018.
Co-pending U.S. Appl. No. 16/160,576, filed Oct. 15, 2018.
Co-pending U.S. Appl. No. 16/160,719, filed Oct. 15, 2018.
Co-pending U.S. Appl. No. 16/165,389, filed Oct. 19, 2018.
Co-pending U.S. Appl. No. 16/206,168, filed Nov. 30, 2018.
Co-pending U.S. Appl. No. 16/212,441, filed Dec. 6, 2018.
Coufal, et al. L1 retrotrans position in human neural progenitor cells. Nature. Aug. 27, 2009;460(7259):1127-31. doi: 10.1038/nature08248. Epub Aug. 5, 2009.
Curcio. Improved Techniques for High-Throughput Molecular Diagnostics. PhD Thesis. 2002.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.

(56) References Cited

OTHER PUBLICATIONS

Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
De Bruin et al., UBS Investment Research. Q-Series®: DNA Sequencing. UBS Securities LLC. Jul. 12, 2007. 15 pages.
Dekker, et al. Capturing chromosome conformation. Science. Feb. 15, 2002;295(5558):1306-11.
Delehanty, et al. Peptides for specific intracellular delivery and targeting of nanoparticles: implications for developing nanoparticle-mediated drug delivery. Ther Deliv. Sep. 2010;1(3):411-33.
Demirci, et al. Single cell epitaxy by acoustic picolitre droplets. Lab Chip. Sep. 2007;7(9):1139-45. Epub Jul. 10, 2007.
Depristo, et al. A framework for variation discovery and genotyping using next-generation DNA sequencing data. Nature Genet 43:491-498 (2011).
Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doerr, "The smallest bioreactor", Nature Methods, 2:5 326 (2005).
Doshi, et al. Red blood cell-mimicking synthetic biomaterial particles. Proceedings of the National Academy of Sciences 106.51 (2009): 21495-21499.
Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Drmanac et al., Sequencing by hybridization (SBH): advantages, achievements, and opportunities. AdvBiochem Eng Biotechnol. 2002;77 :75-101.
Droplet Based Sequencing (slides) dated (Mar. 12, 2008).
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Epicentre., "EZ-Tn5TM Custom Transposome Construction Kits", http://www.epicentre.com, pp. 1-17, 2012.
Esser-Kahn, et al. Triggered release from polymer capsules. Macromolecules. 2011; 44:5539-5553.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. Noninvasive diagnosis of fetal aneuploidy by shotgun sequencing DNA from maternal blood. Proc Natl Acad Sci USA. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Fisher, et al. A scalable, fully automated process for construction of sequence-ready human exo me targeted capture libraries. Genome Biol. 2011;12(1):R1. doi: 10.1186/GB-2011-12-1-r1. Epub Jan. 4, 2011.

Frampton, G.M. et al. "Development and validation of a clinical cancer genomic profiling test based on massively parallel DNA sequencing" Nature Biotechnology (2013) 31(11):1023-1031. doi:10.1038/nbr.2696.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology.1999; 17:1109-1111.
Fulton, et al. Advanced multiplexed analysis with the FlowMetrix system. Clin Chem. Sep. 1997;43(9):1749-56.
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Garstecki, et al. Formation of monodisperse bubbles in a microfluidic flow-focusing device. Applied Physics Letters. 2004; 85(13):2649-2651. DOI: 10.1063/1.1796526.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Gericke, et al. Functional cellulose beads: preparation, characterization, and applications. Chemical reviews 113.7 (2013): 4812-4836.
Ghadessy, et al. Directed evolution of polymerase function by compartmentalized selfreplication. Proc Natl Acad Sci USA. 2001;98:4552-4557.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, X. et al. "CRISPR-Cas9 delivery to hard-to-transfect cells via membrane deformation" Science Advances (2015) 1(7): E1500454 (8 pages).
Haring, et al. Chromatin immunoprecipitation: optimization, quantitative analysis and data normalization. Plant Methods. 2007; 3: 11.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hiatt, et al. Parallel, tag-directed assembly of locally derived short sequence reads. Nat Methods. Feb. 2010;7(2):119-22. doi: 10.1038/nmeth.1416. Epub Jan. 17, 2010.

(56) References Cited

OTHER PUBLICATIONS

Hirsch et al. (2002) "Easily reversible desthiobiotin binding to streptavidin, avidin, and other biotin-binding proteins: uses for protein labeling, detection, and isolation." Analytical of Biochemistry 308(2):343-357.

Hjerten, et al. General methods to render macroporous stationary phases nonporous and deformable, exemplified with agarose and silica beads and their use in high-performance ionexchange and hydrophobic-interaction chromatography of proteins. Chromatographia 31.1-2 (1991): 85-94.

Holtze, et al. Biocompatible surfactants for water-in-fluorocarbon emulsions. Lab Chip. Oct. 2008;8(10):1632-9. doi: 10.1039/b806706f. Epub Sep. 2, 2008.

Hosokawa, et al. Massively parallel whole genome amplification for single-cell sequencing using droplet microfluidics. Scientific Reports 7, Article No. 5199 (2017).

Hosono S, et al. Unbiased whole-genome amplification directly from clinical samples. Genome Res. May 2003; 13(5):954-64. Epub Apr. 14, 2003.

"How many species of bacteria are there" (wisegeek.com; accessed Jan. 21, 2014).

Hu et al., Shape Controllable Microgel Particles Prepared by Microfluidic Combining External Crosslinking, Biomicrofluidics 6:26502 (May 18, 2012).

Huebner, "Quantitative detection of protein expression in single cells using droplet microfluidics", Chem. Commun. 1218-1220 (2007).

Hug, et al. Measurement of the number of molecules of a single mRNA species in a complex mRNA preparation. J Theor Biol. Apr. 21, 2003;221 (4):615-24.

Illumina Nextera Enrichment Sample Preparation Guide. Feb. 2013.

Illumina TruSeq Custom Enrichment Kit Data Sheet, (c) 2014.

Imburgio, et al., "Studies of promoter recognition and start site selection by T7 RNA polymerase using a comprehensive collection of promoter variants", Biochemistry., 39:10419-30, 2000.

Ioannidis, N. Manufacturing of agarose-based chromatographic adsorbents with controlled pore and particle sizes. A thesis submitted to the University of Birmingham for the degree of Doctor of Philosophy. 2009.

Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.

Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.

JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).

Jung, et al. Micro machining of injection mold inserts for fluidic channel of polymeric biochips. Sensors. 2007; 7(8):1643-1654.

Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.

Kaper, et al. Supporting Information for "Whole-genome haplotyping by dilution, amplification, and sequencing." Proc Natl Acad Sci USA. Apr. 2, 2013;110(14):5552-7. doi: 10.1073/pnas.1218696110. Epub Mar. 18, 2013.

Kaper, et al. Whole-genome haplotyping by dilution, amplification, and sequencing. Proc Natl Acad Sci USA. Apr. 2, 2013;110(14):5552-7. doi: 10.1073/pnas.1218696110. Epub Mar. 18, 2013.

Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.

Katsura, et al. Indirect micromanipulation of single molecules in water-in-oil emulsion. Electrophoresis. Jan. 2001;22(2):289-93.

Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.

Kenis, et al. Microfabrication Inside Capillaries Using Multiphase Laminar Flow Patterning. Science. 1999; 285:83-85.

Khomiakova et al., Analysis of perfect and mismatched DNA duplexes by a generic hexanucleotide microchip. Mol Biol(Mosk). Jul.-Aug. 2003;37(4):726-41. Russian. Abstract only.

Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.

Kim, et al. Fabrication of monodisperse gel shells and functional microgels in microfluidic devices. Angew Chem Int Ed Engl. 2007;46(11):1819-22.

Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.

Kirkness et al. "Sequencing of isolated sperm cells for direct haplotyping of a human genome," Genome Res (2013) 23:826-832.

Kitzman et al. "Haplotype-resolved genome sequencing of a Gujarati Indian individual." Nat Biotechnol (2011) 29:59-63.

Kitzman, et al. Noninvasive whole-genome sequencing of a human fetus. Sci Transl Med. Jun. 6, 2012;4(137): 137ra76. doi: 10.1126/scitranslmed.3004323.

Kivioja, et al. Counting absolute numbers of molecules using unique molecular identifiers. Nat Methods. Nov. 20, 2011;9(1):72-4. doi: 10.1038/nmeth.1778.

Klein, et al. Droplet barcoding for single-cell transcriptomics applied to embryonic stem cells. Cell. May 21, 2015;161 (5):1187-201. doi: 10.1016/j.cell.2015.04.044.

Knapp, et al. Generating barcoded libraries for multiplex high-throughput sequencing. Methods Mol Biol. 2012;840:155-70. doi: 10.1007/978-1-61779-516-9_19.

Knight, et al. Subtle chromosomal rearrangements in children with unexplained mental retardation. Lancet. Nov. 13, 1999;354(9191):1676-81.

Kolodeziejczyk et al., "The technology and biology of single-cell RNA sequencing", Molecular Cell, vol. 58 (May 21, 2015).

Korlach et al., Methods in Enzymology, Real-Time DNA Sequencing from Single Polymerase Molecules, (2010) 472:431-455.

Koster et al., "Drop-based microfluidic devices for encapsulation of single cells", Lab on a Chip the Royal Soc. of Chem. 8:1110-1115 (2008).

Kozarewa, et al., "96-plex molecular barcoding for the Illumina Genome Analyzer", Methods Mol Biol., 733:279-98, 2011.

Kozarewa, et al. "Amplification-free Illumina sequencing-library preparation facilitates improved mapping and assembly of GC-biased genomes", Nat Methods., 6: 291-5, 2009.

Kutyavin, et al. Oligonucleotides containing 2-aminoadenine and 2-thiothymine act as selectively binding complementary agents. Biochemistry. Aug. 27, 1996;35(34):11170-6.

Kwok, et al., "Single-molecule analysis for molecular haplotyping", Hum Mutat., 23:442-6, 2004.

Lagally, et al. Single-Molecular DNA Amplification and Analysis in an Integrated Microfluidic Device. Anal Chem. Feb. 1, 2001;73(3):565-70.

Lagus, et al. A review of the theory, methods and recent applications of high-throughput single-cell droplet microfluidics. J. Phys. D: Appl. Phys. (2013) 46:114005. (21 pages).

Lai; et al., ""Characterization and Use of Laser-Based Lysis for Cell Analysis On-Chip", Journal of the Royal Society, Interface, vol. 5, Supplement 2, pages S113-S121, Oct. 2008, (Year:2008)", Journal of the Royal Society, Interface, Oct. 2008, vol. 5, Supplement 2, S113-S121.

Laird et al., Hairpin-bisulfite PCR: Assessing epigenetic methylation patterns on complementary strands of individual DNA molecules, 2004, PNAS, 101, 204-209.

Lake, et al. "Integrative Single-Cell Analysis by Transcriptional and Epigenetic States in Human Adult Brain". Apr. 19, 2017. doi: https://doi.org/10.1101/128520.

(56) References Cited

OTHER PUBLICATIONS

Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lander, et al. Initial sequencing and analysis of the human genome. Nature, 409 (Feb. 15, 2001): 860-921.
Lasken, et al. (1996) Archaebacterial DNA Polymerases Tightly Bind Uracil-containing DNA. The Journal of Biological Chemistry, 271 (30):17692-17696 (Year: 1996).
Lebedev, A. et al. "Hot Start PCR with heat-activatable primers: a novel approach for improved PCR performance" NAR (2008) 36(20):E131-1.
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Highly multiplexed subcellular RNA sequencing in situ. Science. Mar. 21, 2014;343(6177):1360-3. doi: 10.1126/science.1250212. Epub Feb. 27, 2014."
Lee, J-H. et al. "Fluorescent in situ sequencing (FISSEQ) of RNA for gene expression profiling in intact cells and tissues" Nature Protocols (Feb. 12, 2015) 10(3):442-458.
Lennon; et al., "Lennon et al. A scalable, fully automated process for construction of sequence-ready barcoded libraries for 454. Genome Biology 11:R15 (2010)."
Li, et al. A single-cell-based platform for copy number variation profiling through digital counting of amplified genomic DNA fragments. ACS Appl Mater Interfaces. Mar. 24, 2017. doi: 10.1021/acsami.7b03146. [Epub ahead of print].
Li, Y., et al., "PEGylated PLGA Nanoparticles as protein carriers: synthesis, preparation and biodistribution in rats," Journal of Controlled Release, vol. 71, pp. 203-211 (2001).
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
"List of sequenced bacterial genomes" (Wikipedia.com; accessed Jan. 24, 2014).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lo, et al. On the design of clone-based haplotyping. Genome Biol. 2013;14(9):R100.
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Lundin, et al., "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):S43-7.
Macaulay; et al., "G&T-seq: parallel sequencing of single-cell genomes and transcriptomes. Nature Methods, 2015, p. 1-7."
Macaulay, et al. Single-Cell Multiomics: Multiple Measurements from Single Cells. Trends in Genetics 33.2 (2017): 155-168. PMC. Web. Dec. 18, 2017.
Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10): 1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Man. Monolithic Structures for Integrated Microfluidic Analysis. PhD Thesis. 2001.
Marcus. Gene method offers diagnostic hope. The Wall Street Journal. Jul. 11, 2012.
Margulies 2005 Supplementary methods (Year: 2005).
Margulies et al. "Genome sequencing in microfabricated high-density picoliter reactors", Nature (2005) 437:376-380.
Maricic T, et al. Optimization of 454 sequencing library preparation from small amounts of DNA permits sequence determination of both DNA strands. Biotechniques. Jan. 2009; 46(1):51-2, 54-7.
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis, et al. Selective droplet coalescence using microfluidic systems. Lab Chip. Apr. 24, 2012;12(10):1800-6. doi: 10.1039/c2lc40121e. Epub Mar. 27, 2012.
McGinnis, et al. MULTI-seq: Scalable sample multiplexing for single-cell RNA sequencing using lipid-tagged indices. bioRxiv 387241; doi: https://doi.org/10.1101/387241.
Merriman, et al. Progress in ion torrent semiconductor chip based sequencing. Electrophoresis. Dec. 2012;33(23):3397-417. doi: 10.1002/elps.201200424.
"Meyer, et al., From micrograms to picograms: quantitative PCR reduces the material demands of high-throughput sequencing, Nucleic Acids Research, 2008, vol. 36, No. 1, 6 pages".
Microfluidic ChipShop. Microfluidic product catalogue. Mar. 2005.
Microfluidic ChipShop. Microfluidic product catalogue. Oct. 2009.
Miller JC, et al. An improved zinc-finger nuclease architecture for highly specific genome editing. Nat. Biotechnol. 2007;25:778-785.
Miller-Stephenson Chemicals 157 FS Series catalog, www.miller-stephenon.com.
MiRNA (http://www.exiqon.com/what-are-microRNAs) accessed Oct. 19, 2017.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three-dimensional printing. Microfluidics and Nanofluidics. 2011; 10(4):877-888.
Morgan, et al. Chapter 12: Human microbiome analysis. PLoS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Mouritzen et al., Single nucleotide polymorphism genotyping using locked nucleic acid (LNa). Expert Rev Mol Diagn. Jan. 2003;3(1):27-38.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Narayanan, J. et al. "Determination of agarose gel pore size: Absorbance measurements vis a vis other techniques" Journal of Physics: Conference Series 28 (2006) 83-86 (Year: 2006).

(56) References Cited

OTHER PUBLICATIONS

Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995;21:111-119.
Nisisako, et al. Droplet formation in a microchannel network. Lab Chip. Feb. 2002;2(1):24-6. Epub Jan. 18, 2002.
Nisisako, T. et al. "Droplet Formation in a Microchannel on PMMA Plate" Abstract. 2001 Kluwer Academic Publishers. p. 137-138.
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al,. "Controlled Production ofMonodisperse Double Emulsions by Two-Step Droplet Breakup in Microfluidic Devices," Langmuir, vol. 20, pp. 9905-9908 (2004).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al., "Optimizing Illumina next-generation sequencing library preparation for extremely AT-biased genomes", BMC Genomics. ,13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perrott, Jimmy. Optimization and Improvement of Emulsion PCR for the Ion Torrent Next-Generation Sequencing Platform. (2011) Thesis.
Peters, B.A. et al. Accurate whole-genome sequencing and haplotyping from 10 to 20 human cells. Nature, 487(7406):190-195 (Jul. 11, 2012).
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
Plunkett, et al. Chymotrypsin responsive hydrogel: application of a disulfide exchange protocol for the preparation of methacrylamide containing peptides. Biomacromolecules. Mar.-Apr 2005;6(2):632-7.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015; 16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".

Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramsey, J.M. "The burgeoning power of the shrinking laboratory" Nature Biotech (1999) 17:1061-1062.
Ramskold et al. (2012) "Full-length mRNA-Seq from single-cell levels of RNA and individual circulating tumor cells" Nature Biotechnology 30(8):777-782.
Ran et al. Genome engineering using the CRISPR-Cas9 system. Nature Protocols 8:2281-2308 (2013).
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al., "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 Using MultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005UsingMultiplexIdentifierAdaptorsForTheGSFLXTitaniumChemistry-ExtendedMIDSet.pdf.
Rodrigue, S et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81 (2):199-207. Epub Jun. 29, 2007.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Ryan, "Rapid assay for mycobacterial growth and antibiotic susceptibility using gel microdrop and encapsulation", J. Clinical Microbial., 33:7 1720-1726 (1995).
Sakaguchi, et al. (1996) Cautionary Note on the Use of dUMP-Containing PCR Primers with Pfu and VentR. Biotechniques, 21(3): 369-370 (Year: 1996).
Sander JD, et al. Selection-free zinc-finger-nuclease engineering by context-dependent assembly (CoDA). Nat. Methods. 2011;8:67-69.
Savva, et al. The structural basis of specific base-excision repair by uracil-DNA glycosylase. Nature. Feb. 9, 1995;373(6514):487-93.
Schirinzi et al., Combinatorial sequencing-by-hybridization: Analysis of the NF1 gene. Genet Test. 2006 Spring;10(1):8-17.
Schmeider, et al. Fast identification and removal of sequence contamination from genomic and metagenomic datasets. PLoS One. Mar. 9, 2011;6(3):e17288. doi: 10.1371/journal.pone.0017288.

(56) References Cited

OTHER PUBLICATIONS

Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Seiffert, et al. Smart microgel capsules from macromolecular precursors. J Am Chem Soc. May 12, 2010;132(18):6606-9. doi: 10.1021/ja102156h.
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shaikh, et al. A modular microfluidic architecture for integrated biochemical analysis. Proc Natl Acad Sci USA. Jul. 12, 2005;102(28):9745-50. Epub Jun. 28, 2005.
Shimkus, et al. A chemically cleavable biotinylated nucleotide: usefulness in the recovery of protein-DNA complexes from avidin affinity columns. Proc Natl Acad Sci USA. May 1985;82(9):2593-7.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci USA. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet, www.sigma-aldrich.com.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Simon, et al., "Using formaldehyde-assisted isolation of regulatory elements (FAIRE) to isolate active regulatory DNA", Nature Protocols, 2012, 7(2): 256-267.
Skerra. Phosphorothioate primers improve the amplification of DNA sequences by DNA polymerases with proofreading activity. Nucleic Acids Res. Jul. 25, 1992; 20(14):3551-4.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.

Spormann Laboratory, Polymerase Chain Reaction (PCR), Alfred Spormann Laboratory, 2009, 1-3. (Year: 2009).
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tawfik, D.S., et al., "Man-made cell-like compartments for molecular evolution," Nature Biotechnology, vol. 16, pp. 652-656 (1998).
Tayyab, S. et al. "Size exclusion chromatography and size exclusion HPLC of proteins" Biochem Ed, Pergamon, (1991) 19(3):149-152.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey et al., Supplementary Materials, Nature Biotechnology, 2009, 27(11), 1-22.
Thaxton, C.S. et al. "A Bio-Bar-Code Assay Based Upon Dithiothreitol Oligonucleotide Release" Anal Chem (2005) 77:8174-8178.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thermofisher, Protocols, M-270 Streptavidin, ThermoFisherScientific, 2007, 1-5. (Year: 2007).
Thorsen, et al. Dynamic pattern formation in a vesicle-generating microfluidic device. Physical Review Letters. American Physical Society. 2001; 86(18):4163-4166.
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Tonelli, et al. Perfluoropolyether functional oligomers: unusual reactivity in organic chemistry. Journal of fluorine chemistry. 2002; 118(1)"107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Assaying chromosomal inversions by single-molecule haplotyping. Nat Methods. Jun. 2006;3(6):439-45.
Turner, et al., "High-throughput haplotype determination over long distances by haplotype fusion PCR and ligation haplotyping", Nat Protoc., 4:1771-83, 2009.
Turner, et al. Methods for genomic partitioning. Annu Rev Genomics Hum Genet. 2009;10:263-84. doi: 10.1146/annurev-genom-082908-150112. Review.
Ullal et al. Cancer Cell Profiling by Barcoding Allows Multiplexed Protein Analysis in Fine-Needle Aspirates. Sci Transl Med. Jan. 15, 2014; 6(219): 219ra9.
Ushijima et al., Detection and interpretation of altered methylation patterns in cancer cells, 2005, Nature reviews, 5, 223-231.
Van Nieuwerburgh, et al., "Illumina mate-paired DNA sequencing-library preparation using Cre-Lox recombination", Nucleic Acids Res., 40:1-8, 2012.
Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.

(56) References Cited

OTHER PUBLICATIONS

Wang, et al. A novel thermo-induced self-bursting microcapsule with magnetic-targeting property. Chemphyschem. Oct. 5, 2009;10(14):2405-9.
Wang, et al. Digital karyotyping. Proc Natl Acad Sci USA. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled By CombiGEM. PNAS. Mar. 1, 2016, vol. 113, pp. 2544-2549.
Woo, et al. G/C-modified oligodeoxynucleotides with selective complementarity: synthesis and hybridization properties. Nucleic Acids Res. Jul. 1, 1996;24(13):2470-5.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone.0181163. eCollection 2017.
Xia and Whitesides, Soft Lithography, Angew. Chem. Int. Ed. 37:550-575 (1998).
Xia and Whitesides, Soft Lithography, Ann. Rev. Mat. Sci. 28:153-184 (1998).
Xiao, et al., "Determination of haplotypes from single DNA molecules: a method for singlemolecule barcoding", Hum Mutat., 28:913-21,2007.
Yamamoto, et al. Chemical modification of Ce(IV)/EDTA-base artificial restriction DNA cutter for versatile manipulation of double-stranded DNA. Nucleic Acids Research. 2007; 35(7):e53.
Yan, Pu et al. "Rapid one-step construction of hairpin RNA" Biochem and Biophys Res Comm (Jun. 12, 2009) 383(4):464-468.
Zeng, et al. High-performance single cell genetic analysis using microfluidic emulsion generator arrays. Anal Chem. Apr. 15, 2010;82(8):3183-90. doi: 10.1021/ac902683t.
Zentner, et al. Surveying the epigenomic landscape, one base at a time. Genome Biol. Oct. 22, 2012;13(10):250. doi: 10.1186/gb4051.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31.doi: 10.1021/bm800867n. Epub Oct. 9, 2008.
Zhang, et al. One-step fabrication of supramolecular microcapsules from microfluidic droplets. Science. Feb. 10, 2012;335(6069):690-4. doi: 10.1126/science.1215416.
Zhang, et al. Reconstruction of DNA sequencing by hybridization. Bioinformatics. Jan. 2003;19(1):14-21.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online], University of Washington. 2015 [Retrieved on May 3, 2017].
Zhao, J., et al., "Preparation of hemoglobin-loaded Nano-sized particles with porous structure as oxygen carriers," Biomaterials, vol. 28, pp. 1414-1422 (2007).
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Reverse transcriptase template switching: a SMART approach for full-length cDNA library construction. Biotechniques. Apr. 2001;30(4):892-7.
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Huml Antibodies Hybridomas. Jan. 1992;3(1 ): 14-8.
Zong et al. Genome-Wide Detection of Single Nucleotide and Copy Number Variations of a Single Human Cell. Science 338(6114):1622-1626 (2012).
Co-pending U.S. Appl. No. 16/196,684, filed Nov. 20, 2018.
Jin, et al. Genome-wide detection of DNase I hypersensitive sites in single cells and FFPE tissue samples. Nature. Dec. 3, 2015;528(7580):142-6. doi: 10.1038/nature15740.
10X Genomics, Inc. CG000153 Rev A. Chromium Single Cell DNA Reagent Kits User Guide. 2018.
10X Genomics, Inc. CG000184 Rev A. Chromium Single Cell 3' Reagent Kits v3 User Guide with Feature Barcoding Technology for CRISPR Screening. 2018.
10X Genomics, Inc. CG000185 Rev B. Chromium Single Cell 3' Reagent Kits User Guide with Feature Barcoding Technology for Cell Surface Protein. 2018.
10X Genomics, Inc. CG000208 Rev E. Chromium Next GEM Single Cell V(D)J reagent Kits v1.1 User Guide with Feature Barcode Technology for Cell Surface Protein. 2020.
10X Genomics, Inc. CG000209 Rev D. Chromium Next GEM Single Cell ATAC Reagent Kits v1.1 User Guide. 2020.
10X Genomics, Inc. CG000239 Rev B. Visium Spatial Gene Expression Reagent Kits User Guide. 2020.
10X Genomics, Inc. CG00026. Chromium Single Cell 3' Reagent Kit User Guide. 2016.
10X Genomics, Inc. LIT00003 Rev B Chromium Genome Solution Application Note. 2017.
Co-pending U.S. Appl. No. 16/708,214, filed Dec. 9, 2019.
Co-pending U.S. Appl. No. 16/737,762, filed Jan. 8, 2020.
Co-pending U.S. Appl. No. 16/737,770, filed Jan. 8, 2020.
Co-pending U.S. Appl. No. 16/789,273, filed Feb. 12, 2020.
Co-pending U.S. Appl. No. 16/789,287, filed Feb. 12, 2020.
Co-pending U.S. Appl. No. 16/800,450, filed Feb. 25, 2020.
Co-pending U.S. Appl. No. 16/814,908, filed Mar. 10, 2020.
Devor, et at. Strategies for attaching oligonucleotides to solid supports. IDT DNA Rep (2005): 1-24.
Reuter, J.A et al. "Simul-seq: combined DNA and RNA sequencing for whole-genome and transcriptome profiling" Nature Methods (2016) 13(11):953-958.
Steinberg-Tatman, et al. Synthetic modification of silica beads that allows for sequential attachment of two different oligonucleotides. Bioconjugate chemistry 17.3 (2006): 841-848.

(56) References Cited

OTHER PUBLICATIONS

PCT/US2020/017785 Application filed on Feb. 11, 2020 by Ziraldo, Solongo B. et al.
PCT/US2020/017789 Application filed on Feb. 11, 2020 by Belhocine, Zahara Kamila et al.
Co-pending U.S. Appl. No. 16/998,414, filed Aug. 20, 2020.
Co-pending U.S. Appl. No. 16/998,425, filed Aug. 20, 2020.
Bentolila, et al. Single-step multicolor fluorescence in situ hybridization using semiconductor quantum dot-DNA conjugates. Cell Biochem Biophys. 2006;45(1):59-70.
Bystrykh, et al. Generalized DNA barcode design based on Hamming codes. PLoS One. 2012;7(5):e36852. doi: 10.1371/journal.pone.0036852. Epub May 17, 2012.
Co-pending U.S. Appl. No. 16/395,090, filed Apr. 25, 2019.
Co-pending U.S. Appl. No. 16/419,428, filed May 22, 2019.
Co-pending U.S. Appl. No. 16/419,461, filed May 22, 2019.
Co-pending U.S. Appl. No. 16/419,555, filed May 22, 2019.
Co-pending U.S. Appl. No. 16/419,630, filed May 22, 2019.
Co-pending U.S. Appl. No. 16/419,820, filed May 22, 2019.
Co-pending U.S. Appl. No. 16/435,362, filed Jun. 7, 2019.
Co-pending U.S. Appl. No. 16/435,417, filed Jun. 7, 2019.
Definition of "corresponding", Merriam-Webster Online, downloaded from http://www.merriam-webster.com/dictionary/corresponding (Year: 2019).
Dhingra, et al. A complete solution for high throughput single cell targeted multiomic DNA and RNA sequencing for cancer research. Poster. AACR 2019.
Maeda, et al. Development of a DNA barcode tagging method for monitoring dynamic changes in gene expression by using an ultra high-throughput sequencer. Biotechniques. Jul. 2008;45(1):95-7. doi: 10.2144/000112814.
Mamedov, I.Z., et al. (2013), Preparing unbiased T-cell receptor and antibody cDNA libraries for the deep next generation sequencing profiling, Front Immunol 4: 456.
Co-pending U.S. Appl. No. 17/353,202, inventors Hindson; Benjamin et al., filed Jun. 21, 2021.
Co-pending U.S. Appl. No. 17/381,612, inventor Martinez; Luigi Jhon Alvarado, filed Jul. 21, 2021.
Xiong, et al., Responsive DNA-based hydrogels and their applications. Macromol Rapid Commun. Aug. 2013; 34(16): 1271-1283, doi:10.1002/marc.201300411.

\* cited by examiner

PARTITIONING AND PROCESSING OF ANALYTES AND OTHER SPECIES

CROSS-REFERENCE

This application is a continuation of U.S. patent application Ser. No. 15/693,374, filed on Aug. 31, 2017, which is a continuation application of U.S. patent application Ser. No. 15/470,814, filed Mar. 27, 2017, which is a continuation application of U.S. patent application Ser. No. 14/175,935, filed Feb. 7, 2014, now U.S. Pat. No. 9,644,204, which claims the benefit of U.S. Provisional Patent Application No. 61/762,435, filed Feb. 8, 2013, U.S. Provisional Patent Application No. 61/800,223, filed Mar. 15, 2013, U.S. Provisional Patent Application No. 61/840,403, filed Jun. 27, 2013, and U.S. Provisional Patent Application No. 61/844,804, filed Jul. 10, 2013, said applications are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Oct. 25, 2018, is named 43487-705303SL.txt and is 4,650 bytes in size.

BACKGROUND

The partitioning and processing of species such as analytes and reagents is important for a variety of applications, including molecular biology applications and medical applications. Appropriate sample preparation is often needed prior to performing a reaction such as a polynucleotide sequencing reaction or an analyte detection reaction. For example, a sample such as a biological sample, including a collection of cells, tissue, and/or nucleic acids may need to be lysed, fragmented, or otherwise manipulated in order to permit downstream analysis. Sample preparation may also involve isolating certain molecules, and/or attaching unique identifiers to certain molecules, among other processes. There is a need in the art for improved methods, compositions, systems, devices, and kits for partitioning and processing of species.

SUMMARY

This disclosure provides methods, compositions, systems, devices, and kits for partitioning and processing of species. The exemplary embodiments provided in this summary are, in no way, intended to be limiting, and are only provided for illustrative purposes. Other embodiments are disclosed throughout this disclosure.

I. Capsules Within Droplets

In some cases, the disclosure provides compositions comprising a plurality of capsules, the capsules situated within droplets in an emulsion, wherein the capsules are configured to release their contents into the droplets upon the application of a stimulus.

In some cases, the capsules comprise a species selected from the group consisting of a reagent and an analyte. In some cases, the droplets comprise a species selected from the group consisting of a reagent and an analyte.

In some cases a reagent is a protein, a polynucleotide, an enzyme, an antibody, a barcode, an adapter, a buffer, a small molecule, a detergent, a dye, a polymer and combinations thereof. In some cases, a reagent is an enzyme selected from the group consisting of a proteinase, a restriction enzyme, a ligase, a polymerase, a fragmentase, a reverse transcriptase, a transposase, and combinations thereof. In some cases an enzyme is a restriction enzyme that is a rare cutter. A reagent that is a barcode may be, for example, an oligonucleotide barcode.

An analyte may be any suitable analyte, for example a cell, a polynucleotide, a chromosome, a protein, a peptide, a polysaccharide, a sugar, a lipid, a small molecule, and combinations thereof. In some cases, an analyte is a polynucleotide. In some cases, the polynucleotide is selected from the group consisting of DNA, RNA, cDNA, and combinations thereof. In some cases, the amount of polynucleotide in a composition disclosed herein is about 1-3 ng. In some cases, the amount of polynucleotide in a composition disclosed herein is an amount sufficient to provide about 100-200× sequence coverage.

In some cases, a capsule may comprise on average, about one chromosome per capsule.

In some cases, each droplet may comprise, on average, about 1 capsule per droplet. In some cases, each droplet can hold, at most, a single capsule.

In some cases, at least one of the capsules comprises a further partition. The further partition may be, for example, selected from the group consisting of a capsule and a droplet in an emulsion.

In some cases, at least one of the capsules has a shell selected from the group consisting of a polymeric shell, a hydrogel, a hydrophilic shell, a hydrophobic shell, a shell with a net positive charge, a shell with a net negative charge, a shell with a neutral charge, and combinations thereof. In some cases, a capsule is formed from a hydrogel droplet.

In some cases, a capsule is responsive to a stimulus is selected from the group consisting of a chemical stimulus, a bulk stimulus, a biological stimulus, a light stimulus, a thermal stimulus, a magnetic stimulus, and combinations thereof. In some cases, a thermal stimulus comprises causing the composition to reach a temperature of at least 32 degrees Celsius. In some cases, the stimulus is selected from the group consisting of a change in pH, a change in ion concentration, reduction of disulfide bonds, and combinations thereof.

In some cases, capsules have a mean diameter of 1 micron to 250 microns, 1 micron to 100 microns, 1 micron to 50 microns, 10 microns to 100 microns, or 50 microns to 100 microns. In some cases droplets have a mean diameter of about 1 micron to about 250 microns, 1 micron to 100 microns, 1 micron to 50 microns, 10 microns to 100 microns, or 50 microns to 100 microns.

In some cases capsules have a mean volume of 1 picoliter to 1 microliter, 1 picoliter to 0.5 microliters, 1 picoliter to 0.1 microliters, 100 picoliters to 0.1 microliters, or 100 nanoliters to 500 nanoliters. In some cases droplets have a mean volume of about 1 picoliter to about 1 microliter, 1 picoliter to 0.5 microliters, 1 picoliter to 0.1 microliters, 100 picoliters to 0.1 microliters, or 100 nanoliters to 500 nanoliters.

In some cases the droplets comprise a fluid that is of a lesser density than the density of the capsules. In some cases the droplets comprise a fluid that is of a greater density than the density of the capsules.

In some cases capsules are produced by a method selected from the group consisting of emulsification polymerization, layer-by-layer assembly with polyelectrolytes, coacervation, internal phase separation, flow focusing, and combinations thereof.

In some cases a stimulus is applied to the capsules. In some cases a stimulus is applied to the droplets.

II. Capsules in Capsules

In some cases this disclosure provides compositions comprising a plurality of outer capsules, the outer capsules comprising at least one inner capsule, wherein the at least one inner capsule is configured to release its contents into at least one outer capsule among the plurality of outer capsules upon the application of a stimulus.

In some cases the inner capsule comprises a species selected from the group consisting of a reagent and an analyte. In some cases the outer capsules comprise a species selected from the group consisting of a reagent and an analyte.

In some cases the reagent is selected from the group consisting of a protein, a polynucleotide, an enzyme, an antibody, a barcode, an adapter, a buffer, a small molecule, a detergent, a dye, a polymer and combinations thereof. In some cases an enzyme is selected from the group consisting of a proteinase, a restriction enzyme, a ligase, a polymerase, a fragmentase, a reverse transcriptase, a transposase, and combinations thereof. In some cases the restriction enzyme is a restriction enzyme that is a rare cutter. In some cases the reagent is a barcode that is an oligonucleotide barcode.

In some cases the analyte is selected from the group consisting of a cell, a polynucleotide, a chromosome, a protein, a peptide, a polysaccharide, a sugar, a lipid, a small molecule, and combinations thereof. In some cases the analyte is a polynucleotide. In some cases the polynucleotide is selected from the group consisting of DNA, RNA, cDNA, and combinations thereof. In some cases the amount of the polynucleotide in a composition of this disclosure is about 1-3 ng. In some cases the amount of the polynucleotide in a composition of this disclosure is an amount sufficient to provide about 100-200× sequence coverage.

In some cases capsule comprises, on average, about one chromosome. In some cases each outer capsule comprises, on average, about 1 inner capsule per outer capsule. In some cases each outer capsule can hold, at most, a single inner capsule.

In some cases at least one inner capsule comprises a further partition. In some cases, the further partition is selected from the group consisting of a capsule and a droplet in an emulsion.

In some cases a capsule has a shell selected from the group consisting of a polymeric shell, a hydrogel, a hydrophilic shell, a hydrophobic shell, a shell with a net positive charge, a shell with a net negative charge, a shell with a neutral charge, and combinations thereof.

In some cases a capsule is responsive to a stimulus is selected from the group consisting of a chemical stimulus, a bulk stimulus, a biological stimulus, a light stimulus, a thermal stimulus, a magnetic stimulus, and combinations thereof. In some cases the thermal stimulus comprises causing the composition to reach a temperature of at least 32 degrees Celsius. In some cases the stimulus is selected from the group consisting of a change in pH, a change in ion concentration, reduction of disulfide bonds, and combinations thereof.

In some cases the inner capsules have a mean diameter of 1 micron to 250 microns, 1 micron to 100 microns, 1 micron to 50 microns, 10 microns to 100 microns, or 50 microns to 100 microns. In some cases the outer capsules have a mean diameter of 1 micron to 250 microns, 1 micron to 100 microns, 1 micron to 50 microns, 10 microns to 100 microns, or 50 microns to 100 microns.

In some cases the inner capsules have a mean volume of 1 picoliter to 1 microliter, 1 picoliter to 0.5 microliters, 1 picoliter to 0.1 microliters, 100 picoliters to 0.1 microliters, or 100 nanoliters to 500 nanoliters. In some cases the outer capsules have a mean volume of 1 picoliter to 1 microliter, 1 picoliter to 0.5 microliters, 1 picoliter to 0.1 microliters, 100 picoliters to 0.1 microliters, or 100 nanoliters to 500 nanoliters.

In some cases the outer capsules comprise a fluid that is of a lesser density than the density of the inner capsules. In some cases the outer capsules comprise a fluid that is of a greater density than the density of the inner capsules.

In some cases the capsules are produced by a method selected from the group consisting of emulsification polymerization, layer-by-layer assembly with polyelectrolytes, coacervation, internal phase separation, flow focusing, and combinations thereof.

In some cases the stimulus is applied to the inner capsule. In some cases the stimulus is applied to the outer capsule.

III. Spots in Wells

In some cases this disclosure provides a composition comprising a plurality of discrete spots disposed on a surface within a well, wherein each spot comprises a species and the spots are configured to release the species upon application of a stimulus. In some cases the species is selected from the group consisting of a reagent and an analyte. In some cases a composition of this disclosure further comprises a medium, wherein the medium comprises a species selected from the group consisting of a reagent and an analyte.

In some cases the reagent is selected from the group consisting of a protein, a polynucleotide, an enzyme, an antibody, a barcode, an adapter, a buffer, a small molecule, a detergent, a dye, a polymer and combinations thereof. In some cases the enzyme is selected from the group consisting of a proteinase, a restriction enzyme, a ligase, a polymerase, a fragmentase, a reverse transcriptase, a transposase, and combinations thereof. In some cases the restriction enzyme is a restriction enzyme that is a rare cutter. In some cases the barcode is an oligonucleotide barcode.

In some cases the analyte is selected from the group consisting of a cell, a polynucleotide, a chromosome, a protein, a peptide, a polysaccharide, a sugar, a lipid, a small molecule, and combinations thereof. In some cases the analyte is a polynucleotide. In some cases polynucleotide is selected from the group consisting of DNA, RNA, cDNA, and combinations thereof. In some cases the amount of the polynucleotide in the composition is about 1-3 ng. In some cases the amount of the polynucleotide in a composition of this disclosure is an amount sufficient to provide about 100-200× sequence coverage.

In some cases each well comprises at least 4 spots. In some cases at least one of the spots comprises a further partition. In some cases the further partition is selected from the group consisting of a capsule and a droplet in an emulsion.

In some cases the stimulus that releases a species from a spot is the introduction of a medium comprising an analyte into the well.

In some cases the spots have a mean diameter of about 1 micron to about 250 microns, 1 micron to 150 microns, 1

IV. Devices Comprising Capsules in Droplets

In some cases this disclosure provides devices comprising a plurality of partitions, wherein at least one partition of the plurality of partitions comprises a capsule, wherein the capsule is situated within a droplet in an emulsion, wherein the capsule is configured to release its contents into the droplet upon the application of a stimulus. In some cases the plurality of partitions are selected from the group consisting of wells and spots.

In some cases the device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases the device comprises at least 1,000 partitions. In some cases the partitions have a density selected from the group consisting of at least about 1,000 partitions/$cm^2$ and at least about 10,000 partitions/$cm^2$.

In some cases the partitions are disposed along a fluid flow path having a fluid inlet and a fluid outlet.

In some cases the partitions are wells are disposed within a glass slide. In some cases the partitions are spots disposed on a glass slide.

In some cases the partitions have an interior surface comprising a hydrophilic material. In some cases a surface exterior to the partitions comprises a hydrophobic material. In some cases a fluid flow path comprises a surface comprising a hydrophobic material.

IV. Devices Comprising Capsules in Capsules

In some cases this disclosure provides devices comprising a plurality of partitions, wherein at least one partition of the plurality of partitions comprises an outer capsule, the outer capsule comprising at least one inner capsule, wherein the at least one inner capsule is configured to release its contents into the outer capsule upon the application of a stimulus. In some cases the plurality of partitions are selected from the group consisting of wells and spots.

In some cases the device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases the device comprises at least 1,000 partitions. In some cases the partitions have a density selected from the group consisting of at least about 1,000 partitions/$cm^2$ and at least about 10,000 partitions/$cm^2$.

In some cases the partitions are disposed along a fluid flow path having a fluid inlet and a fluid outlet.

In some cases the partitions are wells are disposed within a glass slide. In some cases the partitions are spots disposed on a glass slide.

In some cases the partitions have an interior surface comprising a hydrophilic material. In some cases a surface exterior to the partitions comprises a hydrophobic material. In some cases the fluid flow path comprises a surface comprising a hydrophobic material.

IV. Devices Comprising Spots in Wells

In some cases this disclosure provides devices comprising a plurality of wells, wherein at least one well of the plurality of wells comprises a plurality of discrete spots disposed on a surface within the well, wherein each spot comprises a species and the spots are configured to release the species upon application of a stimulus.

In some cases the device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases the device comprises at least 1,000 wells. In some cases the wells have a density selected from the group consisting of at least about 1,000 wells/$cm^2$ and at least about 10,000 wells/$cm^2$.

In some cases the wells are disposed along a fluid flow path having a fluid inlet and a fluid outlet.

In some cases the wells are disposed within a glass slide. In some cases the spots are disposed on a glass slide.

In some cases the wells have an interior surface comprising a hydrophilic material. In some cases a surface exterior to the wells comprises a hydrophobic material. In some cases the fluid flow path comprises a surface comprising a hydrophobic material.

IV. Methods Utilizing Capsules in Droplets

In some cases this disclosure provides a method comprising: (a) providing a plurality of capsules, the capsules situated within droplets in an emulsion, wherein the capsules are configured to release their contents into the droplets upon the application of a stimulus; and (b) providing a stimulus to cause the capsules to release their contents into the droplets.

In some cases the capsules comprise a species selected from the group consisting of a reagent and an analyte. In some cases the droplets comprise a species selected from the group consisting of a reagent and an analyte.

In some cases causing the capsules to release their contents into the droplets results in contact between a polynucleotide and an enzyme. In some cases causing the capsules to release their contents into the droplets results in contact between a polynucleotide and a barcode.

In some cases the analyte is a polynucleotide present in a predetermined coverage amount.

In some cases the method further comprises the step of sequencing the polynucleotide. In some cases the method further comprises the step of performing a polynucleotide phasing analysis.

V. Methods Utilizing Capsules in Capsules

In some cases this disclosure provides a method comprising: (a) providing a plurality of inner capsules, the inner capsules situated within outer capsules, wherein the inner capsules are configured to release their contents into the outer capsules upon the application of a stimulus; and (b) providing a stimulus to cause the inner capsules to release their contents into the outer capsules.

In some cases the inner capsules comprise a species selected from the group consisting of a reagent and an analyte. In some cases the outer capsules comprise a species selected from the group consisting of a reagent and an analyte.

In some cases causing the inner capsules to release their contents into the outer capsules results in contact between a polynucleotide and an enzyme. In some cases causing the inner capsules to release their contents into the outer capsules results in contact between a polynucleotide and a barcode.

In some cases the analyte is a polynucleotide present in a predetermined coverage amount.

In some cases the method further comprises the step of sequencing the polynucleotide. In some cases the method further comprises the step of performing a polynucleotide phasing analysis.

VI. Methods Utilizing Spots in Wells

In some cases this disclosure provides a method comprising: (a) providing a well comprising a plurality of discrete spots disposed on a surface within the well, wherein each spot comprises a species and the spots are configured to release the species upon application of a stimulus; (b) adding a medium comprising a species to the well; and (c) providing a stimulus to cause the spots to release their contents into the well.

In some cases the spots comprise a species selected from the group consisting of a reagent and an analyte. In some cases the medium comprises a species selected from the group consisting of a reagent and an analyte.

In some cases causing the spots to release their contents into the well results in contact between a polynucleotide and an enzyme. In some cases causing the spots to release their contents into the well results in contact between a polynucleotide and a barcode.

In some cases the analyte is a polynucleotide present in a predetermined coverage amount.

In some cases the method further comprises the step of sequencing the polynucleotide. In some cases the method further comprises the step of performing a polynucleotide phasing analysis.

VI. Methods of Encapsulating Polynucleotides, Including Whole Chromosomes

In some cases this disclosure provides a method comprising: (a) providing a sample comprising a cell; (b) lysing the cell, thereby generating a lysate; and (c) partitioning the lysate into a capsule.

In some cases the sample comprises a plurality of cells. In some cases the plurality of cells comprises 1 to 100,000 cells, 10 to 10,000 cells, 100 to 5,000 cells, or 1,000 to 5,000 cells.

In some cases lysing comprises a treatment with a proteinase. In some cases the proteinase is proteinase K.

In some cases after the partitioning, at least one of the capsules comprises a single copy of a polynucleotide from the cell. In some cases, at least one capsule comprises a mixture of polynucleotides, wherein none of the polynucleotides in the mixture are overlapping.

In some cases the polynucleotide is a chromosome.

In some cases the capsule comprises a shell with pores that restrict trans-shell transport of the polynucleotide but allow trans-shell transport of a species. In some cases the method further comprises the step of transporting an inner species from the interior of the capsule to the exterior of the capsule. In some cases the inner species is selected from the group consisting of a component of a buffer, a component of a cell, and a macromolecule. In some cases the method further comprises the step of transporting an outer species from the exterior of the capsule to the interior of the capsule. In some cases the outer species is selected from the group consisting of a reagent, a protein, a polynucleotide, an enzyme, an antibody, a barcode, an adapter, a buffer, a small molecule, a detergent, a dye, a polymer and combinations thereof. In some cases the outer species is a reagent for nucleic acid amplification.

In some cases the method further comprises the step of amplifying the encapsulated polynucleotide. In some cases the amplifying is performed by a method selected from the group consisting of multiple displacement amplification, polymerase chain reaction, ligase chain reaction, helicase-dependent amplification, and combinations thereof.

In some cases the method further comprises the step of fragmenting the encapsulated polynucleotide, thereby generating a fragmented polynucleotide. In some cases the method further comprises the step of attaching a barcode to the fragmented polynucleotide.

In some cases the method further comprises the step of placing the capsule comprising polynucleotide (or processed polynucleotide) into a partition. In some cases the partition is selected from the group consisting of a well, a droplet in an emulsion, and a capsule.

In some cases the capsule comprising the polynucleotide is configured to release its contents upon the application of a stimulus. In some cases the stimulus is selected from the group consisting of a chemical stimulus, a bulk stimulus, a biological stimulus, a light stimulus, a thermal stimulus, a magnetic stimulus, and combinations thereof.

In some cases the method further comprises the step of performing a polynucleotide phasing analysis.

VII. Kits

In some cases this disclosure provides kits. In some cases the disclosure provides kits for generating capsules within droplets in an emulsion, the kits comprising reagents for generating capsules, reagents for generating an emulsion, and instructions for generating the capsules within droplets in an emulsion. In some cases the capsules are configured to release their contents into the droplets upon the application of a stimulus. In some cases the kits further comprise a species for inclusion in a partition selected from the group consisting of the capsules, the droplets, and combinations thereof.

In some cases, this disclosure provides kits for generating capsules within capsules, the kits comprising reagents for generating inner capsules, reagents for generating outer capsules, and instructions for generating capsules within capsules. In some cases the inner capsules are configured to release their contents into the outer capsules upon the application of a stimulus. In some cases, the kits further comprise a species for inclusion in a partition selected from the group consisting of the inner capsules, the outer capsules, and combinations thereof.

In some cases this disclosure provides kits comprising a plurality of discrete spots disposed on a surface within a well, wherein each spot comprises a species and the spots are configured to release the species upon application of a stimulus, and instructions for use of the kit to process a sample. In some cases the stimulus is the addition of a sample to the well.

VIII. Partitioning and Fragmenting Methods

In some cases this disclosure provides a method of partitioning polynucleotides comprising: (a) isolating polynucleotides from a source of polynucleotides; (b) partitioning the polynucleotides at a predetermined coverage amount, to produce a plurality of partitions, wherein at least one partition comprises a mixture of non-overlapping polynucleotides, thereby generating partitioned polynucleotides; and (c) fragmenting the partitioned polynucleotides, thereby generating fragmented polynucleotides.

In some cases the source is a cell.

In some cases at least about 50% of the partitions comprise a mixture of non-overlapping polynucleotides.

In some cases the method further comprises the step of amplifying the partitioned polynucleotides. In some cases, the method further comprises the step of barcoding the fragmented polynucleotides.

In some cases this disclosure provides a method of fragmenting a polynucleotide comprising: (a) providing a polynucleotide; (b) encapsulating the polynucleotide, thereby generating an encapsulated polynucleotide; and (c) fragmenting the polynucleotide, thereby generating an encapsulated fragmented polynucleotide.

In some cases the fragmenting is performed by ultrasonic waves.

In some cases the encapsulating disposes the polynucleotide within a capsule. In some cases the encapsulating disposes the polynucleotide within a droplet of a hydrogel.

In some cases the method further comprises the step of encapsulating the encapsulated polynucleotide within a capsule. In some cases the method further comprises the step of encapsulating the encapsulated polynucleotide within a droplet of a hydrogel.

An additional aspect of the disclosure provides the use of a composition, device, method, or kit described herein in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, in circulating tumor cell (CTC) sequencing, in polynucleotide phasing, in sequencing polynucleotides from small numbers of cells, in analyzing gene expression, in partitioning polynucleotides from cells, or in a combination thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of methods, compositions, systems, and devices of this disclosure are set forth with particularity in the appended claims. A better understanding of the features and advantages of this disclosure will be obtained by reference to the following detailed description that sets forth illustrative embodiments, in which the principles of the methods, compositions, systems, and devices of this disclosure are utilized, and the accompanying drawings of which:

DETAILED DESCRIPTION

Figure 1A:
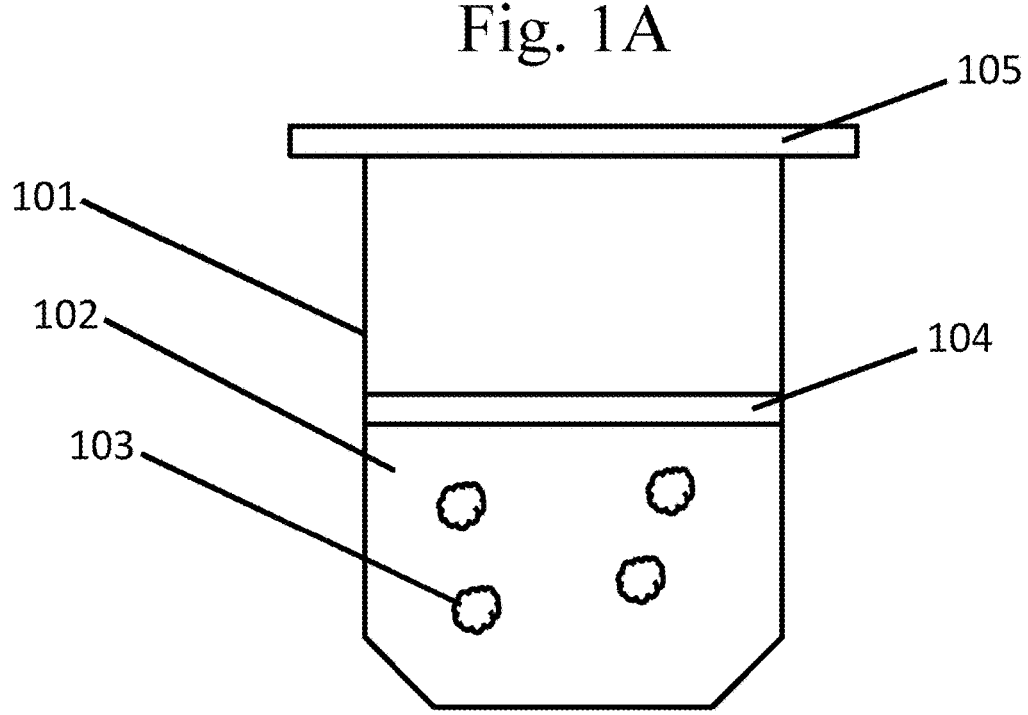
FIGS. 1A-B are schematic examples of wells comprising other types of partitions.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

This disclosure provides methods, compositions, systems, devices, and kits for partitioning and processing of species. A species may be contained within a sample that may also comprise other species. The sample may be partitioned. A sample may comprise any suitable species, as described more fully elsewhere in this disclosure. In some cases, a sample comprises a species that is a reagent or an analyte. The methods, compositions, systems, devices, and kits may be used for a variety of applications. Analyte may be processed for any suitable application, including, for example, processing polynucleotides for polynucleotide sequencing. Polynucleotides sequencing includes the sequencing of whole genomes, detection of specific sequences such as single nucleotide polymorphisms (SNPs) and other mutations, detection of nucleic acid (e.g., deoxyribonucleic acid) insertions, and detection of nucleic acid deletions.

Utilization of the methods, compositions, systems, devices, and kits described herein may incorporate, unless otherwise indicated, any conventional techniques of organic chemistry, polymer technology, microfluidics, molecular biology, recombinant techniques, cell biology, biochemistry, and immunology. Such conventional techniques include well and microwell construction, capsule generation, generation of emulsions, spotting, microfluidic device construction, polymer chemistry, restriction digestion, ligation, cloning, polynucleotide sequencing, and polynucleotide sequence assembly. Specific, non-limiting, illustrations of suitable techniques are described throughout this disclosure. However, equivalent procedures may also be utilized. Descriptions of certain techniques may be found in standard laboratory manuals, such as *Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), and "Oligonucleotide Synthesis: A Practical Approach" 1984, IRL Press London, all of which are herein incorporated in their entirety by reference for all purposes.

I. Definitions

The terminology used herein is for the purpose of describing particular embodiments only and is not intended to be limiting.

As used herein, the singular forms "a," "an," and "the" are intended to include the plural forms as well, unless the context clearly indicates otherwise. Furthermore, to the extent that the terms "including," "includes," "having," "has," "with," "such as," or variants thereof, are used in either the specification and/or the claims, such terms are not limiting and are intended to be inclusive in a manner similar to the term "comprising".

The term "about," as used herein, generally refers to a range that is 15% greater than or less than a stated numerical value within the context of the particular usage. For example, "about 10" would include a range from 8.5 to 11.5.

The term "barcode," as used herein, generally refers to a label that may be attached to an analyte to convey information about the analyte. For example, a barcode may be a polynucleotide sequence attached to all fragments of a target polynucleotide contained within a particular partition. This barcode may then be sequenced with the fragments of the target polynucleotide. The presence of the same barcode on multiple sequences may provide information about the origin of the sequence. For example, a barcode may indicate that the sequence came from a particular partition and/or a proximal region of a genome. This may be particularly useful when several partitions are pooled before sequencing.

The term "bp," as used herein, generally refers to an abbreviation for "base pairs".

The term "microwell," as used herein, generally refers to a well with a volume of less than 1 mL. Microwells may be made in various volumes, depending on the application. For example, microwells may be made in a size appropriate to accommodate any of the partition volumes described herein.

The term "partition," as used herein, may be a verb or a noun. When used as a verb (e.g., "to partition," or "partitioning"), the term generally refers to the fractionation (subdivision) of a species or sample (e.g., a polynucleotide) between vessels that can be used to sequester one fraction (or subdivision) from another. Such vessels are referred to using the noun "partition." Partitioning may be performed, for example, using microfluidics, dilution, dispensing, and the like. A partition may be, for example, a well, a microwell, a hole, a droplet (e.g., a droplet in an emulsion), a continuous phase of an emulsion, a test tube, a spot, a capsule, or any other suitable container for sequestering one fraction of a sample from another.

The terms "polynucleotide" or "nucleic acid," as used herein, generally refer to molecules comprising a plurality of nucleotides. Exemplary polynucleotides include deoxyribonucleic acids, ribonucleic acids, and synthetic analogues thereof, including peptide nucleic acids.

The term "species," as used herein, generally refers to any substance that can be used with the methods, compositions, systems, devices, and kits of this disclosure. Examples of species include reagents, analytes, cells, chromosomes, tagging molecules or groups of molecules, barcodes, and any sample comprising any of these species. Any suitable species may be used, as more fully discussed elsewhere in this disclosure.

II. Partitions a. General Characteristics of Partitions

As described throughout this disclosure, certain methods, compositions, systems, devices, and kits of the disclosure may utilize the subdivision (partitioning) of certain species into separate partitions. A partition may be, for example, a well, a microwell, a hole, a droplet (e.g., a droplet in an emulsion), a continuous phase of an emulsion, a test tube, a spot, a bead (e.g., a gel bead, a paraffin bead, a wax bead), a capsule, or any other suitable container for sequestering one fraction of a sample or a species. In some cases, a capsule is a bead (e.g., a gel bead). Partitions may be used to contain a species for further processing. For example, if a species is a polynucleotide analyte, further processing may comprise cutting, ligating, and/or barcoding with species that are reagents. Any number of devices, systems or containers may be used to hold, support or contain partitions. In some cases, a microwell plate may be used to hold, support, or contain partitions. Any suitable microwell plate may be used, for example microwell plates having 96, 384, or 1536 wells.

Each partition may also contain, or be contained within any other suitable partition. For example, a well, microwell, hole, or tube may comprise a droplet (e.g., a droplet in an emulsion), a continuous phase in an emulsion, a spot, a capsule, or any other suitable partition. A droplet may comprise a capsule or another droplet. A capsule may comprise a droplet or another capsule. These descriptions are merely illustrative, and all suitable combinations and pluralities are also envisioned. For example, any suitable partition may comprise a plurality of the same or different partitions. In one example, a well or microwell comprises a plurality of droplets and a plurality of capsules. In another example, a capsule comprises a plurality of capsules and a plurality of droplets. All combinations of partitions are envisioned. Table 1 shows non-limiting examples of partitions that may be combined with each other.

TABLE 1

Examples of partitions that may be combined with each other.

| | Well | Spot | Droplet | Capsule |
|---|---|---|---|---|
| Well | Well inside well | Spot inside well | Droplet inside well | Capsule inside well |
| Spot | Spot inside well | Spot inside spot | Droplet inside spot | Capsule inside spot |
| Droplet | Droplet inside well | Droplet inside spot | Droplet inside droplet | Droplet inside capsule<br>Capsule inside droplet |
| Capsule | Capsule inside well | Capsule inside spot<br>Spot inside capsule | Capsule inside droplet<br>Droplet inside capsule | Capsule inside capsule |

Any partition described herein may comprise multiple partitions. For example, a partition may comprise 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. A partition may comprise at least 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, a partition may comprise less than 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, or 50000 partitions. In some cases, each partition may comprise 2-50, 2-20, 2-10, or 2-5 partitions.

A partition may comprise any suitable species or mixture of species. For example, in some cases a partition may comprise a reagent, an analyte, a sample, a cell, and combinations thereof. A partition comprising other partitions may comprise certain species in the same partitions and certain species in different partitions. Species may be distributed between any suitable partitions, depending on the needs of the particular process. For example, any of the partitions in Table 1 may contain at least one first species and any of the partitions in Table 1 may contain at least one second species. In some cases the first species may be a reagent and the second species may be an analyte.

In some cases, a species is a polynucleotide isolated from a cell. For example, in some cases polynucleotides (e.g., genomic DNA, RNA, etc.) is isolated from a cell utilizing any suitable method (e.g., a commercially available kit). The polynucleotide may be quantified. The quantified polynucleotide may then be partitioned into a plurality of partitions as described herein. The partitioning of the polynucleotide may be performed at a predetermined coverage amount, according to the quantification and the needs of the assay. In some cases, all or most partitions do not comprise polynucleotides that overlap, such that separate mixtures of non-overlapping fragments are formed across the plurality of partitions. The partitioned polynucleotides may then be treated according to any suitable method known in the art or described in this disclosure. For example, the partitioned polynucleotides may be fragmented, amplified, barcoded, and the like.

Species may be partitioned using a variety of methods. For example, species may be diluted and dispensed across a plurality of partitions. A terminal dilution of a medium comprising species may be performed such that the number of partitions exceeds the number of species. Dilution may also be used prior to forming an emulsion or capsules, or prior to spotting a species on a substrate. The ratio of the number of species to the number of partitions may be about 0.1, 0.5, 1, 2, 4, 8, 10, 20, 50, 100, or 1000. The ratio of the number of species to the number of partitions may be at least about 0.1, 0.5, 1, 2, 4, 8, 10, 20, 50, 100, or 1000. The ratio of the number of species to the number of partitions may be less than about 0.1, 0.5, 1, 2, 4, 8, 10, 20, 50, 100, or 1000. The ratio of the number of species to the number of partitions may range from about 0.1-10, 0.5-10, 1-10, 2-10, 10-100, 100-1000, or more.

Partitioning may also be performed using piezoelectric droplet generation (e.g., Bransky et al., *Lab on a Chip*, 2009, 9, 516-520) or surface acoustic waves (e.g., Demirci and Montesano, *Lab on a Chip*, 2007, 7, 1139-1145).

The number of partitions employed may vary depending on the application. For example, the number of partitions may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000 or more. The number of partitions may be at least about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000 or more. The number of partitions may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

The volume of the partitions may vary depending on the application. For example, the volume of any of the partitions described in this disclosure (e.g., wells, spots, droplets (e.g., in an emulsion), and capsules) may be about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be at least about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be less than about 1000 µl, 900 µl, 800 µl, 700 µl, 600 µl, 500 µl, 400 µl, 300 µl, 200 µl, 100 µl, 50 µl, 25 µl, 10 µl, 5 µl, 1 µl, 900 nL, 800 nL, 700 nL, 600 nL, 500 nL, 400 nL, 300 nL, 200 nL, 100 nL, 50 nL, 25 nL, 10 nL, 5 nL, 5 nL, 2.5 nL, 1 nL, 900 pL, 800 pL, 700 pL, 600 pL, 500 pL, 400 pL, 300 pL, 200 pL, 100 pL, 50 pL, 25 pL, 10 pL, 5 pL, 1 pL, 900 fL, 800 fL, 700 fL, 600 fL, 500 fL, 400 fL, 300 fL, 200 fL, 100 fL, 50 fL, 25 fL, 10 fL, 5 fL, 1 fL, or 0.5 fL. The volume of the partitions may be about 0.5 fL-5 pL, 10 pL-10 nL, 10 nL-10 µl, 10 µl-100 µl, or 100 µl to 1 mL.

There may be variability in the volume of fluid in different partitions. More specifically, the volume of different partitions may vary by at least (or at most) plus or minus 1%, 2%, 3%, 4%, 5%, 10%, 20%, 30%, 40%, 50%, 60%, 70%, 80%, 90%, 100%, 200%, 300%, 400%, 500%, or 1000% across a set of partitions. For example, a well (or other partition) may comprise a volume of fluid that is at most 80% of the fluid volume within a second well (or other partition).

Particular species may also be targeted to specific partitions. For example, in some cases, a capture reagent (e.g., an oligonucleotide probe) may be immobilized or placed within a partition to capture specific species (e.g., polynucleotides).

The number of different species or different sets of species that are partitioned may vary depending upon, for example, the particular species to be partitioned and/or the application. Different sets of species may be, for example, sets of identical species where the identical species differ between each set. Or different sets of species may be, for example, sets of different species, where each set differs in its included species. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different species or different sets of species may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different species or different sets of species may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, or 100000000 different species or different sets of species may be partitioned. In some examples, about 1-5, 5-10, 10-50, 50-100, 100-1000, 1000-10000, 10000-100000, 100000-1000000, 10000-1000000, 10000-10000000, or 10000-100000000 species may be partitioned.

Species may also be partitioned at a particular density. For example, species may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700, 000, 800,000, 900,000, 1000000, 2000000, 3000000, 4000000, 5000000, 6000000, 7000000, 8000000, 9000000, 10000000, or 20000000 species per partition. Species may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 or more species per partition. Species may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 species per partition. Species may be partitioned such that each partition contains about 1-5, 5-10, 10-50, 50-100, 100-1000, 1000-10000, 10000-100000, 100000-1000000, 10000-1000000, or 10000-10000000 species per partition.

Species may also be partitioned such that identical species are partitioned at a particular density. For example, identical species may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, or 20000000 identical species per partition. Species may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 or more identical species per partition. Species may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 identical species per partition. Species may be partitioned such that each partition contains about 1-5, 5-10, 10-50, 50-100, 100-1000, 1000-10000, 10000-100000, 100000-1000000, 10000-1000000, or 10000-10000000 identical species per partition.

Species may also be partitioned such that different species are partitioned at a particular density. For example, different species may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, or 20000000 different species per partition. Species may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 or more different species per partition. Species may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, or 20000000 different species per partition. Species may be partitioned such that each partition contains about 1-5, 5-10, 10-50, 50-100, 100-1000, 1000-10000, 10000-100000, 100000-1000000, 10000-1000000, or 10000-10000000 different species per partition.

As will be appreciated, any of the above-described different numbers of species may be provided with any of the above-described barcode densities per partition, and in any of the above-described numbers of partitions.

Species may be partitioned such that at least one partition comprises a species that is unique within that partition. This may be true for about 1%, 5%, 10%, 20%, 30%, 40%, 50%, 60%, 70%, 80%, 90%, or more of the partitions. This may be true for at least about 1%, 5%, 10%, 20%, 30%, 40%, 50%, 60%, 70%, 80%, 90%, or more of the partitions. This may be true for less than about 1%, 5%, 10%, 20%, 30%, 40%, 50%, 60%, 70%, 80%, or 90% of the partitions.

a. Wells as Partitions

In some cases, wells are used as partitions. The wells may be microwells. With reference to FIG. 1A, a well 101 may comprise a medium 102 comprising a species or plurality of species 103. Species may be contained within a well in various configurations. In one example, a species is dispensed directly into a well (e.g., FIG. 1A). A species dispensed directly into a well may be overlaid with a layer that is, for example, dissolvable, meltable, or permeable 104. This layer may be, for example, an oil, wax, membrane, or the like. The layer may be dissolved or melted prior to or after introduction of another species into the well. The well may be sealed at any point, with a sealing layer 105, for example after addition of any species.

In one example, reagents for sample processing are dispensed directly into a well and overlaid with a layer that is dissolvable, meltable, or permeable. A sample comprising an analyte to be processed is introduced on top of the layer. The layer is dissolved or melted, or the analyte (or reagent)

diffuses through the layer. The well is sealed and incubated under appropriate conditions for the processing of the analyte. Processed analyte may then be recovered.

Figure 1B:
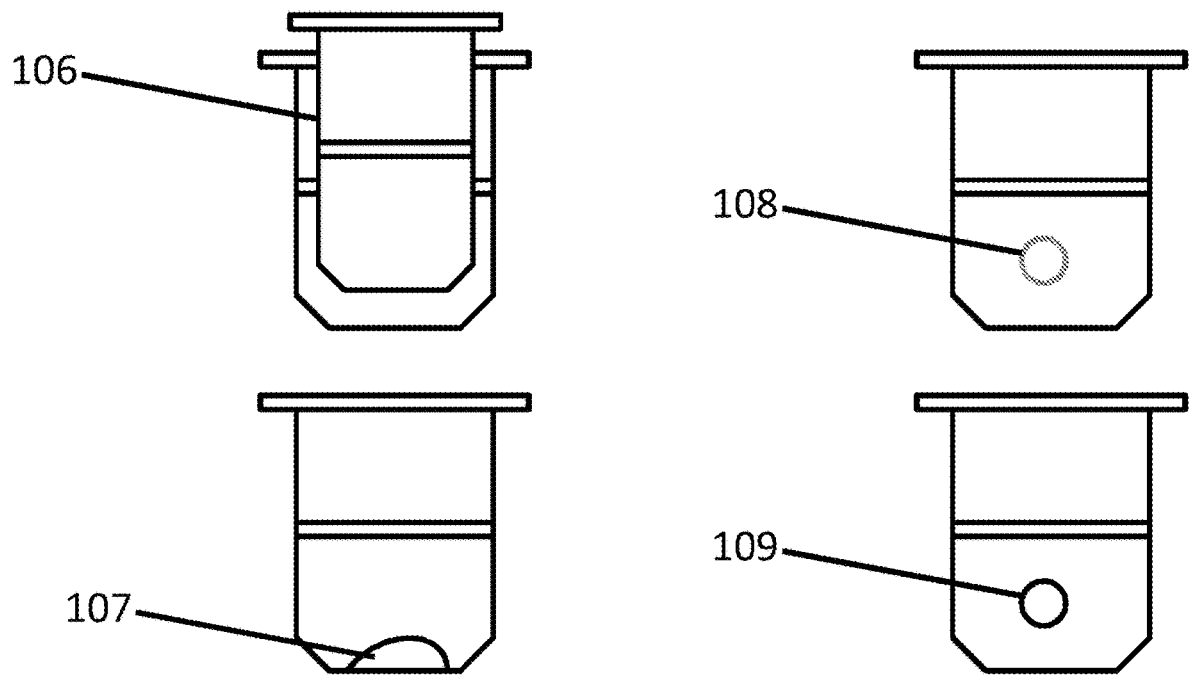

In some cases, wells comprise other partitions. A well may comprise any suitable partition including, for example, with reference to FIG. 1B, another well 106, a spot 107, a droplet (e.g., a droplet in an emulsion) 108, a capsule 109, and the like. Each partition may be present as a single partition or a plurality of partitions, and each partition may comprise the same species or different species.

In one example, a well comprises a capsule comprising reagents for sample processing. A capsule may be loaded into a well using a liquid medium, or loaded into a well without a liquid medium (e.g., essentially dry). As described elsewhere in this disclosure, a capsule may contain one or more capsules, or other partitions. A sample comprising an analyte to be processed is introduced into the well. The well is sealed and a stimulus is applied to cause release of the contents of the capsule into the well, resulting in contact between the reagents and the analyte to be processed. The well is incubated under appropriate conditions for the processing of the analyte. Processed analyte may then be recovered. While this example describes an embodiment where a reagent is in a capsule and an analyte is in the well, the opposite configuration—i.e., reagent in the well and analyte in the capsule—is also possible.

In another example, a well comprises an emulsion and the droplets of the emulsion comprise capsules comprising reagents for sample processing. A sample comprising an analyte to be processed is contained within the droplets of the emulsion. The well is sealed and a stimulus is applied to cause release of the contents of the capsules into the droplets, resulting in contact between the reagents and the analyte to be processed. The well is incubated under appropriate conditions for the processing of the analyte. Processed analyte may then be recovered. While this example describes an embodiment where a reagent is in a capsule and an analyte is in a droplet, the opposite configuration—i.e., reagent in the droplet and analyte in the capsule—is also possible.

Wells may be arranged as an array, for example a microwell array. Based on the dimensions of individual wells and the size of the substrate, the well array may comprise a range of well densities. In some cases, the well density may be 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In some cases, the well density may be at least 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$. In some cases, the well density may be less than 10 wells/cm$^2$, 50 wells/cm$^2$, 100 wells/cm$^2$, 500 wells/cm$^2$, 1000 wells/cm$^2$, 5000 wells/cm$^2$, 10000 wells/cm$^2$, 50000 wells/cm$^2$, or 100000 wells/cm$^2$.

b. Spots as Partitions

Figure 2A:
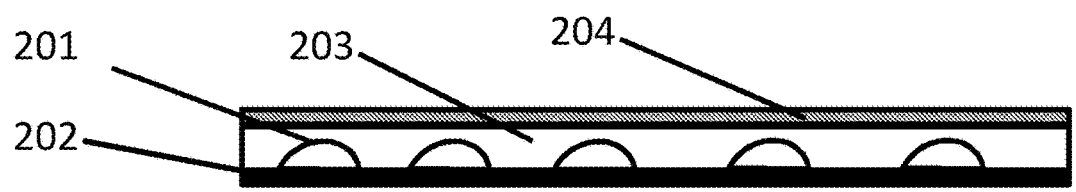
FIGS. 2A-B are schematic examples of spots comprising other types of partitions.

In some cases, spots are used as partitions. With reference to FIG. 2A, a spot may be made, for example, by dispensing a substance 201 on a surface 202. Species may be contained within a spot in various configurations. In one example, a species is dispensed directly into a spot by including the species in the medium used to form the spot. A species dispensed directly onto a spot may be overlaid with a layer that is, for example, dissolvable, meltable, or permeable 203. This layer may be, for example, an oil, wax, membrane, or the like. The layer may be dissolved or melted prior to or after introduction of another species onto the spot. The spot may be sealed at any point, for example after addition of any species, by an overlay 204.

In one example, reagents for sample processing are dispensed directly onto a spot, for example on a glass slide, and overlaid with a layer that is dissolvable, meltable, or permeable. A sample comprising an analyte to be processed is introduced on top of the layer. The layer is dissolved or melted, or the analyte (or reagent) diffuses through the layer. The spot is sealed and incubated under appropriate conditions for the processing of the analyte. Processed analyte may then be recovered.

As described elsewhere in this disclosure (e.g., Table 1), spots may also be arranged within a well. In some cases, a plurality of spots may be arranged within a well such that the contents of each spot do not mix. Such a configuration may be useful, for example, when it is desirable to prevent species from contacting each other. In some cases, a well may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, or more spots. In some cases, a well may comprise at least 2, 3, 4, 5, 6, 7, 8, 9, 10, 11, 12, 13, 14, 15, 16, 17, 18, 19, 20, 21, 22, 23, 24, 25, 26, 27, 28, 29, 30, or more spots. In some cases, a well may comprise less than 2, 3, 4, 5, 6, 7, 8, 9, 10, 11, 12, 13, 14, 15, 16, 17, 18, 19, 20, 21, 22, 23, 24, 25, 26, 27, 28, 29, or 30 spots. In some cases, a well may comprise 2-4, 2-6, 2-8, 4-6, 4-8, 5-10, or 4-12 spots. Upon addition of a substance (e.g., a medium containing an analyte) to the well, the species in the spot may mix. Moreover, using separate spots to contain different species (or combinations of species) may also be useful to prevent cross-contamination of devices used to place the spots inside the well.

Figure 2B:
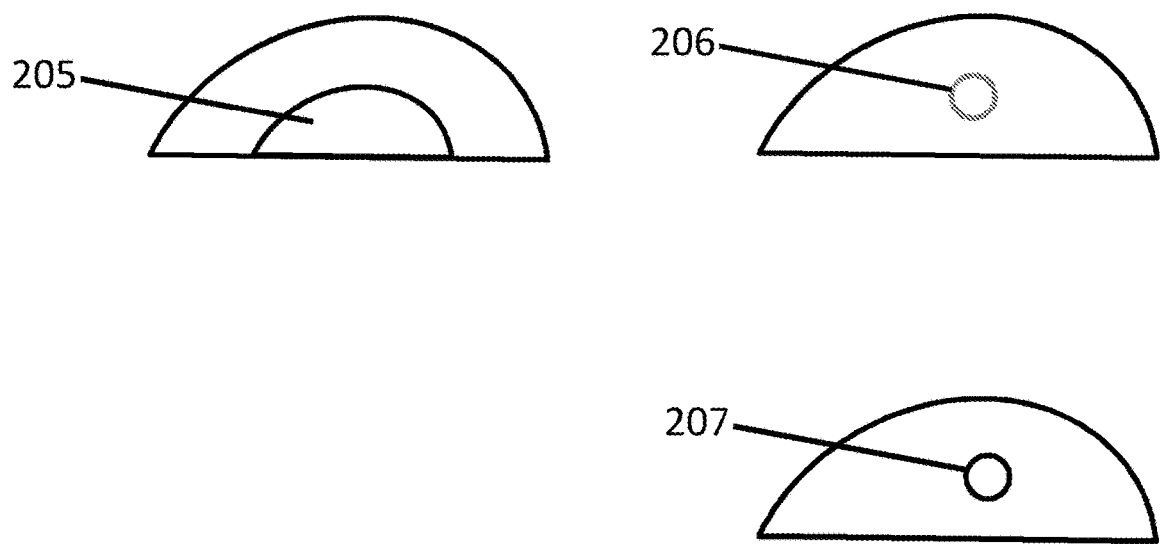

In some cases, spots comprise other partitions. A spot may comprise any suitable partition including, for example, with reference to FIG. 2B, another spot 205, a droplet (e.g., a droplet in an emulsion) 206, a capsule 207, and the like. Each partition may be present as a single partition or a plurality of partitions, and each partition may comprise the same species or different species.

In one example, a spot comprises a capsule comprising reagents for sample processing. As described elsewhere in this disclosure, a capsule may contain one or more capsules, or other partitions. A sample comprising an analyte to be processed is introduced into the spot. The spot is sealed and a stimulus is applied to cause release of the contents of the capsule into the spot, resulting in contact between the reagents and the analyte to be processed. The spot is incubated under appropriate conditions for the processing of the analyte. Processed analyte may then be recovered. While this example describes an embodiment where a reagent is in a capsule and an analyte is in the spot, the opposite configuration—i.e., reagent in the spot and analyte in the capsule—is also possible.

In another example, a spot comprises an emulsion and the droplets of the emulsion comprise capsules comprising reagents for sample processing. A sample comprising an analyte to be processed is contained within the droplets of the emulsion. The spot is sealed and a stimulus is applied to cause release of the contents of the capsules into the droplets, resulting in contact between the reagents and the analyte to be processed. The spot is incubated under appropriate conditions for the processing of the analyte. Processed analyte may then be recovered. While this example describes an embodiment where a reagent is in a capsule and an analyte is in a droplet, the opposite configuration—i.e., reagent in the droplet and analyte in the capsule—is also possible.

Spots may be of uniform size or heterogeneous size. In some cases, the diameter of a spot may be about 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, 1 mm, 2 mm, 5 mm, or 1 cm. A spot may have a diameter of at least about 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, 1 mm, 1 mm, 2 mm, 5 mm, or 1 cm. In some cases, a spot may have a diameter of less than about 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, 1 mm, 1 mm, 2 mm, 5 mm, or 1 cm. In some cases, a spot may have a diameter of about 0.1 μm to 1 cm, 100 μm to 1 mm, 100 μm to 500 μm, 100 μm to 600 μm, 150 μm to 300 μm, or 150 μm to 400 μm.

Spots may be arranged as an array, for example a spot array. Based on the dimensions of individual spots and the size of the substrate, the spot array may comprise a range of spot densities. In some cases, the spot density may be 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$. In some cases, the spot density may be at least 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$. In some cases, the spot density may be less than 10 spots/cm$^2$, 50 spots/cm$^2$, 100 spots/cm$^2$, 500 spots/cm$^2$, 1000 spots/cm$^2$, 5000 spots/cm$^2$, 10000 spots/cm$^2$, 50000 spots/cm$^2$, or 100000 spots/cm$^2$.

c. Emulsions as Partitions

In some cases, the droplets in an emulsion are used as partitions. An emulsion may be prepared, for example, by any suitable method, including methods known in the art. (See e.g., Weizmann et al., Nature Methods, 2006, 3(7):545-550; Weitz et al. U.S. Pub. No. 2012/0211084). In some cases, water-in-fluorocarbon emulsions may be used. These emulsions may incorporate fluorosurfactants such as oligomeric perfluorinated polyethers (PFPE) with polyethylene glycol (PEG). (Holtze et al., Lab on a Chip, 2008, 8(10): 1632-1639). In some cases, monodisperse emulsions may be formed in a microfluidic flow focusing device. (Garstecki et al., Applied Physics Letters, 2004, 85(13):2649-2651).

Figure 3A:
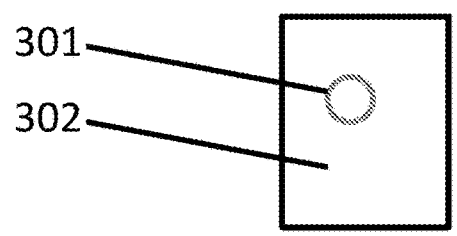
FIGS. 3A-B are schematic examples of a droplet of an emulsion comprising other types of partitions.

FIG. 3A illustrates exemplary embodiments. With reference to FIG. 3A, a species may be contained within a droplet 301 in an emulsion containing, for example, a first phase (e.g., oil or water) forming the droplet 301 and a second (continuous) phase (e.g., water or oil) 302. An emulsion may be a single emulsion, for example, a water-in-oil or an oil-in-water emulsion. An emulsion may be a double emulsion, for example a water-in-oil-in-water or an oil-in-water-in-oil emulsion. Higher-order emulsions are also possible. The emulsion may be held in any suitable container, including any suitable partition described in this disclosure.

Figure 3B:
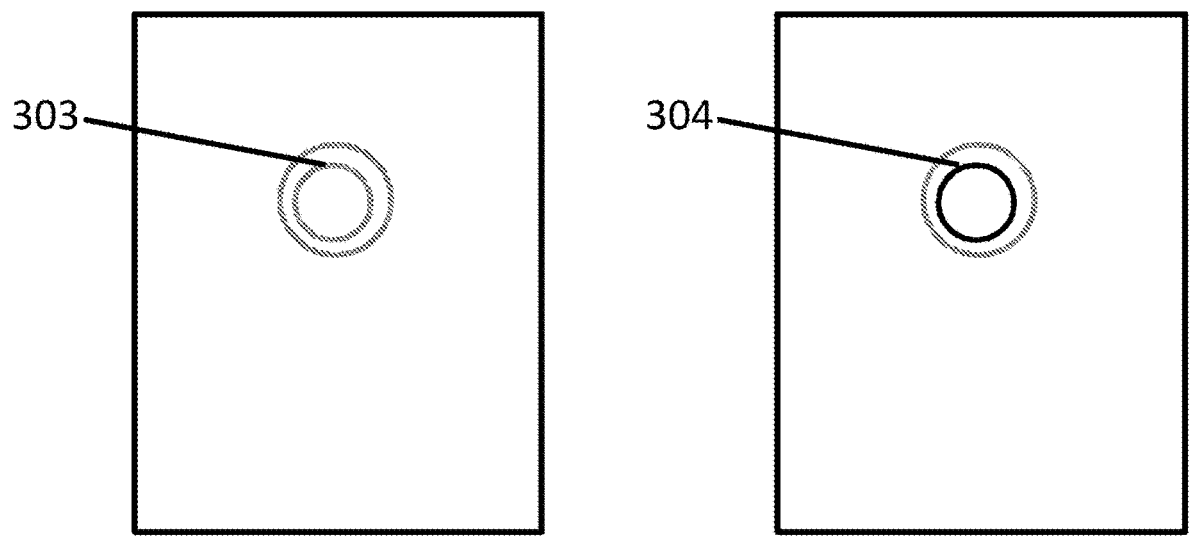

In some cases, droplets in an emulsion comprise other partitions. A droplet in an emulsion may comprise any suitable partition including, for example, with reference to FIG. 3B, another droplet (e.g., a droplet in an emulsion) 303, a capsule 304, and the like. Each partition may be present as a single partition or a plurality of partitions, and each partition may comprise the same species or different species.

In one example, a droplet in an emulsion comprises a capsule comprising reagents for sample processing. As described elsewhere in this disclosure, a capsule may contain one or more capsules, or other partitions. A sample comprising an analyte to be processed is contained within the droplet. A stimulus is applied to cause release of the contents of the capsule into the droplet, resulting in contact between the reagents and the analyte to be processed. The droplet is incubated under appropriate conditions for the processing of the analyte. Processed analyte may then be recovered. While this example describes an embodiment where a reagent is in a capsule and an analyte is in the droplet, the opposite configuration—i.e., reagent in the droplet and analyte in the capsule—is also possible.

The droplets in an emulsion may be of uniform size or heterogeneous size. In some cases, the diameter of a droplet in an emulsion may be about 0.001 μm, 0.01 μm, 0.05 μm, 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, or 1 mm. A droplet may have a diameter of at least about 0.001 μm, 0.01 μm, 0.05 μm, 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, or 1 mm. In some cases, a droplet may have a diameter of less than about 0.001 μm, 0.01 μm, 0.05 μm, 0.1 μm, 0.5 μm, 1 μm, 5 μm, 10 μm, 50 μm, 100 μm, 150 μm, 200 μm, 300 μm, 400 μm, 500 μm, 600 μm, 700 μm, 800 μm, 900 μm, or 1 mm. In some cases, a droplet may have a diameter of about 0.001 μm to 1 mm, 0.01 μm to 900 μm, 0.1 μm to 600 μm, 100 μm to 200 μm, 100 μm to 300 μm, 100 μm to 400 μm, 100 μm to 500 μm, 100 μm to 600 μm, 150 μm to 200 μm, 150 μm to 300 μm, or 150 μm to 400 μm.

Droplets in an emulsion also may have a particular density. In some cases, the droplets are less dense than an aqueous fluid (e.g., water); in some cases, the droplets are denser than an aqueous fluid. In some cases, the droplets are less dense than a non-aqueous fluid (e.g., oil); in some cases, the droplets are denser than a non-aqueous fluid. Droplets may have a density of about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Droplets may have a density of at least about 0.05 g/cm$^3$, 0.1 g/cm$^3$, 0.2 g/cm$^3$, 0.3 g/cm$^3$, 0.4 g/cm$^3$, 0.5 g/cm$^3$, 0.6 g/cm$^3$, 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. In other cases, droplet densities may be at most about 0.7 g/cm$^3$, 0.8 g/cm$^3$, 0.81 g/cm$^3$, 0.82 g/cm$^3$, 0.83 g/cm$^3$, 0.84 g/cm$^3$, 0.85 g/cm$^3$, 0.86 g/cm$^3$, 0.87 g/cm$^3$, 0.88 g/cm$^3$, 0.89 g/cm$^3$, 0.90 g/cm$^3$, 0.91 g/cm$^3$, 0.92 g/cm$^3$, 0.93 g/cm$^3$, 0.94 g/cm$^3$, 0.95 g/cm$^3$, 0.96 g/cm$^3$, 0.97 g/cm$^3$, 0.98 g/cm$^3$, 0.99 g/cm$^3$, 1.00 g/cm$^3$, 1.05 g/cm$^3$, 1.1 g/cm$^3$, 1.2 g/cm$^3$, 1.3 g/cm$^3$, 1.4 g/cm$^3$, 1.5 g/cm$^3$, 1.6 g/cm$^3$, 1.7 g/cm$^3$, 1.8 g/cm$^3$, 1.9 g/cm$^3$, 2.0 g/cm$^3$, 2.1 g/cm$^3$, 2.2 g/cm$^3$, 2.3 g/cm$^3$, 2.4 g/cm$^3$, or 2.5 g/cm$^3$. Such densities can reflect the density of the capsule in any particular fluid (e.g., aqueous, water, oil, etc.)

d. Capsules as Partitions

Figure 4A:
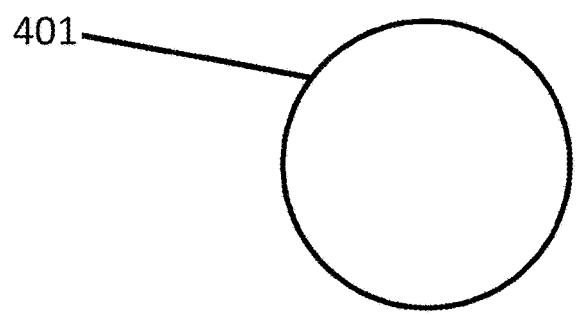
FIGS. 4A-B are schematic examples of capsules comprising other types of partitions.

In some cases, capsules are used as partitions. With reference to FIG. 4A, a capsule 401 may be prepared by any suitable method, including methods known in the art, including emulsification polymerization (Weitz et al. (U.S. Pub. No. 2012/0211084)), layer-by-layer assembly with polyelectrolytes, coacervation, internal phase separation, and flow focusing. Any suitable species may be contained within a capsule. The capsule may be held in any suitable container, including any suitable partition described in this disclosure.

Figure 4B:
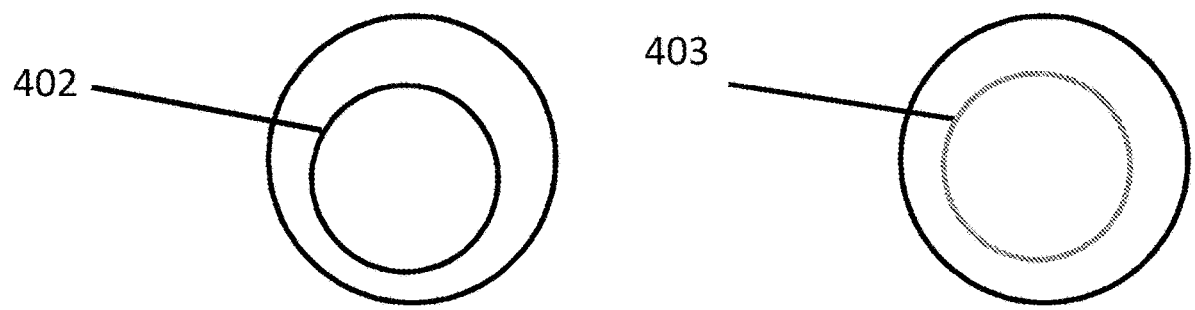

In some cases, capsules comprise other partitions. A capsule may comprise any suitable partition including, for example, with reference to FIG. 4B, another capsule 402, a droplet in an emulsion 403, and the like. Each partition may be present as a single partition or a plurality of partitions, and each partition may comprise the same species or different species.

In one example, an outer capsule comprises an inner capsule. The inner capsule comprises reagents for sample processing. An analyte is encapsulated in the medium between the inner capsule and the outer capsule. A stimulus is applied to cause release of the contents of the inner capsule into the outer capsule, resulting in contact between the reagents and the analyte to be processed. The outer capsule is incubated under appropriate conditions for the processing of the analyte. Processed analyte may then be recovered. While this example describes an embodiment where a reagent is in an inner capsule and an analyte in the medium between the inner capsule and the outer capsule, the opposite configuration—i.e., reagent in the medium between the inner capsule and the outer capsule, and analyte in the inner capsule—is also possible.

Capsules may be pre-formed and filled with reagents by injection. For example, the picoinjection methods described in Abate et al. (Proc. Natl. Acad. Sci. U.S.A., 2010, 107(45), 19163-19166) and Weitz et al. (U.S. Pub. No. 2012/0132288) may be used to introduce reagents into the interior of capsules described herein. Generally, the picoinjection will be performed prior to the hardening of the capsule shell, for example by injecting species into the interior of a capsule precursor, such as a droplet of an emulsion, before formation of the capsule shell.

Capsules may be of uniform size or heterogeneous size. In some cases, the diameter of a capsule may be about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. A capsule may have a diameter of at least about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a capsule may have a diameter of less than about 0.001 µm, 0.01 µm, 0.05 µm, 0.1 µm, 0.5 µm, 1 µm, 5 µm, 10 µm, 50 µm, 100 µm, 150 µm, 200 µm, 300 µm, 400 µm, 500 µm, 600 µm, 700 µm, 800 µm, 900 µm, or 1 mm. In some cases, a capsule may have a diameter of about 0.001 µm to 1 mm, 0.01 µm to 900 µm, 0.1 µm to 600 µm, 100 µm to 200 µm, 100 µm to 300 µm, 100 µm to 400 µm, 100 µm to 500 µm, 100 µm to 600 µm, 150 µm to 200 µm, 150 µm to 300 µm, or 150 µm to 400 µm.

Capsules also may have a particular density. In some cases, the capsules are less dense than an aqueous fluid (e.g., water); in some cases, the capsules are denser than an aqueous fluid. In some cases, the capsules are less dense than a non-aqueous fluid (e.g., oil); in some cases, the capsules are denser than a non-aqueous fluid. Capsules may have a density of about 0.05 $g/cm^3$, 0.1 $g/cm^3$, 0.2 $g/cm^3$, 0.3 $g/cm^3$, 0.4 $g/cm^3$, 0.5 $g/cm^3$, 0.6 $g/cm^3$, 0.7 $g/cm^3$, 0.8 $g/cm^3$, 0.81 $g/cm^3$, 0.82 $g/cm^3$, 0.83 $g/cm^3$, 0.84 $g/cm^3$, 0.85 $g/cm^3$, 0.86 $g/cm^3$, 0.87 $g/cm^3$, 0.88 $g/cm^3$, 0.89 $g/cm^3$, 0.90 $g/cm^3$, 0.91 $g/cm^3$, 0.92 $g/cm^3$, 0.93 $g/cm^3$, 0.94 $g/cm^3$, 0.95 $g/cm^3$, 0.96 $g/cm^3$, 0.97 $g/cm^3$, 0.98 $g/cm^3$, 0.99 $g/cm^3$, 1.00 $g/cm^3$, 1.05 $g/cm^3$, 1.1 $g/cm^3$, 1.2 $g/cm^3$, 1.3 $g/cm^3$, 1.4 $g/cm^3$, 1.5 $g/cm^3$, 1.6 $g/cm^3$, 1.7 $g/cm^3$, 1.8 $g/cm^3$, 1.9 $g/cm^3$, 2.0 $g/cm^3$, 2.1 $g/cm^3$, 2.2 $g/cm^3$, 2.3 $g/cm^3$, 2.4 $g/cm^3$, or 2.5 $g/cm^3$. Capsules may have a density of at least about 0.05 $g/cm^3$, 0.1 $g/cm^3$, 0.2 $g/cm^3$, 0.3 $g/cm^3$, 0.4 $g/cm^3$, 0.5 $g/cm^3$, 0.6 $g/cm^3$, 0.7 $g/cm^3$, 0.8 $g/cm^3$, 0.81 $g/cm^3$, 0.82 $g/cm^3$, 0.83 $g/cm^3$, 0.84 $g/cm^3$, 0.85 $g/cm^3$, 0.86 $g/cm^3$, 0.87 $g/cm^3$, 0.88 $g/cm^3$, 0.89 $g/cm^3$, 0.90 $g/cm^3$, 0.91 $g/cm^3$, 0.92 $g/cm^3$, 0.93 $g/cm^3$, 0.94 $g/cm^3$, 0.95 $g/cm^3$, 0.96 $g/cm^3$, 0.97 $g/cm^3$, 0.98 $g/cm^3$, 0.99 $g/cm^3$, 1.00 $g/cm^3$, 1.05 $g/cm^3$, 1.1 $g/cm^3$, 1.2 $g/cm^3$, 1.3 $g/cm^3$, 1.4 $g/cm^3$, 1.5 $g/cm^3$, 1.6 $g/cm^3$, 1.7 $g/cm^3$, 1.8 $g/cm^3$, 1.9 $g/cm^3$, 2.0 $g/cm^3$, 2.1 $g/cm^3$, 2.2 $g/cm^3$, 2.3 $g/cm^3$, 2.4 $g/cm^3$, or 2.5 $g/cm^3$. In other cases, capsule densities may be at most about 0.7 $g/cm^3$, 0.8 $g/cm^3$, 0.81 $g/cm^3$, 0.82 $g/cm^3$, 0.83 $g/cm^3$, 0.84 $g/cm^3$, 0.85 $g/cm^3$, 0.86 $g/cm^3$, 0.87 $g/cm^3$, 0.88 $g/cm^3$, 0.89 $g/cm^3$, 0.90 $g/cm^3$, 0.91 $g/cm^3$, 0.92 $g/cm^3$, 0.93 $g/cm^3$, 0.94 $g/cm^3$, 0.95 $g/cm^3$, 0.96 $g/cm^3$, 0.97 $g/cm^3$, 0.98 $g/cm^3$, 0.99 $g/cm^3$, 1.00 $g/cm^3$, 1.05 $g/cm^3$, 1.1 $g/cm^3$, 1.2 $g/cm^3$, 1.3 $g/cm^3$, 1.4 $g/cm^3$, 1.5 $g/cm^3$, 1.6 $g/cm^3$, 1.7 $g/cm^3$, 1.8 $g/cm^3$, 1.9 $g/cm^3$, 2.0 $g/cm^3$, 2.1 $g/cm^3$, 2.2 $g/cm^3$, 2.3 $g/cm^3$, 2.4 $g/cm^3$, or 2.5 $g/cm^3$. Such densities can reflect the density of the capsule in any particular fluid (e.g., aqueous, water, oil, etc.)

1. Production of Capsules by Flow Focusing

Figure 5:
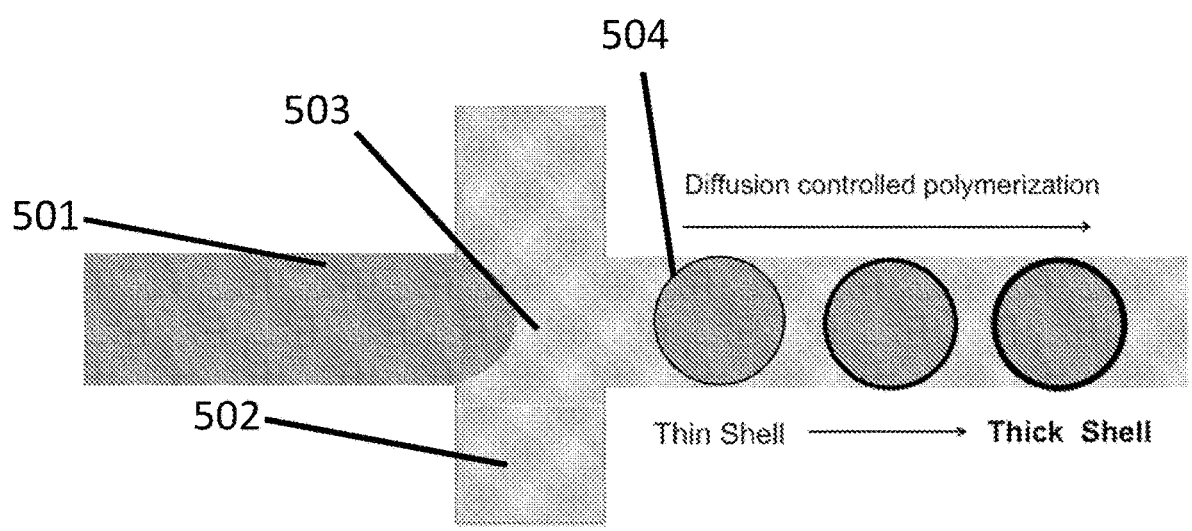
FIG. 5 is a schematic example of a flow focusing method for the production of capsules and/or emulsions.

In some cases, capsules may be produced by flow focusing. Flow focusing is a method whereby a first fluid that is immiscible with a second fluid is flowed into the second fluid. With reference to FIG. 5, a first (e.g., aqueous) fluid comprising a monomer, crosslinker, initiator, and aqueous surfactant 501 is flowed into a second (e.g., oil) fluid comprising a surfactant and an accelerator 502. After entering the second fluid at a T-junction in a microfluidic device 503, a droplet of first fluid breaks off from the first fluid stream and a capsule shell begins to form 504 due to the mixing of the monomer, crosslinker, and initiator in the first fluid and the accelerator in the second fluid. Thus, a capsule is formed. As the capsule proceeds downstream, the shell becomes thicker due to increased exposure to the accelerator. Varying the concentrations of the reagents may also be used to vary the thickness and permeability of the capsule shell.

A species, or other partition such as a droplet, may be encapsulated by, for example, including the species in the first fluid. Including the species in the second fluid may embed the species in the shell of the capsule. Of course, depending on the needs of the particular sample processing method, the phases may also be reversed—i.e., the first phase may be an oil phase and the second phase may be an aqueous phase.

2. Production of Capsules Within Capsules by Flow Focusing

Figure 6:
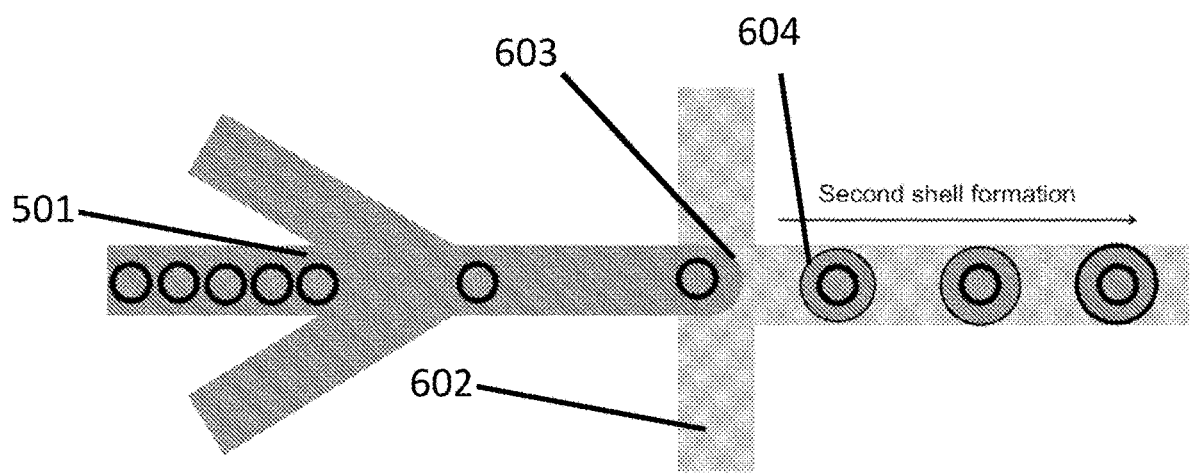
FIG. 6 is a schematic example of a flow focusing method for the production of capsules within capsules, capsules within droplets of an emulsion, or droplets of an emulsion within capsules.

In some cases, capsules within capsules may be produced by flow focusing. With reference to FIG. 6, a first (e.g., aqueous) fluid comprising a capsule, monomer, crosslinker, initiator, and aqueous surfactant 601 is flowed into a second (oil) fluid comprising a surfactant and an accelerator 602. After entering the second fluid at a T-junction in a microfluidic device 603, a droplet of first fluid breaks off from the first fluid stream and a second capsule shell begins to form around the capsule 604 due to the mixing of the monomer, crosslinker, and initiator in the first fluid and the accelerator in the second fluid. Thus, a capsule within a capsule is formed. As the capsule proceeds downstream, the shell becomes thicker due to increased exposure to the accelerator. Varying the concentrations of the reagents may also be used to vary the thickness and permeability of the second capsule shell.

A species may be encapsulated by, for example, including the species in the first fluid. Including the species in the second fluid may embed the species in the second shell of the capsule. Of course, depending on the needs of the particular sample processing method, the phases may also be reversed—i.e., the first phase may be an oil phase and the second phase may be an aqueous phase.

3. Production of Capsules in Batch

Figure 7:
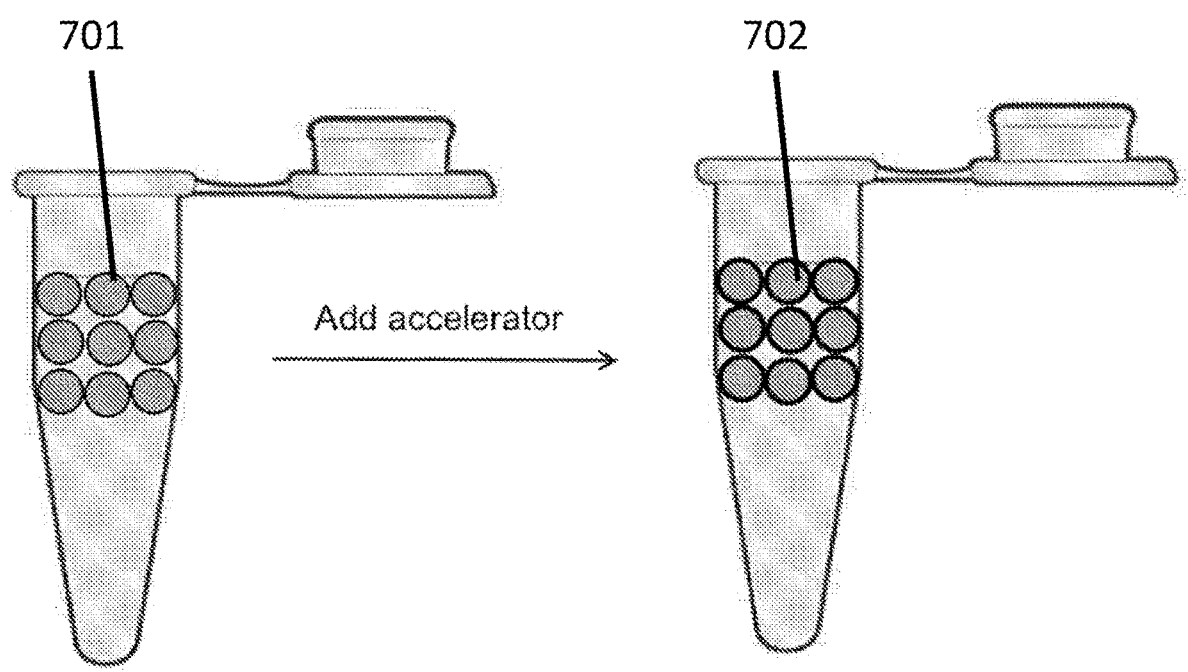
FIG. 7 is a schematic example of a method for the batch production of capsules.

In some cases, capsules may be produced in batch, using capsule precursors, such as the droplets in an emulsion. With reference to FIG. 7, capsule precursors 701 may be formed by any suitable method, for example by producing an emulsion with droplets comprising a monomer, a crosslinker, an initiator, and a surfactant. An accelerator may then be added to the medium, resulting in the formation of capsules 702. As for the methods of flow focusing, the thickness of the shell can be varied by varying the concentrations of the reactants, and the time of exposure to the accelerator. The capsules may then be washed and recovered. As for any method described herein, a species, including other partitions, may be encapsulated within the capsule or, if suitable, within the shell.

In another example, the droplets of an emulsion may be exposed to an accelerator that is present in an outlet well during the emulsion generation process. For example, capsule precursors may be formed by any suitable method, such as the flow focusing method illustrated in FIG. 5. Rather than including the accelerator in second fluid 502, the accelerator may be included in a medium located at the exit of the T-junction (e.g., a medium located at the far-right of the horizontal channel of FIG. 5. As the emulsion droplets (i.e., capsule precursors) exit the channel, they contact the medium comprising the accelerator (i.e., the outlet medium). If the capsule precursor has a density that is less than the density of outlet medium, the capsule precursors will rise through the medium, ensuring convectional and diffusional exposure to the accelerator and reducing the likelihood of polymerization at the outlet of the channel.

III. Species

The methods, compositions, systems, devices, and kits of this disclosure may be used with any suitable species. A species can be, for example, any substance used in sample processing, such as a reagent or an analyte. Exemplary species include whole cells, chromosomes, polynucleotides, organic molecules, proteins, polypeptides, carbohydrates, saccharides, sugars, lipids, enzymes, restriction enzymes, ligases, polymerases, barcodes, adapters, small molecules, antibodies, fluorophores, deoxynucleotide triphosphates (dNTPs), dideoxynucleotide triphosphates (ddNTPs), buffers, acidic solutions, basic solutions, temperature-sensitive enzymes, pH-sensitive enzymes, light-sensitive enzymes, metals, metal ions, magnesium chloride, sodium chloride, manganese, aqueous buffer, mild buffer, ionic buffer, inhibitors, saccharides, oils, salts, ions, detergents, ionic detergents, non-ionic detergents, oligonucleotides, nucleotides, DNA, RNA, peptide polynucleotides, complementary DNA (cDNA), double stranded DNA (dsDNA), single stranded DNA (ssDNA), plasmid DNA, cosmid DNA, chromosomal DNA, genomic DNA, viral DNA, bacterial DNA, mtDNA (mitochondrial DNA), mRNA, rRNA, tRNA, nRNA, siRNA, snRNA, snoRNA, scaRNA, microRNA, dsRNA, ribozyme, riboswitch and viral RNA, a locked nucleic acid (LNA) in whole or part, locked nucleic acid nucleotides, any other type of nucleic acid analogue, proteases, nucleases, protease inhibitors, nuclease inhibitors, chelating agents, reducing agents, oxidizing agents, probes, chromophores, dyes, organics, emulsifiers, surfactants, stabilizers, polymers, water, small molecules, pharmaceuticals, radioactive molecules, preservatives, antibiotics, aptamers, and the like. In summary, the species that are used will vary depending on the particular sample processing needs.

In some cases, a partition comprises a set of species that have a similar attribute (e.g., a set of enzymes, a set of minerals, a set of oligonucleotides, a mixture of different barcodes, a mixture of identical barcodes). In other cases, a partition comprises a heterogeneous mixture of species. In some cases, the heterogeneous mixture of species comprises all components necessary to perform a particular reaction. In some cases, such mixture comprises all components necessary to perform a reaction, except for 1, 2, 3, 4, 5, or more components necessary to perform the reaction. In some cases, such additional components are contained within a different partition or within a solution within or surrounding a partition.

A species may be naturally-occurring or synthetic. A species may be present in a sample obtained using any methods known in the art. In some cases, a sample may be processed before analyzing it for an analyte.

A species may be obtained from any suitable location, including from organisms, whole cells, cell preparations and cell-free compositions from any organism, tissue, cell, or environment. A species may be obtained from environmental samples, biopsies, aspirates, formalin fixed embedded tissues, air, agricultural samples, soil samples, petroleum samples, water samples, or dust samples. In some instances, a species may be obtained from bodily fluids which may include blood, urine, feces, serum, lymph, saliva, mucosal secretions, perspiration, central nervous system fluid, vaginal fluid, or semen. Species may also be obtained from manufactured products, such as cosmetics, foods, personal care products, and the like. Species may be the products of experimental manipulation including, recombinant cloning, polynucleotide amplification, polymerase chain reaction (PCR) amplification, purification methods (such as purification of genomic DNA or RNA), and synthesis reactions.

In some cases, a species may quantified by mass. A species may be provided in a mass of about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng, 1 µg, 5 µg, 10 µg, 15 µg, or 20 µg. A species may be provided in a mass of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng, 1 µg, 5 µg, 10 µg, 15 µg, or 20 µg. A species may be provided in a mass of less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000 ng 1 µg, 5 µg, 10 µg, 15 µg, or 20 µg. A species may be provided in a mass ranging from about 1-10, 10-50, 50-100, 100-200, 200-1000, 1000-10000 ng, 1-5 µg, or 1-20 µg. As described elsewhere in this disclosure, if a species is a polynucleotide, amplification may be used to increase the quantity of a polynucleotide.

Polynucleotides may also be quantified as "genome equivalents." A genome equivalent is an amount of polynucleotide equivalent to one haploid genome of an organism from which the target polynucleotide is derived. For example, a single diploid cell contains two genome equivalents of DNA. Polynucleotides may be provided in an amount ranging from about 1-10, 10-50, 50-100, 100-1000, 1000-10000, 10000-100000, or 100000-1000000 genome equivalents. Polynucleotides may be provided in an amount of at least about 1, 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents. Polynucleotides may be provided in an amount less than about 2, 3, 4, 5, 6, 7, 8, 9, 10, 11, 12, 13, 14, 15, 16, 17, 18, 19, 20, 50, 100, 500, 1000, 1500, 2000, 2500, 3000, 3500, 4000, 4500, 5000, 5500, 6000, 6500, 7000, 7500, 8000, 8500, 9000, 9500, 10000, 20000, 30000, 40000, 50000, 60000 70000, 80000, 90000, 100000, 200000, 300000, 400000, 500000, 600000, 700000, 800000, 900000, or 1000000 genome equivalents.

Polynucleotides may also be quantified by the amount of sequence coverage provided. The amount of sequence coverage refers to the average number of reads representing a given nucleotide in a reconstructed sequence. Generally, the greater the number of times a region is sequenced, the more accurate the sequence information obtained. Polynucleotides may be provided in an amount that provides a range of sequence coverage from about 0.1×-10×, 10-×-50×, 50×-100×, 100×-200×, or 200×-500×. Polynucleotides may be provided in an amount that provides at least about 0.1×, 0.2×, 0.3×, 0.4×, 0.5×, 0.6×, 0.7×, 0.8×, 0.9×, 1.0×, 5×, 10×, 25×, 50×, 100×, 125×, 150×, 175×, or 200× sequence coverage. Polynucleotides may be provided in an amount that provides less than about 0.2×, 0.3×, 0.4×, 0.5×, 0.6×, 0.7×, 0.8×, 0.9×, 1.0×, 5×, 10×, 25×, 50×, 100×, 125×, 150×, 175×, or 200× sequence coverage.

In some cases, species are introduced into a partition either before or after a particular step. For example, a lysis buffer reagent may be introduced into a partition following partitioning of a cellular sample into the partitions. In some cases, reagents and/or partitions comprising reagents are introduced sequentially such that different reactions or operations occur at different steps. The reagents (or partitions comprising reagents) may be also be loaded at steps interspersed with a reaction or operation step. For example, capsules comprising reagents for fragmenting molecules (e.g., nucleic acids) may be loaded into a well, followed by a fragmentation step, which may be followed by loading of capsules comprising reagents for ligating barcodes (or other unique identifiers, e.g., antibodies) and subsequent ligation of the barcodes to the fragmented molecules.

IV. Processing of Analytes and Other Species

In some cases, the methods, compositions, systems, devices, and kits of this disclosure may be used to process a sample containing a species, for example an analyte. Any suitable process can be performed.

a. Fragmentation of Target Polynucleotides

In some cases, the methods, compositions, systems, devices, and kits of this disclosure may be used for polynucleotide fragmentation. Fragmentation of polynucleotides is used as a step in a variety of methods, including polynucleotide sequencing. The size of the polynucleotide fragments, typically described in terms of length (quantified by the linear number of nucleotides per fragment), may vary depending on the source of the target polynucleotide, the method used for fragmentation, and the desired application. A single fragmentation step or a plurality of fragmentation steps may be used.

Fragments generated using the methods described herein may be about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides in length. Fragments generated using the methods described herein may be at least about 10, 20, 100, 200, 300, 400, 500, 1000, 5000, 10000, 100000, 250000, 500000, or more nucleotides in length. Fragments generated using the methods described herein may be less than about 10, 20, 100, 200, 300, 400, 500, 1000, 5000, 10000, 100000, 250000, 500000, nucleotides in length.

Fragments generated using the methods described herein may have a mean or median length of about 1-10, 10-20, 20-50, 50-100, 50-200, 100-200, 200-300, 300-400, 400-500, 500-1000, 1000-5000, 5000-10000, 10000-100000, 100000-250000, or 250000-500000 nucleotides. Fragments generated using the methods described herein may have a mean or median length of at least about 10, 20, 100, 200, 300, 400, 500, 1000, 5000, 10000, 100000, 250000, 500000, or more nucleotides. Fragments generated using the methods described herein may have a mean or median length of less than about 10, 20, 100, 200, 300, 400, 500, 1000, 5000, 10000, 100000, 250000, 500000, nucleotides.

Numerous fragmentation methods are known in the art. For example, fragmentation may be performed through physical, mechanical or enzymatic methods. Physical fragmentation may include exposing a target polynucleotide to heat or to UV light. Mechanical disruption may be used to mechanically shear a target polynucleotide into fragments of the desired range. Mechanical shearing may be accomplished through a number of methods known in the art, including repetitive pipetting of the target polynucleotide, sonication (e.g., using ultrasonic waves), cavitation and nebulization. Target polynucleotides may also be fragmented using enzymatic methods. In some cases, enzymatic digestion may be performed using enzymes such as using restriction enzymes.

While the methods of fragmentation described in the preceding paragraph, and in some paragraphs of the disclosure, are described with reference to "target" polynucleotides, this is not meant to be limiting, above or anywhere else in this disclosure. Any method of fragmentation described herein, or known in the art, can be applied to any polynucleotide used with the invention. In some cases, this polynucleotide may be a target polynucleotide, such as a genome. In other cases, this polynucleotide may be a fragment of a target polynucleotide which one wishes to further fragment. In still other cases, still further fragments may be still further fragmented. Any suitable polynucleotide may be fragmented according the methods described herein.

Restriction enzymes may be used to perform specific or non-specific fragmentation of target polynucleotides. The methods of the present disclosure may use one or more types of restriction enzymes, generally described as Type I enzymes, Type II enzymes, and/or Type III enzymes. Type II and Type III enzymes are generally commercially available and well known in the art. Type II and Type III enzymes recognize specific sequences of nucleotide base pairs within a double stranded polynucleotide sequence (a "recognition sequence" or "recognition site"). Upon binding and recognition of these sequences, Type II and Type III enzymes cleave the polynucleotide sequence. In some cases, cleavage will result in a polynucleotide fragment with a portion of overhanging single stranded DNA, called a "sticky end." In other cases, cleavage will not result in a fragment with an overhang, creating a "blunt end." The methods of the present disclosure may comprise use of restriction enzymes that generate either sticky ends or blunt ends.

Restriction enzymes may recognize a variety of recognition sites in the target polynucleotide. Some restriction enzymes ("exact cutters") recognize only a single recognition site (e.g., GAATTC). Other restriction enzymes are more promiscuous, and recognize more than one recognition site, or a variety of recognition sites. Some enzymes cut at a single position within the recognition site, while others may cut at multiple positions. Some enzymes cut at the same position within the recognition site, while others cut at variable positions.

The present disclosure provides method of selecting one or more restriction enzymes to produce fragments of a desired length. Polynucleotide fragmentation may be simulated in silico, and the fragmentation may be optimized to obtain the greatest number or fraction of polynucleotide fragments within a particular size range, while minimizing the number or fraction of fragments within undesirable size ranges. Optimization algorithms may be applied to select a combination of two or more enzymes to produce the desired fragment sizes with the desired distribution of fragments quantities.

A polynucleotide may be exposed to two or more restriction enzymes simultaneously or sequentially. This may be accomplished by, for example, adding more than one restriction enzyme to a partition, or by adding one restriction enzyme to a partition, performing the digestion, deactivating the restriction enzyme (e.g., by heat treatment) and then adding a second restriction enzyme. Any suitable restriction enzyme may be used alone, or in combination, in the methods presented herein.

In some cases, a species is a restriction enzyme that is a "rare-cutter." The term "rare-cutter enzyme," as used herein, generally refers to an enzyme with a recognition site that occurs only rarely in a genome. The size of restriction fragments generated by cutting a hypothetical random genome with a restriction enzyme may be approximated by $4^N$, where N is the number of nucleotides in the recognition site of the enzyme. For example, an enzyme with a recognition site consisting of 7 nucleotides would cut a genome once every $4^7$ bp, producing fragments of about 16,384 bp. Generally rare-cutter enzymes have recognition sites comprising 6 or more nucleotides. For example, a rare cutter enzyme may have a recognition site comprising or consisting of 6, 7, 8, 9, 10, 11, 12, 13, 14, or 15 nucleotides. Examples of rare-cutter enzymes include NotI (GCGGCCGC), XmaIII (CGGCCG), SstII (CCGCGG), SalI (GTCGAC), NruI (TCGCGA), NheI (GCTAGC), Nb.BbvCI (CCTCAGC), BbvCI (CCTCAGC), AscI (GGCGCGCC), AsiSI (GCGATCGC), FseI (GGCCGGCC), PacI (TTAATTAA), PmeI (GTTTAAAC), SbfI (CCTGCAGG), SgrAI (CRCCGGYG), SwaI (ATTTAAAT), BspQI (GCTCTTC), SapI (GCTCTTC), SfiI (GGCCNNNNNGGCC), CspCI (CAANNNNNGTGG), AbsI (CCTCGAGG), CciNI (GCGGCCGC), FspAI (RTGCGCAY), MauBI (CGCGCGCG), MreI (CGCCGGCG), MssI (GTTTAAAC), PalAI (GGCGCGCC), RgaI (GCGATCGC), RigI (GGCCGGCC), SdaI (CCTGCAGG), SfaAI (GCGATCGC), SgfI (GCGATCGC), SgrDI (CGTCGACG), SgsI (GGCGCGCC), SmiI (ATTTAAAT), SrfI (GCCCGGGC), Sse2321 (CGCCGGCG), Sse83871 (CCTGCAGG), LguI (GCTCTTC), PciSI (GCTCTTC), AarI (CACCTGC), AjuI (GAANNNNNNNTTGG), AloI (GAACNNNNNNTCC), BarI (GAAGNNNNNNTAC), PpiI (GAACNNNNNCTC), PsrI (GAACNNNNNNTAC), and others.

In some cases, polynucleotides may be fragmented and barcoded at the same time. For example, a transposase (e.g., NEXTERA) may be used to fragment a polynucleotide and add a barcode to the polynucleotide.

b. Barcoding

Certain downstream applications, for example polynucleotide sequencing, may rely on the barcodes to identify the origin of a sequence and, for example, to assemble a larger sequence from sequenced fragments. Therefore, it may be desirable to add barcodes to polynucleotide fragments before sequencing. Barcodes may be of a variety of different formats, including polynucleotide barcodes. Depending upon the specific application, barcodes may be attached to polynucleotide fragments in a reversible or irreversible manner. Barcodes may also allow for identification and/or quantification of individual polynucleotide fragments during sequencing.

Barcodes may be loaded into partitions so that one or more barcodes are introduced into a particular partition. Each partition may contain a different set of barcodes. In some cases, each different set of barcodes may comprise a set of identical barcodes. This may be accomplished by directly dispensing the barcodes into the partitions, or by placing the barcodes within a partition within a partition.

The number of different barcodes or different sets of barcodes that are partitioned may vary depending upon, for example, the particular barcodes to be partitioned and/or the application. Different sets of barcodes may be, for example, sets of identical barcodes where the identical barcodes differ between each set. Or different sets of barcodes may be, for example, sets of different barcodes, where each set differs in its included barcodes. For example, about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900, 000, 1000000, 2000000, 3000000, 4000000, 5000000, 6000000, 7000000, 8000000, 9000000, 10000000, 20000000, 50000000, 100000000, or more different barcodes or different sets of barcodes may be partitioned. In some examples, less than about 1, 5, 10, 50, 100, 1000, 10000, 20000, 30000, 40000, 50000, 60000, 70000, 80000, 90000, 100000, 200,000, 300,000, 400,000, 500,000, 600, 000, 700,000, 800,000, 900,000, 1000000, 2000000, 3000000, 4000000, 5000000, 6000000, 7000000, 8000000, 9000000, 10000000, 20000000, 50000000, or 100000000 different barcodes or different sets of barcodes may be partitioned. In some examples, about 1-5, 5-10, 10-50, 50-100, 100-1000, 1000-10000, 10000-100000, 100000-1000000, 10000-1000000, 10000-10000000, or 10000-100000000 barcodes may be partitioned.

Barcodes may be partitioned at a particular density. For example, barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700, 000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 barcodes per partition.

Barcodes may be partitioned such that identical barcodes are partitioned at a particular density. For example, identical barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more identical barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 identical barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 identical barcodes per partition.

Barcodes may be partitioned such that different barcodes are partitioned at a particular density. For example, different barcodes may be partitioned so that each partition contains about 1, 5, 10, 50, 100, 1000, 10000, 20,000, 30,000, 40,000, 50,000, 60,000, 70,000, 80,000, 90,000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned so that each partition contains at least about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, 100000000, or more different barcodes per partition. Barcodes may be partitioned so that each partition contains less than about 1, 5, 10, 50, 100, 1000, 10000, 20000, 30000, 40000, 50000, 60000, 70000, 80000, 90000, 100000, 200,000, 300,000, 400,000, 500,000, 600,000, 700,000, 800,000, 900,000, 1000000, 2000000, 3000000, 4000000, 5000000, 6000000, 7000000, 8000000, 9000000, 10000000, 20000000, 50000000, or 100000000 different barcodes per partition. Barcodes may be partitioned such that each partition contains about 1-5, 5-10, 10-50, 50-100, 100-1000, 1000-10000, 10000-100000, 100000-1000000, 10000-1000000, 10000-10000000, or 10000-100000000 different barcodes per partition.

The number of partitions employed to partition barcodes may vary, for example, depending on the application and/or the number of different barcodes to be partitioned. For example, the number of partitions employed to partition barcodes may be about 5, 10, 50, 100, 250, 500, 750, 1000, 1500, 2000, 2500, 5000, 7500, or 10,000, 20000, 30000, 40000, 50000, 60000, 70000, 80000, 90000, 100,000, 200000, 300000, 400000, 500000, 600000, 700000, 800000, 900000, 1,000,000, 2000000, 3000000, 4000000, 5000000, 10000000, 20000000 or more. The number of partitions employed to partition barcodes may be at least about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, 20000000 or more. The number of partitions employed to partition barcodes may be less than about 5, 10, 50, 100, 250, 500, 750, 1000, 1500, 2000, 2500, 5000, 7500, 10,000, 20000, 30000, 40000, 50000, 60000, 70000, 80000, 90000, 100000, 200000, 300000, 400000, 500000, 600000, 700000, 800000, 900000, 1000000, 2000000, 3000000, 4000000, 5000000, 10000000, or 20000000. The number of partitions employed to partition barcodes may be about 5-10000000, 5-5000000, 5-1,000,000, 10-10,000, 10-5,000, 10-1,000, 1,000-6,000, 1,000-5,000, 1,000-4,000, 1,000-3,000, or 1,000-2,000.

As described above, different barcodes or different sets of barcodes (e.g., each set comprising a plurality of identical barcodes or different barcodes) may be partitioned such that each partition comprises a different barcode or different barcode set. In some cases, each partition may comprise a different set of identical barcodes. Where different sets of identical barcodes are partitioned, the number of identical barcodes per partition may vary. For example, about 100,000 or more different sets of identical barcodes may be partitioned across about 100,000 or more different partitions, such that each partition comprises a different set of identical barcodes. In each partition, the number of identical barcodes per set of barcodes may be about 1,000,000 identical barcodes. In some cases, the number of different sets of barcodes may be equal to or substantially equal to the number of partitions. Any suitable number of different barcodes or different barcode sets (including numbers of different barcodes or different barcode sets to be partitioned described elsewhere herein), number of barcodes per partition (including numbers of barcodes per partition described elsewhere herein), and number of partitions (including numbers of partitions described elsewhere herein) may be combined to generate a diverse library of partitioned barcodes with high numbers of barcodes per partition. Thus, as will be appreciated, any of the above-described different numbers of barcodes may be provided with any of the above-described barcode densities per partition, and in any of the above-described numbers of partitions.

The barcodes may be loaded into the partitions at an expected or predicted ratio of barcodes per species to be barcoded (e.g., polynucleotide fragment, strand of polynucleotide, cell, etc.). In some cases, the barcodes are loaded into partitions such that more than about 1, 2, 3, 4, 5, 6, 7, 8, 9, 10, 20, 50, 100, 500, 1000, 5000, 10000, or 200000 barcodes are loaded per species. In some cases, the barcodes are loaded in the partitions so that less than about 1, 2, 3, 4, 5, 6, 7, 8, 9, 10, 20, 50, 100, 500, 1000, 5000, 10000, or 200000 barcodes are loaded per species. In some cases, the average number of barcodes loaded per species is less than, or greater than, about 0.0001, 0.001, 0.01, 0.1, 1, 2, 3, 4, 5, 6, 7, 8, 9, 10, 20, 50, 100, 500, 1000, 5000, 10000, or 200000 barcodes per species.

When more than one barcode is present per polynucleotide fragment, such barcodes may be copies of the same barcode, or multiple different barcodes. For example, the attachment process may be designed to attach multiple identical barcodes to a single polynucleotide fragment, or multiple different barcodes to the polynucleotide fragment.

The methods provided herein may comprise loading a partition with the reagents necessary for the attachment of barcodes to polynucleotide fragments. In the case of ligation reactions, reagents including restriction enzymes, ligase enzymes, buffers, adapters, barcodes and the like may be loaded into a partition. In the case barcoding by amplification, reagents including primers, DNA polymerases, DNTPs, buffers, barcodes and the like may be loaded into a partition. As described throughout this disclosure, these reagents may be loaded directly into the partition, or via another partition.

Barcodes may be ligated to a polynucleotide fragment using sticky or blunt ends. Barcoded polynucleotide fragments may also be generated by amplifying a polynucleotide fragment with primers comprising barcodes. As with any other species discussed in this disclosure, these modules may be contained within the same or different partitions, depending on the needs of assay or process.

Barcodes may be assembled combinatorially, from smaller components designed to assemble in a modular format. For example, three modules, 1A, 1B, and 1C may be combinatorially assembled to produce barcode 1ABC. Such combinatorial assembly may significantly reduce the cost of synthesizing a plurality of barcodes. For example, a combinatorial system consisting of 3 A modules, 3 B modules, and 3 C modules may generate 3*3*3=27 possible barcode sequences from only 9 modules.

In some cases, barcodes may be combinatorially assembled by mixing two oligonucleotides and hybridizing them to produce annealed or partially annealed oligonucleotides (e.g., forked adapters). These barcodes may comprise an overhang of one or more nucleotides, in order to facilitate ligation with polynucleotide fragments that are to be barcoded. In some cases, the 5' end of the antisense strand may be phosphorylated in order to ensure double-stranded ligation. Using this approach, different modules may be assembled by, for example, mixing oligonucleotides A and B, A and C, A and D, B and C, B, and D, and so on. The annealed oligonucleotides may also be synthesized as a single molecule with a hairpin loop that may be cut after ligation to the polynucleotide to be barcoded.

c. Amplification

In some cases, a polynucleotide is amplified during sample processing. This amplification may be performed in one or more of the partitions described in this disclosure. Amplification may be useful for a variety of purposes, including but not limited to generating multiple copies of polynucleotide sequences, addition of adapter sequences or barcodes to polynucleotides, mutation or error detection, producing higher quality samples for further downstream processing and the like.

An suitable amplification method may be utilized, including polymerase chain reaction (PCR), ligase chain reaction (LCR), helicase-dependent amplification, linear after the exponential PCR (LATE-PCR) asymmetric amplification, digital PCR, degenerate oligonucleotide primer PCR (DOP-PCR), primer extension pre-amplification PCR (PEP-PCR) and ligation mediated PCR, rolling circle amplification, multiple displacement amplification (MDA), and single primer isothermal linear amplification. In one example, MDA may be performed on a species contained within a partition. In some cases, this species is a whole chromosome from a cell.

V. Stimuli-Responsiveness

In some cases, stimuli may be used to trigger the release of a species from a partition. Generally, a stimulus may cause disruption of the structure of a partition, such as the wall of a well, a component of a spot, the stability of a droplet (e.g., a droplet in an emulsion), or the shell of a capsule. These stimuli are particularly useful in inducing a partition to release its contents. Because a partition may be contained within another partition, and each partition may be responsive (or not responsive) to different stimuli, stimuli-responsiveness may be employed to release the contents of one partition (e.g., a partition responsive to the stimulus) into another partition (e.g., a partition not responsive to that stimulus, or less responsive to that stimulus).

Figure 8A:
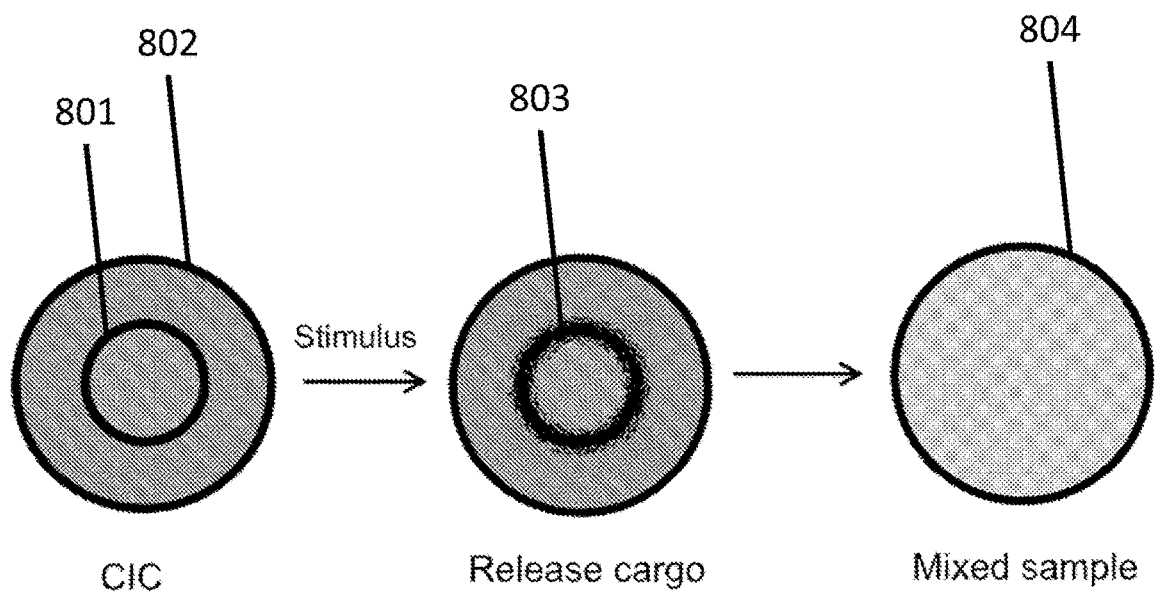
FIGS. 8A-8D are schematic examples of partition-in-partition configurations.

FIG. 8A shows one non-limiting example using a capsule as an exemplary partition. More specifically, FIG. 8A shows selective release of the contents of an inner capsule 801 into the contents of an outer capsule 802 by applying a stimulus that dissolves the inner capsule 803, resulting in a capsule containing a mixed sample 804.

Figure 8B:
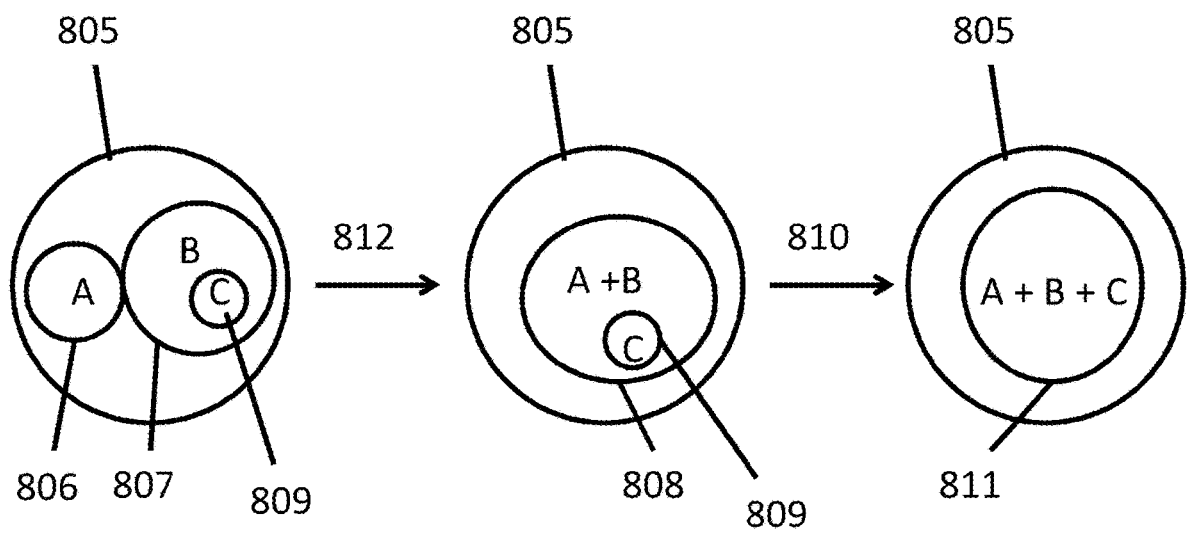

FIG. 8B shows another non-limiting example using a multiple partitions in a partition scheme. An outer partition 805 comprises inner partitions 806 and 807. Inner partition 806 comprises species A and inner partition 807 comprises species B along with its own inner partition 809 comprising species C. For example, the two inner partitions 806 and 807 may be droplets of an emulsion and outer partition 805 comprising the two droplets may be a well. In some cases, one or both of the two droplets may be a micelle. Inner partition 809 may also be a droplet of an emulsion and may be capable of being dissolved or degraded by species A. In some cases species A may be chemical stimulus, such as, for example, a reducing agent (e.g., DTT, TCEP, etc.) capable of breaking disulfide bonds and inner partition 809 may comprise disulfide bonds (e.g., a gel bead comprising disulfide bonds) capable of being broken by species A.

Via diffusion or other means, inner partitions 806 and 807 may come into contact and fuse 812 together such that a new partition 808 can be generated comprising the combined contents of inner partitions 806 and 807 (e.g., species A+B+inner partition 809). The action 810 of species A on inner partition 809 can degrade or dissolve inner partition 809 such that the contents (e.g., species C) of inner partition 809 can be released into partition 808 to generate a new partition 811. Partition 811 comprises the combined contents of inner partitions 806, 807, and 809 (e.g., species A+B+C).

Figure 8C:
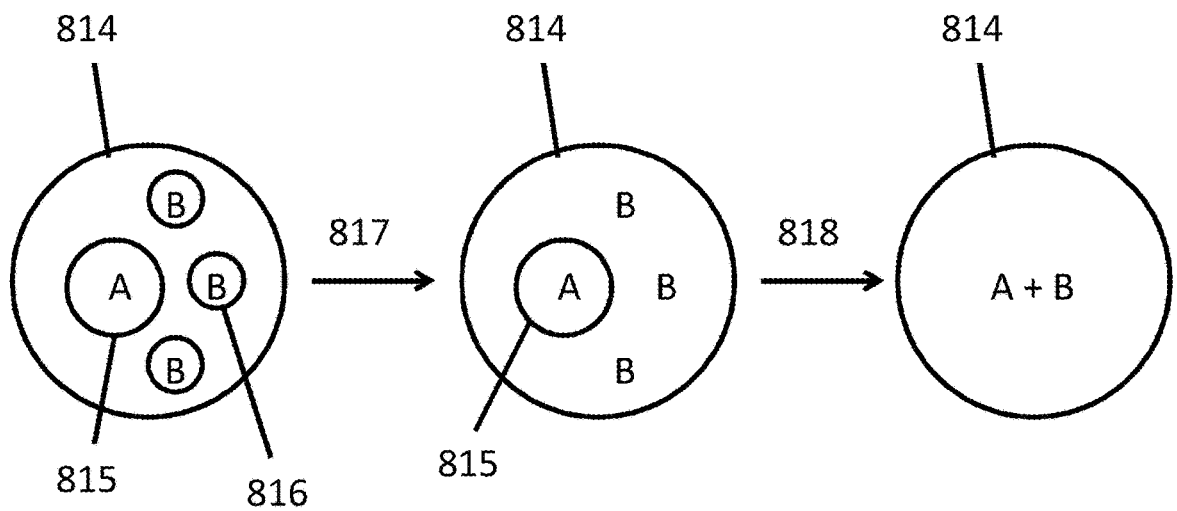

FIG. 8C shows another non-limiting example using a multiple partitions in a partition scheme. Outer partition 814 may comprise inner partition 815 and one or more inner partitions 816 (multiple inner partitions 816 are shown) and may be, for example, a droplet of an emulsion. Inner partition 815 comprises species A and inner partition 816 comprises species B. In some cases, species B may be a chemical stimulus capable of degrading or dissolving inner partition 815. Species B may be, for example, a reducing agent (e.g., DTT, TCEP, etc.) capable of breaking disulfide bonds and inner partition 815 may comprise disulfide bonds (e.g., a gel bead comprising disulfide bonds) capable of being dissolved or degraded by species B. Moreover, inner partition 816 may be heat sensitive (e.g., a paraffin or other wax bead) such that upon application of heat, species B can be released into the interior of outer partition 814.

Upon application of an appropriate stimulus 817 (e.g., heat), inner partitions 816 may be disrupted or degraded such that species B is released to the interior of outer partition 814. The action 818 of species B on inner partition 815 can degrade or dissolve inner partition 815 such that the contents of inner partition 815 can be released to the interior of outer partition 814. Outer partition 814 can then comprise the combined contents (e.g., species A+B) of inner partitions 815 and 816.

In another example, species B as described above with respect to FIG. 8C, may be a reagent necessary to start a reaction in the interior of outer partition 814, such as, for example, an amplification reaction. Upon degradation or disruption of inner partition 816 with the appropriate stimulus (e.g., heat), species B may be released to the interior of outer partition 814, and the desired reaction allowed to commence with or without the application of an additional stimulus.

Figure 8D:
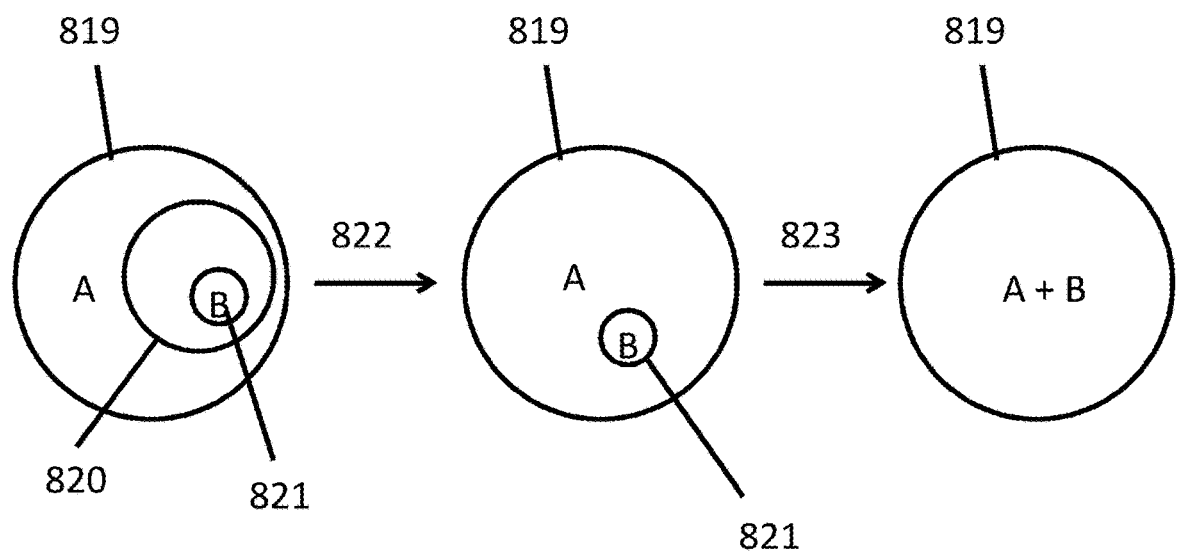

FIG. 8D shows another non-limiting example using a multiple partitions in a partition scheme. Outer partition 819 comprises species A and inner partition 820 and may be, for example, a droplet of an emulsion. Inner partition 820 can be impermeable to species A. Inner partition 820 can comprise its own inner partition 821 which comprises species B. Inner partition 820 may be sensitive to a stimulus such that when the stimulus is applied to inner partition 820, inner partition 820 is dissolved or degraded and inner partition 821 is released to the interior of outer partition 819. Inner partition 820 may be, for example, a microcapsule with a hardened shell that comprises, for example, a heat-sensitive shell that degrades or melts when heat is applied to inner partition 820. Inner partition 821 may be sensitive to species A, such that species A is capable of degrading or dissolving inner partition 821. For example, species A may be a reducing agent capable of breaking disulfide bonds and inner partition 821 may comprise a species comprising disulfide bonds (e.g., a gel bead comprising disulfide bonds) capable of being broken with species A.

Upon application of an appropriate stimulus 822 (e.g., heat), inner partition 820 may be disrupted or degraded such that inner partition 821 is released to the interior of outer partition 819. The action 823 of species A on inner partition 821 can degrade or dissolve inner partition 821 such that the contents of inner partition 821 (e.g., species B) can be released to the interior of outer partition 819. Outer partition 819 can then comprise the combined contents (e.g., species A+B) of inner partition 821 and outer partition 819.

Of course, the configuration shown in FIGS. 8A-8D are merely illustrative, and stimuli-responsiveness may be used to release the contents of any suitable partition into any other suitable partition, medium, or container (see, e.g., Table 1 for more specific examples of partitions within partitions).

Examples of stimuli that may be used include chemical stimuli, bulk changes, biological stimuli, light, thermal stimuli, magnetic stimuli, addition of a medium to a well, and any combination thereof, as described more fully below. (See, e.g., Esser-Kahn et al., (2011) *Macromolecules* 44: 5539-5553; Wang et al., (2009) *ChemPhysChem* 10:2405-2409.)

a. Chemical Stimuli and Bulk Changes

Numerous chemical triggers may be used to trigger the disruption of partitions (e.g., Plunkett et al., Biomacromolecules, 2005, 6:632-637). Examples of these chemical changes may include, but are not limited to pH-mediated changes to the integrity of a component of a partition, disintegration of a component of a partition via chemical cleavage of crosslink bonds, and triggered depolymerization of a component of a partition. Bulk changes may also be used to trigger disruption of partitions.

A change in pH of a solution, such as a decrease in pH, may trigger disruption of a partition via a number of different mechanisms. The addition of acid may cause degradation or disassembly a portion of a partition through a variety of mechanisms. Addition of protons may disassemble cross-linking of polymers in a component of a partition, disrupt ionic or hydrogen bonds in a component of a partition, or create nanopores in a component of a partition to allow the inner contents to leak through to the exterior. A change in pH may also destabilize an emulsion, leading to release of the contents of the droplets.

In some examples, a partition is produced from materials that comprise acid-degradable chemical cross-linkers, such a ketals. A decrease in pH, particular to a pH lower than 5, may induce the ketal to convert to a ketone and two alcohols and facilitate disruption of the partition. In other examples, the partitions may be produced from materials comprising one or more polyelectrolytes that are pH sensitive. A decrease in pH may disrupt the ionic- or hydrogen-bonding interactions of such partitions, or create nanopores therein. In some cases, partitions made from materials comprising polyelectrolytes comprise a charged, gel-based core that expands and contracts upon a change of pH.

Disruption of cross-linked materials comprising a partition can be accomplished through a number of mechanisms. In some examples, a partition can be contacted with various chemicals that induce oxidation, reduction or other chemical changes. In some cases, a reducing agent, such as beta-mercaptoethanol, can be used, such that disulfide bonds of a partition are disrupted. In addition, enzymes may be added to cleave peptide bonds in materials forming a partition, thereby resulting in a loss of integrity of the partition.

Depolymerization can also be used to disrupt partitions. A chemical trigger may be added to facilitate the removal of a protecting head group. For example, the trigger may cause removal of a head group of a carbonate ester or carbamate within a polymer, which in turn causes depolymerization and release of species from the inside of a partition.

In yet another example, a chemical trigger may comprise an osmotic trigger, whereby a change in ion or solute concentration in a solution induces swelling of a material used to make a partition. Swelling may cause a buildup of internal pressure such that a partition ruptures to release its contents. Swelling may also cause an increase in the pore size of the material, allowing species contained within the partition to diffuse out, and vice versa.

A partition may also be made to release its contents via bulk or physical changes, such as pressure induced rupture, melting, or changes in porosity.

b. Biological Stimuli

Biological stimuli may also be used to trigger disruption of partitions. Generally, biological triggers resemble chemical triggers, but many examples use biomolecules, or molecules commonly found in living systems such as enzymes, peptides, saccharides, fatty acids, nucleic acids and the like. For example, partitions may be made from materials comprising polymers with peptide cross-links that are sensitive to cleavage by specific proteases. More specifically, one example may comprise a partition made from materials comprising GFLGK peptide cross links. Upon addition of a biological trigger such as the protease Cathepsin B, the peptide cross links of the shell well are cleaved and the contents of the capsule are released. In other cases, the proteases may be heat-activated. In another example, partitions comprise a component comprising cellulose. Addition of the hydrolytic enzyme chitosan serves as biologic trigger for cleavage of cellulosic bonds, depolymerization of component of the partition comprising chitosan, and release of its inner contents.

c. Thermal Stimuli

Partitions may also be induced to release their contents upon the application of a thermal stimulus. A change in temperature can cause a variety changes to a partition. A change in heat may cause melting of a partition such that a portion of the partition disintegrates, or disruption of an emulsion. In other cases, heat may increase the internal pressure of the inner components of a partition such that the partition ruptures or explodes. In still other cases, heat may transform a partition into a shrunken dehydrated state. Heat may also act upon heat-sensitive polymers used as materials to construct partitions.

In one example, a partition is made from materials comprising a thermo-sensitive hydrogel. Upon the application of heat, such as a temperature above 35 C, the hydrogel material shrinks. The sudden shrinkage of the material increases the pressure and ruptures the partition.

In some cases, a material used to produce a partition may comprise a diblock polymer, or a mixture of two polymers, with different heat sensitivities. One polymer may be particularly likely to shrink after the application of heat, while the other is more heat-stable. When heat is applied to such shell wall, the heat-sensitive polymer may shrink, while the other remains intact, causing a pore to form. In still other cases, a material used to produce a partition may comprise magnetic nanoparticles. Exposure to a magnetic field may cause the generation of heat, leading to rupture of the partition.

d. Magnetic Stimuli

Inclusion of magnetic nanoparticles in a material used to produce a partition may allow triggered rupture of the partition, as described above, as well as enable guidance of these partitions to other partitions (e.g., guidance of capsules to wells in an array). In one example, incorporation of $Fe_3O_4$ nanoparticles into materials used to produce partitions triggers rupture in the presence of an oscillating magnetic field stimulus.

e. Electrical and Light Stimuli

A partition may also be disrupted as the result of electrical stimulation. Similar to the magnetic particles described in the previous section, electrically sensitive particles can allow for both triggered rupture of partitions, as well as other functions such as alignment in an electric field or redox reactions. In one example, partitions made from materials comprising electrically sensitive material are aligned in an electric field such that release of inner reagents can be controlled. In other examples, electric fields may induce redox reactions within a partition that may increase porosity.

A light stimulus may also be used to disrupt the partitions. Numerous light triggers are possible and may include systems that use various molecules such as nanoparticles and chromophores capable of absorbing photons of specific ranges of wavelengths. For example, metal oxide coatings can be used to produce certain partitions. UV irradiation of partitions coated with SiO2/TiO2 may result in disintegration of the partition wall. In yet another example, photo switchable materials such as azobenzene groups may be incorporated in the materials used to produce the partitions. Upon the application of UV or visible light, chemicals such as these undergo a reversible cis-to-trans isomerization upon absorption of photons. In this aspect, incorporation of photo switches results in disintegration of a portion of a partition, or an increase in porosity of a portion of a partition.

f. Application of Stimuli

The devices, methods, compositions, systems, and kits of this disclosure may be used in combination with any apparatus or device that provides such trigger or stimulus. For example, if the stimulus is thermal, a device may be used in combination with a heated or thermally controlled plate, which allows heating of the wells and may induce the rupture of capsules. Any of a number of methods of heat transfer may be used for thermal stimuli, including but not limited to applying heat by radiative heat transfer, convective heat transfer, or conductive heat transfer. In other cases, if the stimulus is a biological enzyme, the enzyme may be injected into a device such that it is deposited into each well. In another aspect, if the stimulus is a magnetic or electric field, a device may be used in combination with a magnetic or electric plate.

VI. Applications a. Polynucleotide Sequencing

Generally, the methods and compositions provided herein are useful for preparation of polynucleotide fragments for downstream applications such as sequencing. Sequencing may be performed by any available technique. For example, sequencing may be performed by the classic Sanger sequencing method. Sequencing methods may also include: high-throughput sequencing, pyrosequencing, sequencing-by-synthesis, single-molecule sequencing, nanopore sequencing, sequencing-by-ligation, sequencing-by-hybridization, RNA-Seq (Illumina), Digital Gene Expression (Helicos), next generation sequencing, single molecule sequencing by synthesis (SMSS) (Helicos), massively-parallel sequencing, clonal single molecule Array (Solexa), shotgun sequencing, SMRT sequencing (Pacific Biosciences) Maxim-Gilbert sequencing, primer walking, and any other sequencing methods known in the art.

In some cases varying numbers of fragments are sequenced. For example, in some cases about 30%-90% of the fragments are sequenced. In some cases, about 35%-85%, 40%-80%, 45%-75%, 50%-70%, 55%-65%, or 50%-60% of the fragments are sequenced. In some cases, at least about 30%, 40%, 50%, 60%, 70%, 80%, or 90% of the fragments are sequenced. In some cases less than about 30%, 40%, 50%, 60%, 70%, 80%, or 90% of the fragments are sequenced.

In some cases sequences from fragments are assembled to provide sequence information for a contiguous region of the original target polynucleotide that is longer than the individual sequence reads. Individual sequence reads may be about 10-50, 50-100, 100-200, 200-300, 300-400, or more nucleotides in length.

The identities of the barcode tags may serve to order the sequence reads from individual fragments as well as to differentiate between haplotypes. For example, during the partitioning of individual fragments, parental polynucleotide fragments may separated into different partitions. With an increase in the number of partitions, the likelihood of a fragment from both a maternal and paternal haplotype contained in the same partition becomes negligibly small.

Thus, sequence reads from fragments in the same partition may be assembled and ordered.

b. Polynucleotide Phasing

This disclosure also provides methods and compositions to prepare polynucleotide fragments in such a manner that may enable phasing or linkage information to be generated. Such information may allow for the detection of linked genetic variations in sequences, including genetic variations (e.g., SNPs, mutations, indels, copy number variations, transversions, translocations, inversions, etc.) that are separated by long stretches of polynucleotides. The term "indel" refers to a mutation resulting in a colocalized insertion and deletion and a net gain or loss in nucleotides. A "microindel" is an indel that results in a net gain or loss of 1 to 50 nucleotides. These variations may exist in either a cis or trans relationship. In a cis relationship, two or more genetic variations exist in the same polynucleotide or strand. In a trans relationship, two or more genetic variations exist on multiple polynucleotide molecules or strands.

Methods provided herein may be used to determine polynucleotide phasing. For example, a polynucleotide sample (e.g., a polynucleotide that spans a given locus or loci) may be partitioned such that at most one molecule of polynucleotide is present per partition. The polynucleotide may then be fragmented, barcoded, and sequenced. The sequences may be examined for genetic variation. The detection of genetic variations in the same sequence tagged with two different bar codes may indicate that the two genetic variations are derived from two separate strands of DNA, reflecting a trans relationship. Conversely, the detection of two different genetic variations tagged with the same bar codes may indicate that the two genetic variations are from the same strand of DNA, reflecting a cis relationship.

Phase information may be important for the characterization of a polynucleotide fragment, particularly if the polynucleotide fragment is derived from a subject at risk of, having, or suspected of a having a particular disease or disorder (e.g., hereditary recessive disease such as cystic fibrosis, cancer, etc.). The information may be able to distinguish between the following possibilities: (1) two genetic variations within the same gene on the same strand of DNA and (2) two genetic variations within the same gene but located on separate strands of DNA. Possibility (1) may indicate that one copy of the gene is normal and the individual is free of the disease, while possibility (2) may indicate that the individual has or will develop the disease, particularly if the two genetic variations are damaging to the function of the gene when present within the same gene copy. Similarly, the phasing information may also be able to distinguish between the following possibilities: (1) two genetic variations, each within a different gene on the same strand of DNA and (2) two genetic variations, each within a different gene but located on separate strands of DNA.

c. Sequencing Polynucleotides from Small Numbers of Cells

Methods provided herein may also be used to prepare polynucleotide contained within cells in a manner that enables cell-specific information to be obtained. The methods enable detection of genetic variations (e.g., SNPs, mutations, indels, copy number variations, transversions, translocations, inversions, etc.) from very small samples, such as from samples comprising about 10-100 cells. In some cases, about 1, 5, 10, 20, 30, 40, 50, 60, 70, 80, 90 or 100 cells may be used in the methods described herein. In some cases, at least about 1, 5, 10, 20, 30, 40, 50, 60, 70, 80, 90 or 100 cells may be used in the methods described herein. In other cases, at most about 5, 10, 20, 30, 40, 50, 60, 70, 80, 90 or 100 cells may be used in the methods described herein.

In an example, a method comprises partitioning a cellular sample (or crude cell extract) such that at most one cell (or extract of one cell) is present per partition, lysing the cells, fragmenting the polynucleotides contained within the cells by any of the methods described herein, attaching the fragmented polynucleotides to barcodes, pooling, and sequencing.

As described elsewhere herein, the barcodes and other reagents may be contained within a partition (e.g., a capsule). These capsules may be loaded into another partition (e.g., a well) before, after, or concurrently with the loading of the cell, such that each cell is contacted with a different capsule. This technique may be used to attach a unique barcode to polynucleotides obtained from each cell. The resulting tagged polynucleotides may then be pooled and sequenced, and the barcodes may be used to trace the origin of the polynucleotides. For example, polynucleotides with identical barcodes may be determined to originate from the same cell, while polynucleotides with different barcodes may be determined to originate from different cells.

The methods described herein may be used to detect the distribution of oncogenic mutations across a population of cancerous tumor cells. For example, some tumor cells may have a mutation, or amplification, of an oncogene (e.g., HER2, BRAF, EGFR, KRAS) in both alleles (homozygous), others may have a mutation in one allele (heterozygous), and still others may have no mutation (wild-type). The methods described herein may be used to detect these differences, and also to quantify the relative numbers of homozygous, heterozygous, and wild-type cells. Such information may be used, for example, to stage a particular cancer and/or to monitor the progression of the cancer and its treatment over time.

In some examples, this disclosure provides methods of identifying mutations in two different oncogenes (e.g., KRAS and EGFR). If the same cell comprises genes with both mutations, this may indicate a more aggressive form of cancer. In contrast, if the mutations are located in two different cells, this may indicate that the cancer is more benign, or less advanced.

d. Analysis of Gene Expression

Methods of the disclosure may be applicable to processing samples for the detection of changes in gene expression. A sample may comprise a cell, mRNA, or cDNA reverse transcribed from mRNA. The sample may be a pooled sample, comprising extracts from several different cells or tissues, or a sample comprising extracts from a single cell or tissue.

Cells may be placed directly into a partition (e.g., a microwell) and lysed. After lysis, the methods of the invention may be used to fragment and barcode the polynucleotides of the cell for sequencing. Polynucleotides may also be extracted from cells prior to introducing them into a partition used in a method of the invention. Reverse transcription of mRNA may be performed in a partition described herein, or outside of such a partition. Sequencing cDNA may provide an indication of the abundance of a particular transcript in a particular cell over time, or after exposure to a particular condition.

The methods presented above provide several advantages over current polynucleotide processing methods. First, interoperator variability is greatly reduced. Second, the methods may be carried out in microfluidic devices, which have a low cost and can be easily fabricated. Third, the controlled fragmentation of the target polynucleotides allows the user to produce polynucleotide fragments with a defined and appropriate length. This aids in partitioning the polynucleotides and also reduces the amount of sequence information loss due to the present of overly-large fragments. The methods and systems also provide a facile workflow that maintains the integrity of the processed polynucleotide. Additionally, the use of restriction enzymes enables the user to create DNA overhangs ("sticky ends") that may be designed for compatibility with adapters and/or barcodes.

e. Partitioning of Polynucleotides, Such as Chromosomes, from Cells

In one example the methods, compositions, systems, devices, and kits provided in this disclosure may be used to partition polynucleotides, including whole chromosomes, from cells. In one example, a single cell or a plurality of cells (e.g., 2, 10, 50, 100, 1000, 10000, 25000, 50000, 100000, 500000, 1000000, or more cells) is loaded into a vessel with lysis buffer and proteinase K, and incubated for a specified period of time. Utilization of a plurality of cells will enable polynucleotide phasing, for example, by partitioning each polynucleotide to be analyzed in its own partition.

After incubation, the cell lysate is partitioned, for example by flow focusing the cell lysate into a capsule. If phasing is to be performed, flow focusing is performed such that each capsule comprises only a single analyte (e.g., a single chromosome), or only a single copy of any particular chromosome (e.g., one copy of a first chromosome and one copy of a second chromosome). In some cases, a plurality of chromosomes may be encapsulated within the same capsule, so long as the chromosomes are not the same chromosome. The encapsulation is performed under gentle flow, to minimize shearing of the polynucleotides. The capsule may be porous, to allow washing of the contents of the capsule, and introduction of reagents into the capsule, while maintaining the polynucleotides (e.g., chromosomes) within the capsules. The encapsulated polynucleotides (e.g., chromosomes) may then be processed according to any of the methods provided in this disclosure, or known in the art. The capsule shells protect the encapsulated polynucleotides (e.g., chromosomes) from shearing and further degradation. Of course, this method can also be applied to any other cellular component.

As described above, the capsule shell may be used to protect a polynucleotide from shearing. However, a capsule may also be used as a partition to enable compartmentalized shearing of a polynucleotide or other analyte. For example, in some cases a polynucleotide may be encapsulated within a capsule and then subject to ultrasonic shear, or any other suitable shearing. The capsule shell may be configured to remain intact under the shear, while the encapsulated polynucleotide may be sheared, but will remain within the capsule. In some cases, a hydrogel droplet may be used to accomplish the same end.

VIII. Kits

In some cases, this disclosure provides kits comprising reagents for the generation of partitions. The kit may comprise any suitable reagents and instructions for the generation of partitions and partitions within partitions.

In one example, a kit comprises reagents for generating capsules within droplets in an emulsion. For example, a kit may comprise reagents for generating capsules, reagents for generating an emulsion, and instructions for introducing the capsules into the droplets of the emulsion. As specified throughout this disclosure, any suitable species may be incorporated into the droplets and/or into the capsule. A kit of this disclosure may also provide any of these species. Similarly, as described throughout the disclosure, the cap-sule may be designed to release its contents into the droplets of the emulsion upon the application of a stimulus.

In another example, a kit comprises reagents for generating capsules within capsules. For example, a kit may comprise reagents for generating inner capsules, reagents for generating outer capsules, and instructions for generating capsules within capsules. As specified throughout this disclosure, any suitable species may be incorporated into the inner and/or outer capsules. A kit of this disclosure may also provide any of these species. Similarly, as described throughout the disclosure, the inner capsule may be designed to release its contents into the outer capsule upon the application of a stimulus.

IX. Devices

In some cases, this disclosure provides devices comprising partitions for the processing of analytes. A device may be a microwell array, or a micro spot array, as described elsewhere in this disclosure. A device may formed in a manner that it comprises any suitable partition. In some cases, a device comprises a plurality of wells, or a plurality of spots. Of course, any partition in a device may also hold other partitions, such as a capsule, a droplet in an emulsion, and the like.

A device may be formed from any suitable material. In some examples, a device is formed from a material selected from the group consisting of fused silica, soda lime glass, borosilicate glass, poly(methyl methacrylate), sapphire, silicon, germanium, cyclic olefin copolymer, polyethylene, polypropylene, polyacrylate, polycarbonate, plastic, and combinations thereof.

In some cases, a device comprises channels for the flow of fluids into and between partitions. Any suitable channels may be used. A device may comprise a fluid inlet and a fluid outlet. The inlet and outlet may be attached to liquid handling devices to introduce species into the device. The device may be sealed, before or after introduction of any species.

Materials that are hydrophilic and/or hydrophobic may be used in different parts of the device. For example, in some cases a device of this disclosure comprises a partition with an interior surface comprising a hydrophilic material. In some cases a surface exterior to the partitions comprises a hydrophobic material. In some cases, a fluid flow path is coated with a hydrophobic or hydrophilic material.

As will be appreciated, the instant disclosure provides for the use of any of the compositions, methods, devices, and kits described herein for a particular use or purpose, including the various applications, uses, and purposes described herein. For example, the disclosure provides for the use of the compositions, methods, devices, and kits described herein, in partitioning species, in partitioning oligonucleotides, in stimulus-selective release of species from partitions, in performing reactions (e.g., ligation and amplification reactions) in partitions, in performing nucleic acid synthesis reactions, in barcoding nucleic acid, in preparing polynucleotides for sequencing, in sequencing polynucleotides, in mutation detection, in neurologic disorder diagnostics, in diabetes diagnostics, in fetal aneuploidy diagnostics, in cancer mutation detection and forensics, in disease detection, in medical diagnostics, in low input nucleic acid applications, in circulating tumor cell (CTC) sequencing, in polynucleotide phasing, in sequencing polynucleotides from small numbers of cells, in analyzing gene expression, in

EXAMPLES

Example 1: Production of Capsules by Flow Focusing

Figure 9A:
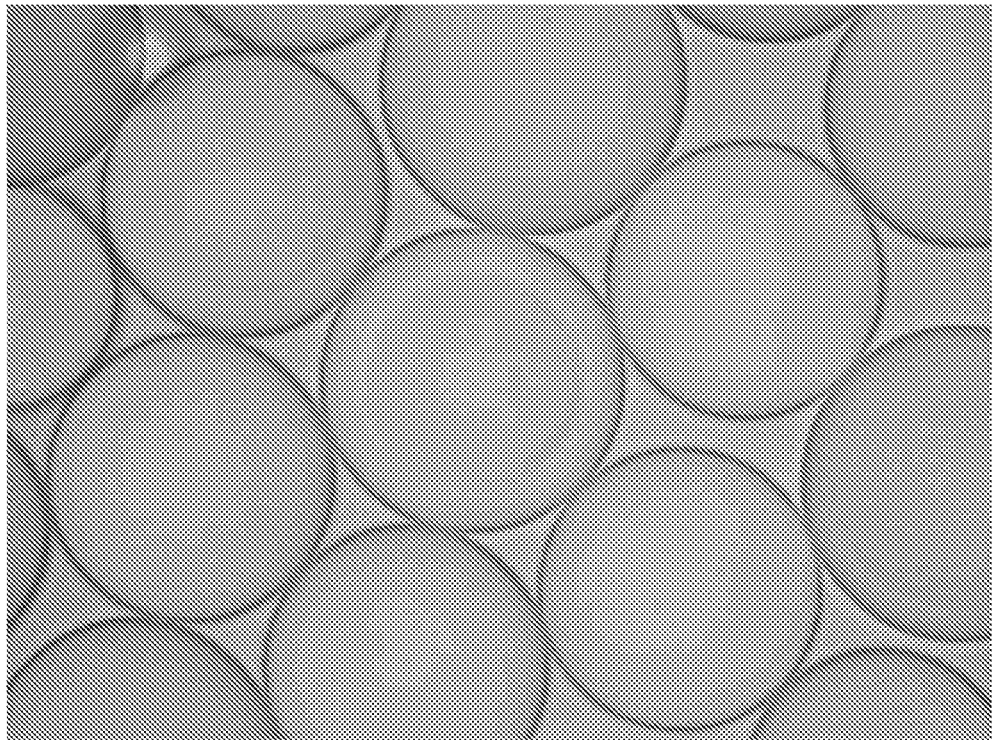
FIGS. 9A-B provide micrographs of capsules formed as described in Example 1.

Capsules were produced according to the method illustrated in FIG. 5 and the corresponding description of FIG. 5. The first fluid 501 was an aqueous fluid that contained 8% (w/v) N-isopropylacrylamide, 0.5% (w/v) PLURONIC F67, 2.5% (w/v) ammonium persulfate, and 1% (w/v) N,N'-methylenebisacrylamide. The second fluid 502 was a fluorous oil (HFE-7500) fluid that contained 2% (w/v) KRYTOX FSH and 1% (v/v) N,N,N,N-tetramethylethylene diamine. The T-junction was 100 microns in width, in either direction. The flow rate was adjusted to maintain an oil to aqueous ratio of 2:1 (20 uL/min and 10 uLmin, respectively). The resulting capsules are shown in FIG. 9A. The shells of the capsules are clearly visible as dark layers surrounding the interior. The size of the capsules is approximately 120 um.

Figure 9B:
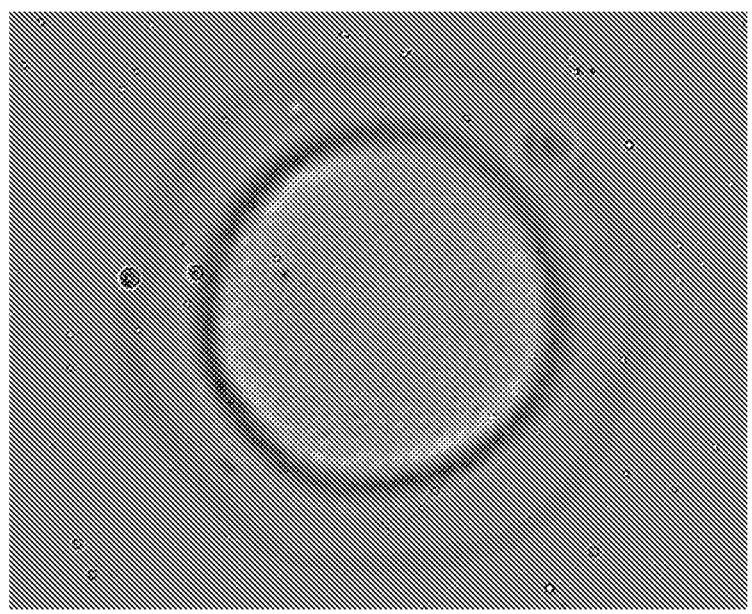

The capsules were washed and resuspended in water. FIG. 9B shows a micrograph of a single capsule, indicating that the integrity of the capsules is maintained during washing and resuspension.

Example 2: Production of Capsules in Batch

Figure 10:
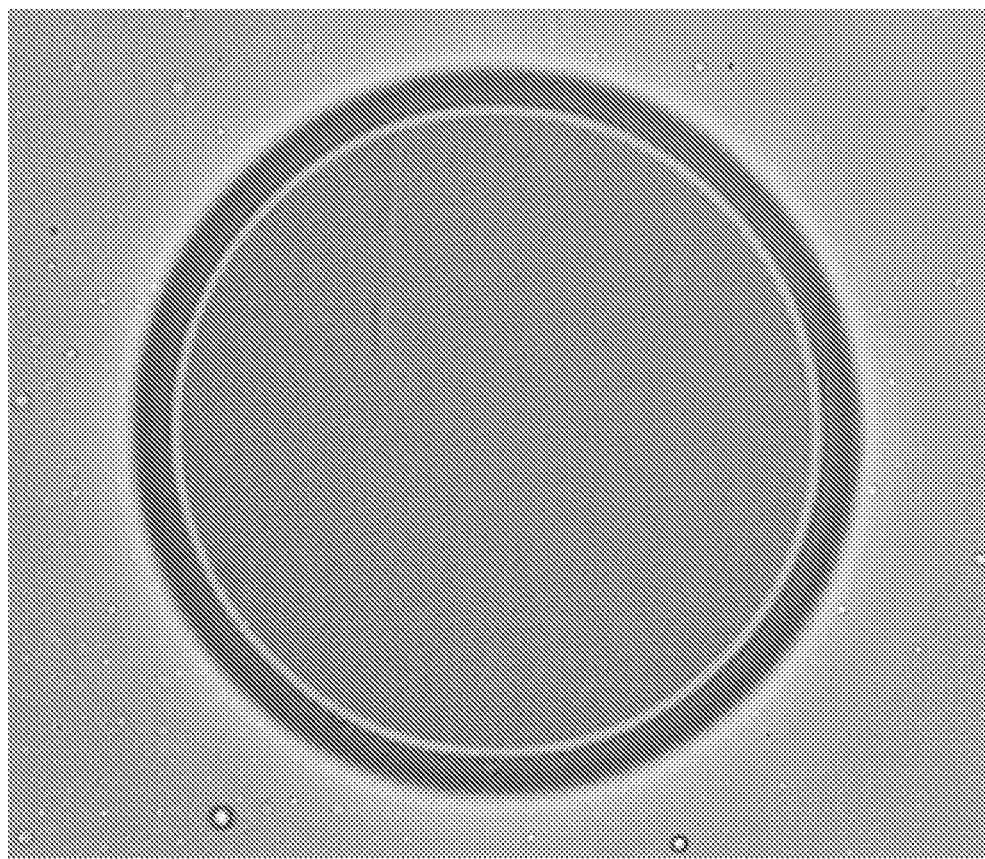
FIG. 10 provides a micrograph of a capsule formed as described in Example 2.

Capsules were produced according to the method illustrated in FIG. 7 and the corresponding description of FIG. 7. The first capsule precursors 701 contained 8% (w/v) N-isopropylacrylamide, 0.5% (w/v) PLURONIC F67, 2.5% (w/v) ammonium persulfate, and 1% (w/v) N,N'-methylenebisacrylamide stabilized by 2% (w/v) KRYTOX FSL in HFE7500. N,N,N, N-tetramethylethylene diamine was added to the medium containing the capsule precursors, at a concentration of 2% (w/v). A micrograph of a resulting capsule is shown in FIG. 10. The shell of the capsules is clearly visible as dark layers surrounding the interior. The size of the capsules is approximately 120 microns.

Example 3: Thermally-Responsive Capsules

Figure 11:
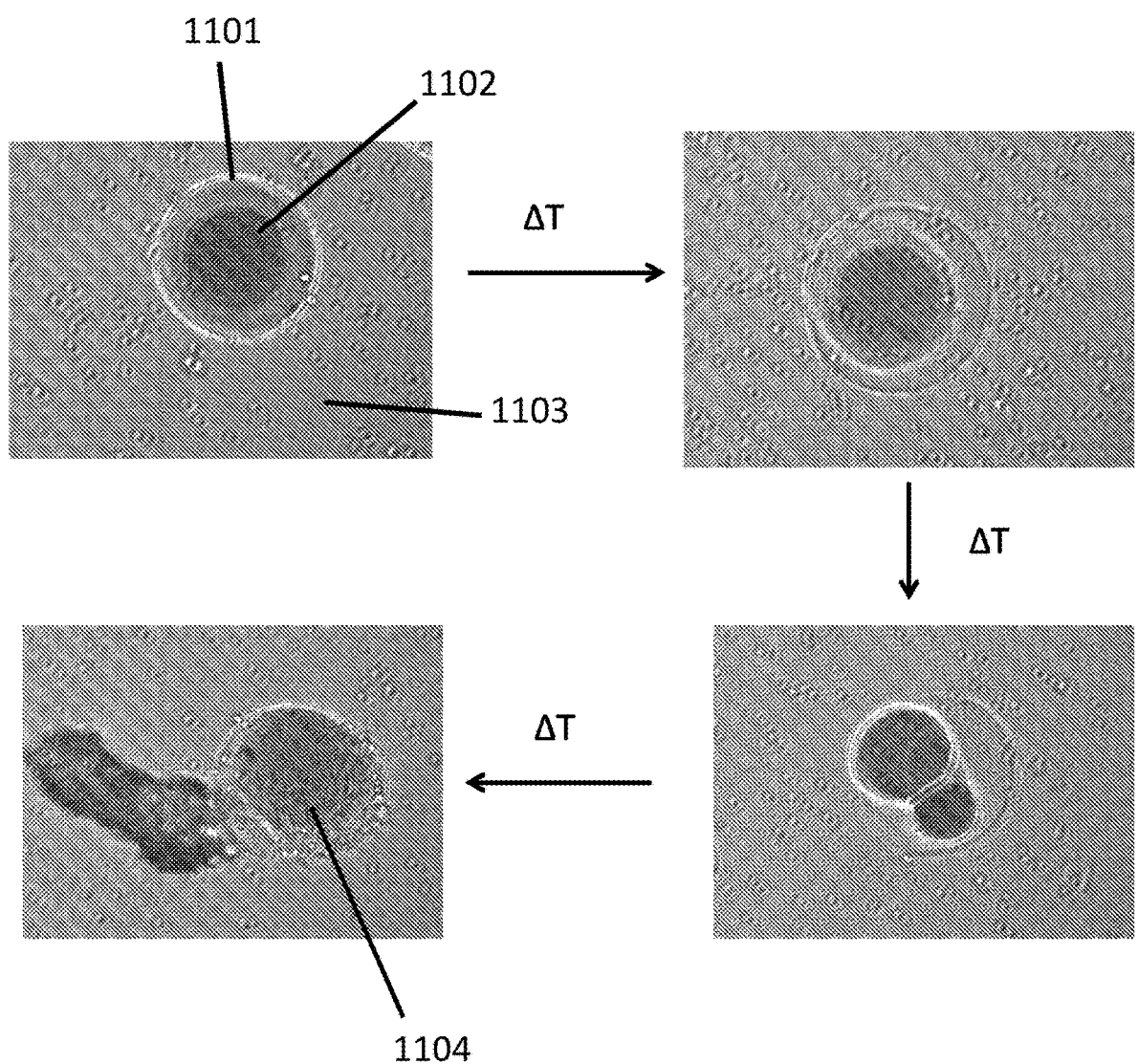
FIG. 11 provides micrographs of temperature-responsive capsules formed as described in Example 3.

Capsules were produced according to the method illustrated in FIG. 7 and the corresponding description of FIG. 7. The capsule shell wall was produced from N-isopropylacrylamide, a polymer that shrinks at a temperature above 32° C. With reference to FIG. 11, the capsules were made from a shell comprising the thermally responsive polymer 1101 and contained an aqueous interior 1102. The capsules were suspended in a oil phase 1103. Upon raising the temperature above 32° C. ($\Delta$T), the polymer in the capsule shell shrinks, leading to bursting of the capsule and release of the aqueous phase 1102 within the capsule directly into the surrounding oil phase 1103. The empty capsule shell 1104 is visible.

Example 4: Chemically-Responsive Capsules

Figure 12:
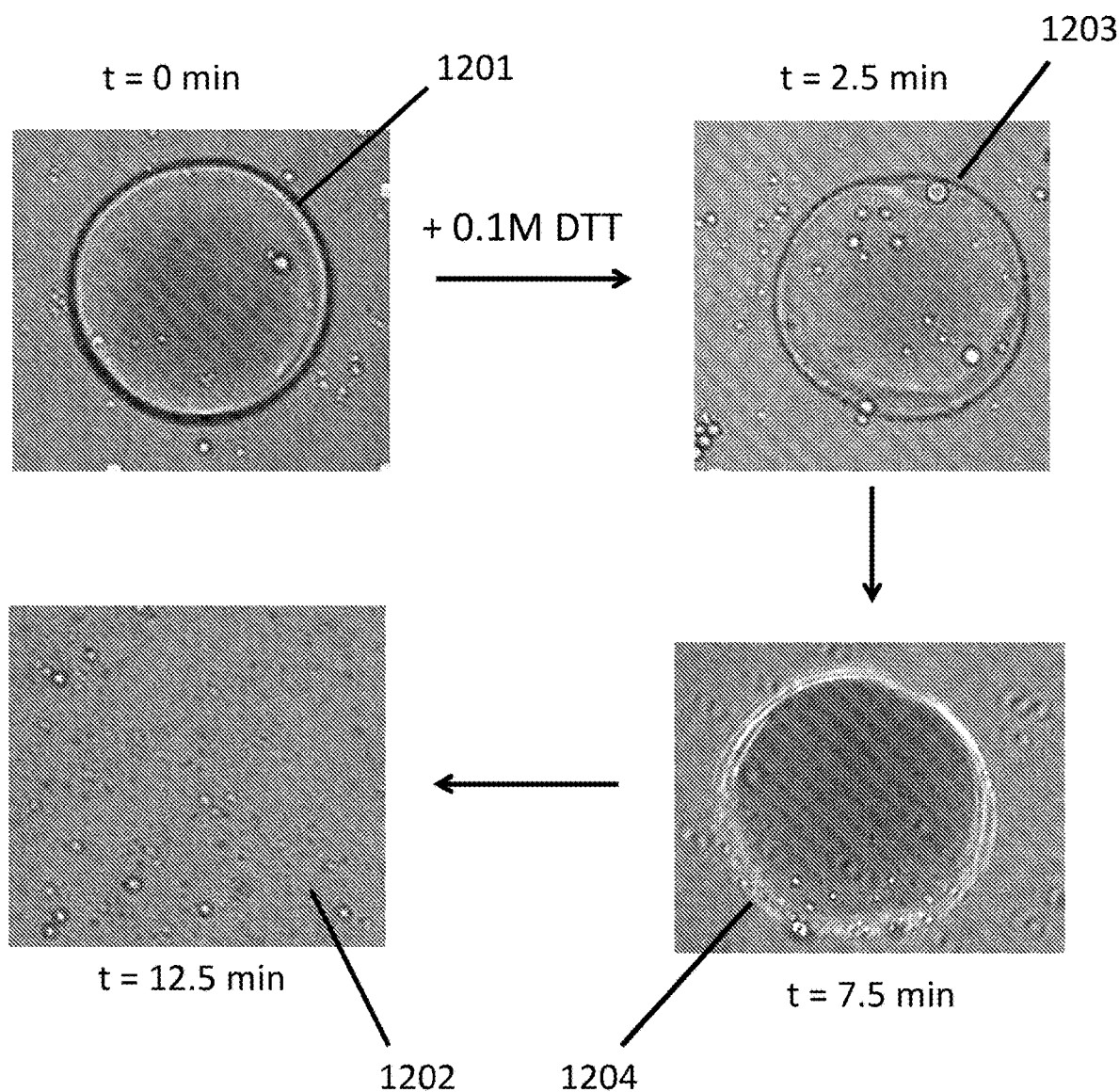
FIG. 12 provides micrographs of chemically-responsive capsules formed as described in Example 4.

Capsules were produced according to the method illustrated in FIG. 7 and the corresponding description of FIG. 7. The capsule shell wall was produced from a polymer comprising disulfide cross-links, which were dissolved after exposure to dithiothreitol (DTT). FIG. 12 shows selective dissolution of a capsule comprising disulfide cross-links after exposure to a medium containing 0.1M of DTT. The intact capsule 1201 was made with a shell comprising disulfide crosslinks. After 12.5 minutes of exposure to 0.1M DTT, the capsule shell dissolves, releasing the contents of the capsule, as shown in 1202. The appearance of the capsule at 2.5 minutes and 7.5 minutes is shown in 1203 and 1204, respectively.

Example 5: Examples of Configurations of Partitions

Many examples of different configurations of partitions are provided throughout this disclosure. FIG. 13 illustrates additional examples of configurations of partitions. In FIG. 13, the letters "A", "B", and "C" represent polynucleotide barcodes. The letter "S" represents an analyte (e.g., a sample). The letter "Z" represents another species, such as reagents that may be used to attach a barcode to a polynucleotide analyte. These configurations are in no way meant to be limiting and are provided only for the purposes of further illustrating certain embodiments of the invention. As described throughout this disclosure, any suitable configuration of any species (including species that are barcodes, analytes, and reagents) may be used. As described elsewhere in this disclosure, species may be introduced into capsules and droplets using any suitable method. Examples of suitable methods include flow focusing and picoinjection.

Figure 13A:
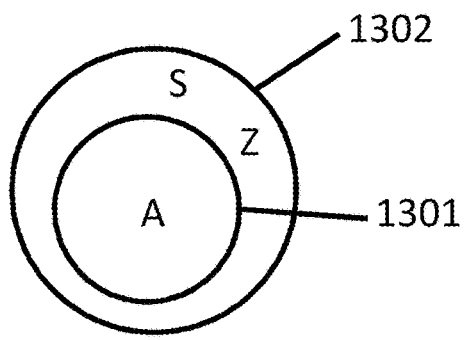
FIGS. 13A-E provide schematic examples of certain configurations of partitions, as described in Example 5.

The configuration of FIG. 13A is produced, using the methods described in this disclosure. With reference to FIG. 13A, an inner capsule or droplet of an emulsion 1301 comprising a barcode (A) is depicted. The inner capsule or droplet of an emulsion 1301 is contained within a partition 1302 that may be an outer capsule or a droplet of an emulsion. The medium between the inner capsule or droplet of an emulsion 1301 and the outer capsule or droplet of an emulsion 1302 comprises an analyte (S) and another species (Z) (e.g., a ligase, polymerase, etc.) for attaching the barcode (A) to the analyte (S). Using the methods described in this disclosure, the inner capsule or droplet of an emulsion 1301 can be induced to release its contents into the outer capsule or droplet of an emulsion 1302 in response to a stimulus, causing mixing of A, S, and Z.

Figure 13B:
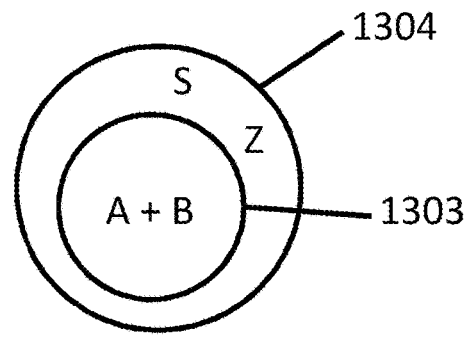

The configuration of FIG. 13B is produced, using the methods described in this disclosure. With reference to FIG. 13B, an inner capsule or droplet of an emulsion 1303 comprising two modular components of a barcode (A+B) is depicted. The inner capsule or droplet of an emulsion 1303 is contained within a partition 1304 that may be an outer capsule or droplet of an emulsion. The medium between the inner capsule or droplet of an emulsion 1303 and the outer capsule or droplet of an emulsion 1304 comprises an analyte (S) and another species (Z) (e.g., a ligase, polymerase, etc.) for attaching the barcode (A) to the analyte (S). The other species (Z) may also be used to assemble the two modular components of the barcode (A+B) and add the assembled barcode to the analyte (S), for example in a single ligation step. Using the methods described in this disclosure, the inner capsule or droplet of an emulsion 1303 can be induced to release its contents into the outer capsule or droplet of an emulsion 1304 in response to a stimulus, causing mixing of A, B, S, and Z.

Figure 13C:
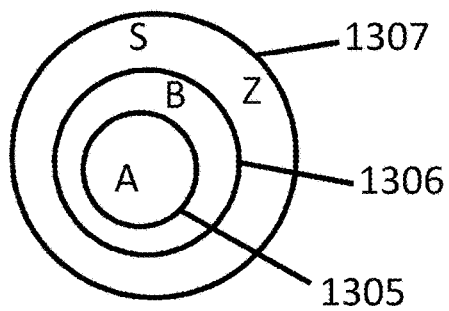

The configuration of FIG. 13C is produced, using the methods described in this disclosure. With reference to FIG. 13C, an inner capsule or droplet of an emulsion 1305 comprising a first modular component of a barcode (A) is depicted. The inner capsule or droplet of an emulsion 1305 is contained within a partition 1306 that may be an intermediate capsule or a droplet of an emulsion. The medium between the inner capsule or droplet of an emulsion 1305 and the intermediate capsule or droplet of an emulsion 1306 comprises a second modular component of a barcode (B). The intermediate capsule or droplet of an emulsion 1306 is contained within a partition 1307 that may be an outer capsule or droplet of an emulsion. The medium between the intermediate capsule or droplet of an emulsion 1306 and the outer capsule or droplet of an emulsion 1307 comprises an analyte (S) and another species (Z), each of which may be used as described above. Using the methods described in this disclosure, the inner capsule or droplet of an emulsion 1305 can be induced to release its contents into the intermediate capsule or droplet of an emulsion 1306 in response to a stimulus, causing mixing of A and B. Similarly, the intermediate capsule or droplet of an emulsion 1306 can be induced to release its contents into the outer capsule or droplet of an emulsion 1307, causing mixing of A, B, S, and Z (if the contents of 1305 have been released) or B, S, and Z (if the contents of 1305 have not been released).

Figure 13D:
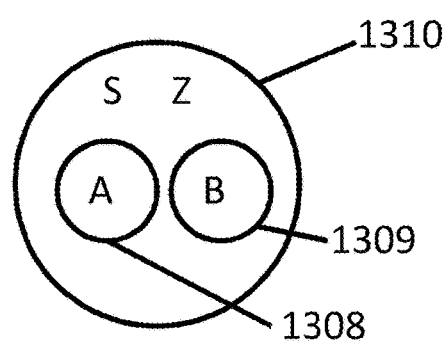

The configuration of FIG. 13D is produced, using the methods described in this disclosure. With reference to FIG. 13D, a first inner capsule or droplet of an emulsion 1308 comprises a first modular component of a barcode (A) and a second inner capsule or droplet of an emulsion 1309 comprises a second modular component of a barcode (B). The first and second inner capsules or droplets of an emulsion (1308 and 1309) are contained within a partition 1310 that may be an outer capsule or droplet of an emulsion. The medium between the first and second inner capsules or droplets of an emulsion (1308 and 1309) and the outer capsule or droplet of an emulsion 1310 comprises an analyte (S) and another species (Z), each of which may be used as described above. Using the methods described in this disclosure, either or both of the first 1308 or second 1309 inner capsules or droplets of an emulsion can be induced to release their contents into the outer capsule or droplet of an emulsion 1310 in response to a stimulus, causing mixing of A and/or B (depending on which inner capsules have released their contents), S, and Z.

Figure 13E:
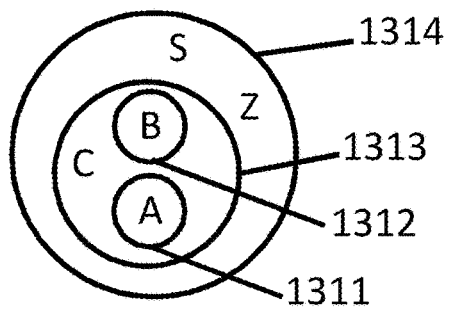

The configuration of FIG. 13E is produced, using the methods described in this disclosure. With reference to FIG. 13E, a first inner capsule or droplet of an emulsion 1311 comprises a first modular component of a barcode (A) and a second inner capsule or droplet of an emulsion 1312 comprises a second modular component of a barcode (B). The first and second inner capsules or droplets of an emulsion (1311 and 1312) are contained within an intermediate capsule or droplet of an emulsion 1313. The medium between the first and second inner capsules or droplets of an emulsion (1311 and 1312) and the intermediate capsule or droplet of an emulsion 1313 comprises a third modular component of a barcode (C). The intermediate capsule or droplet of an emulsion 1313 is contained within an outer capsule or droplet of an emulsion 1314. The medium between the intermediate capsule or droplet of an emulsion 1313 and the outer capsule or droplet of an emulsion 1314 comprises an analyte (S) and another species (Z), each of which may be used as described above. Using the methods described in this disclosure, either or both of the first 1311 or second 1312 inner capsules or droplets of an emulsion can be induced to release their contents into the intermediate capsule or droplet of an emulsion 1313 in response to a stimulus, causing mixing of A and/or B (depending on which inner capsules have released their contents) with C. Similarly, the intermediate capsule or droplet of an emulsion 1313 can be induced to release its contents into the outer capsule or droplet of an emulsion 1314, causing mixing of A, B, C, S, and Z, depending on which contents of 1311 and 1312 have been released.

Example 6: Spotting of Species Within Wells

Figure 14:
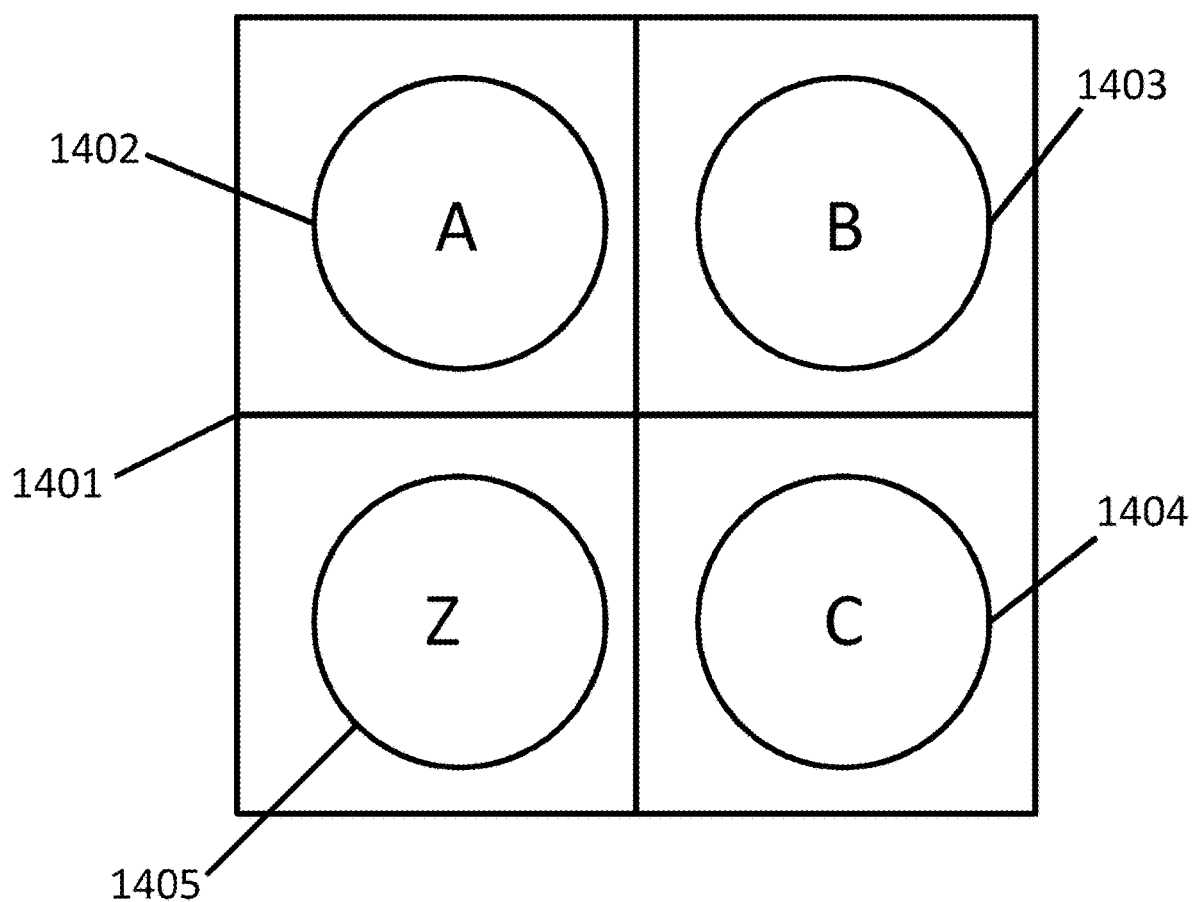
FIG. 14 provides a schematic example of discrete spots on a surface of a well, as described in Example 6.

A well comprising spots in the configuration of FIG. 14 is produced, using the methods described in this disclosure. With reference to FIG. 14, the bottom surface of a well 1401 is depicted. The shapes used for the well and the spots are merely for illustrative purposes and in no way meant to be limiting. Any suitable shape may be used for the well and/or any spot. With reference to FIG. 14, four spots are shown, each spot in one quadrant of the bottom surface of the well. The number of spots, and the contents of the spots, are also merely illustrative. Any number of spots or suitable contents of spots may be used. In FIG. 14, spot 1402 comprises a first modular component of a barcode (A), spot 1403 comprises a second modular component of a barcode (B), spot 1404 comprises a third modular component of a barcode (C), and spot 1405 comprises a reagent (Z). The spots are separated, to prevent mixing of the contents of the spots before a sample is added. By adding a sample (e.g., an analyte in a medium) to the well, the contents of the spots can be mixed with the sample at the appropriate time.

Example 7: Sonication of Encapsulated Polynucleotide

Polynucleotides (e.g., genomic DNA) are isolated from cells according to methods known in the art. The polynucleotides are encapsulated in a capsule and/or within a hydrogel matrix. The polynucleotides are fragmented by exposing the capsules and/or hydrogel matrix to shear stress induced by ultrasonic waves. Sheared, encapsulated polynucleotide is generated.

Figure 15A:
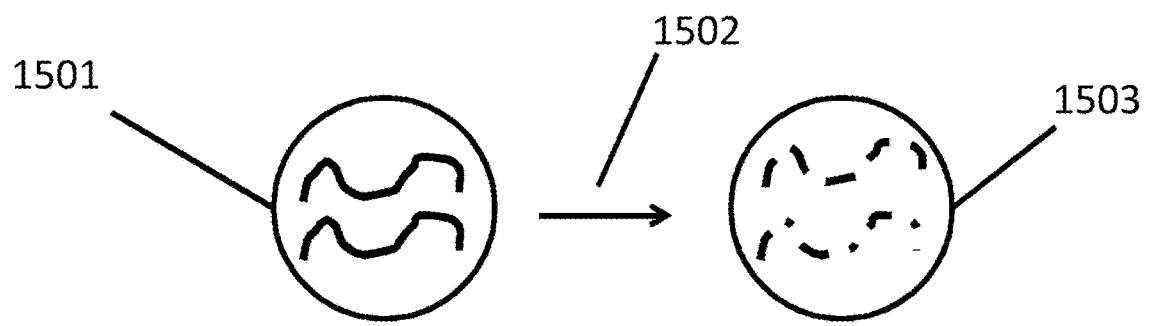
FIG. 15A-B provide schematic examples of shearing encapsulated DNA and exposing it to reagents for further processing, as described in Example 7.

With reference to FIG. 15A, a polynucleotide (e.g., isolated from a cell) is encapsulated in a capsule or a gel droplet 1501. As described elsewhere in this disclosure, the polynucleotide can be encapsulated such that each capsule or gel droplet comprises only a single copy of a particular polynucleotide, so that each capsule or gel droplet contains a mixture of non-overlapping fragments. The capsule or gel droplet is sonicated 1502 to shear the polynucleotide. The capsule or gel droplet is configured to withstand the sonication. The result is a capsule or gel droplet comprising fragmented polynucleotide 1503.

Figure 15B:
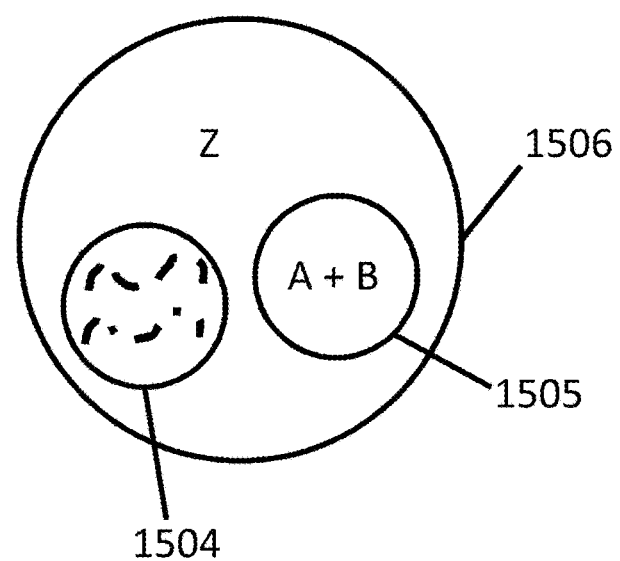

The encapsulated fragmented polynucleotide can then be processed according to any suitable method, including methods known in the art and methods described in this disclosure. FIG. 15B shows an example of further processing. With reference to FIG. 15B, the a first inner capsule or hydrogel droplet comprising sheared polynucleotides 1504 (as generated, e.g., in FIG. 15A) is encapsulated into an outer capsule 1506. The outer capsule 1506 also comprises a second inner capsule 1505. The second inner capsule 1505 comprises two modular components of a barcode (A+B). The medium between the outer capsule 1506 and the two inner capsules 1504 and 1505 comprises a reagent (Z). Upon releasing the contents of the inner capsules, the sheared polynucleotide will mix with A, B, and Z. In some cases, a plurality of capsules or hydrogel droplets comprising a sheared polynucleotide (i.e., a plurality of 1504s) may be encapsulated in the outer capsule 1506.

While preferred embodiments of the present invention have been shown and described herein, it will be obvious to those skilled in the art that such embodiments are provided by way of example only. Numerous variations, changes, and

What is claimed is:

1. A system, comprising:
a plurality of capsules; and
a plurality of partitions,
wherein a partition of said plurality of partitions comprises (i) a first species and (ii) a capsule of said plurality of capsules, wherein said capsule comprises a second species, wherein said capsule is configured to release said second species into said partition upon application of a stimulus, and wherein said stimulus comprises one or more members selected from the group consisting of a change in ion concentration, a reducing agent, a light stimulus, an electrical stimulus, and a magnetic stimulus.

2. The system of claim 1, wherein at least one of said first species and said second species is selected from the group consisting of a reagent and an analyte.

3. The system of claim 2, wherein said reagent comprises one or more members selected from the group consisting of a protein, a polynucleotide, an enzyme, an antibody, a barcode, an adapter, a buffer, a small molecule, a detergent, a dye, and a polymer.

4. The system of claim 3, wherein said enzyme comprises a proteinase, a restriction enzyme, a ligase, a polymerase, a fragmentase, a reverse transcriptase, or a transposase.

5. The system of claim 4, wherein said restriction enzyme is a rare cutter.

6. The system of claim 3, wherein said barcode comprises an oligonucleotide barcode molecule.

7. The system of claim 2, wherein said analyte comprises a cell, a polynucleotide, a chromosome, a protein, a peptide, a polysaccharide, a sugar, a lipid, or a small molecule.

8. The system of claim 2, wherein said analyte comprises a polynucleotide molecule.

9. The system of claim 8, wherein said polynucleotide molecule is a deoxyribonucleic acid (DNA) molecule, a ribonucleic acid molecule, or complementary DNA (cDNA) molecule.

10. The system of claim 2, wherein said analyte comprises a cell.

11. The system of claim 10, wherein said partition comprises said cell and does not include any additional cells.

12. The system of claim 2, wherein said first species is said reagent and said second species is said analyte.

13. The system of claim 2, wherein said first species is said analyte and said second species is said reagent.

14. The system of claim 1, wherein capsules of said plurality of capsules comprise, on average, one chromosome.

15. The system of claim 1, wherein partitions of said plurality of partitions comprise, on average, a single capsule of said plurality of capsules.

16. The system of claim 1, wherein said partition does not include any additional capsule of said plurality of capsules.

17. The system of claim 1, wherein said capsule comprises an additional partition.

18. The system of claim 17, wherein said additional partition is selected from the group consisting of an additional capsule and a droplet.

19. The system of claim 1, wherein said capsule comprises a shell selected from the group consisting of a polymeric shell, a hydrogel, a hydrophilic shell, a hydrophobic shell, a shell with a net positive charge, a shell with a net negative charge, and a shell with a neutral charge.

20. The system of claim 1, wherein said partition comprises a fluid that is less dense than said capsule.

21. The system of claim 1, wherein said partition comprises a fluid that is more dense than said capsule.

22. The system of claim 1, wherein said plurality of partitions is a plurality of aqueous droplets, wherein said first species is a cell, wherein said capsule is a gel bead, and wherein said second species is an oligonucleotide barcode molecule.

23. The system of claim 1, wherein said capsule is configured to be degraded or disrupted by said stimulus, thereby releasing said second species into said partition.

24. The system of claim 1, wherein said second species is an oligonucleotide barcode molecule releasably attached to said capsule.

25. The system of claim 24, wherein said capsule comprises at least 10,000 oligonucleotide barcode molecules releasably attached thereto, wherein said at least 10,000 oligonucleotide barcode molecules comprises said oligonucleotide barcode molecule, and wherein said oligonucleotide barcode molecule is configured to release from said capsule upon application of said stimulus.

26. The system of claim 1, wherein said capsule is a gel bead.

27. The system of claim 1, wherein said plurality of partitions comprises a plurality of wells.

28. The system of claim 1, wherein said change in ion concentration includes a change in pH within said capsule.

29. The system of claim 1, wherein said partition comprises magnetic nanoparticles responsive to said magnetic stimulus.

30. The system of claim 1, wherein said partition comprises electrically sensitive particles responsive to said electrical stimulus.

31. The system of claim 1, wherein said partition comprises nanoparticles or chromophores responsive to said light stimulus.

32. The system of claim 1, wherein said partition comprises photo switchable materials responsive to said light stimulus.

33. The system of claim 1, wherein said electrical stimulus comprises application of an electric field.

34. The system of claim 1, wherein said magnetic stimulus comprises application of a magnetic field.

35. The system of claim 1, wherein said light stimulus comprises application of ultraviolet or visible light.

36. The system of claim 1, wherein said stimulus is said change in ion concentration.

37. The system of claim 1, wherein said stimulus is said reducing agent.

38. The system of claim 1, wherein said stimulus is said light stimulus.

39. The system of claim 1, wherein said stimulus is said electrical stimulus.

40. The system of claim 1, wherein said stimulus is said magnetic stimulus.

* * * * *

SEQUENCE LISTING

<160> NUMBER OF SEQ ID NOS: 8

<210> SEQ ID NO 1
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 1
ggccnnnnng gcc                                                          13

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other

<400> SEQUENCE: 2
caannnnngt gg                                                           12

<210> SEQ ID NO 3
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(10)
<223> OTHER INFORMATION: a, c, t, g, unknown or other

<400> SEQUENCE: 3
gaannnnnnn ttgg                                                         14

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 4
gaacnnnnnn tcc                                                          13

<210> SEQ ID NO 5

```
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 5
gaagnnnnnn tac                                                       13

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(9)
<223> OTHER INFORMATION: a, c, t, g, unknown or other

<400> SEQUENCE: 6
gaacnnnnnc tc                                                        12

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: a, c, t, g, unknown or other

<400> SEQUENCE: 7
gaacnnnnnn tac                                                       13

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Phe Leu Gly Lys
1               5
```